US006281016B1

(12) United States Patent
Malvar et al.

(10) Patent No.: US 6,281,016 B1
(45) Date of Patent: Aug. 28, 2001

(54) BROAD-SPECTRUM INSECT RESISTANT TRANSGENIC PLANTS

(75) Inventors: Thomas Malvar, Duglin; Amy Jelen Gilmer, Langhorne, both of PA (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 09/253,331

(22) Filed: Feb. 19, 1999

Related U.S. Application Data

(60) Division of application No. 08/922,505, filed on Sep. 3, 1997, now Pat. No. 6,110,464, which is a continuation-in-part of application No. 08/754,490, filed on Nov. 20, 1996, now Pat. No. 6,017,534.

(51) Int. Cl.[7] .............................. C12N 5/04; C12N 5/00; C12N 5/02; C12N 15/82; A01H 1/00

(52) U.S. Cl. .......................... 435/419; 435/410; 435/412; 435/415; 435/424; 435/426; 435/427; 435/430; 800/278; 800/279; 800/295; 800/300.1; 800/301; 800/314; 800/320; 800/320.1; 800/320.3; 800/322

(58) Field of Search .................................... 435/410, 412, 435/415, 419, 424, 426, 427, 430; 800/278, 279, 295, 300.1, 301, 314, 320, 320.1, 320.3, 322

(56) References Cited

U.S. PATENT DOCUMENTS

| | | |
|---|---|---|
| 5,055,294 | 10/1991 | Gilroy . |
| 5,128,130 | 7/1992 | Gilroy et al. . |
| 5,349,124 | 9/1994 | Fischhoff et al. . |
| 5,380,831 | 1/1995 | Adang et al. . |
| 5,384,253 | 1/1995 | Krzyzek et al. . |
| 5,441,884 | 8/1995 | Baum . |
| 5,449,681 | 9/1995 | Wickiser . |
| 5,500,365 | 3/1996 | Fischhoff et al. . |
| 5,508,264 | 4/1996 | Bradfisch et al. . |
| 5,593,881 | 1/1997 | Thompson et al. . |

FOREIGN PATENT DOCUMENTS

| | | |
|---|---|---|
| 0193259 | 9/1986 | (EP) . |
| 0 228 838 B1 | 12/1986 | (EP) . |
| 0290395 | 11/1988 | (EP) . |
| 0213818 | 2/1991 | (EP) . |
| 0292435 | 7/1995 | (EP) . |
| 0359472 | 12/1995 | (EP) . |
| 0731170 | 9/1996 | (EP) . |
| WO 84/02913 | 8/1984 | (WO) . |
| WO93/07278 | 4/1993 | (WO) . |
| WO95/02058 | 1/1995 | (WO) . |
| WO95/06730 | 3/1995 | (WO) . |
| WO95/30752 | 11/1995 | (WO) . |
| WO95/30753 | 11/1995 | (WO) . |
| WO 98/02039 | 1/1998 | (WO) . |

OTHER PUBLICATIONS

De Maagd et al., "Different domains of *Bacillus thuringiensis* δ–endotoxins can bind to insect midgut membrane proteins on ligand blots," *Applied and Environmental Microbiology*, 62(8):2753–2757, 1996.

Honée et al., "A translation fusion product of two different insecticidal crystal protein genes of *Bacillus thuringiensis* exhibits an enlarged insecticidal spectrum," *Applied and Environmental Microbiology*, 56(3):823–825, 1990.

Adang et al., "The reconstruction and expression of a *Bacillus thuringiensis cryIIIA* gene in protoplasts and potato plants," *Plant Mol. Biol.*, 21:1131–1145, 1993.

Bernhard, "Studies on the delta–endotoxin of *Bacillus thuringiensis var. tenebrionis*," FEMS *Microbiol. Letters*, 33:261–265, 1986.

Herrnstadt et al., "A new strain of *Bacillus thuringiensis* with activity against Coleopteran insects," *Bio/Technology*, 4:305–308, 1986.

Höfte et al., "Structural and functional analysis of a clones delta endotoxin of *Bacillus thuringiensis berliner* 1715," *Eur. J. Biochem.*, 171:273–280, 1986.

Kller et al., "Cloning and expression of the crystal protein genes from *Bacillus thuringiensis* strain *berliner* 1715," *EMBO J.*, 1(7):791–799, 1982.

Koziel et al., "Field performance of elite transgenic maize plants expressing an insecticidal protein derived from *Bacillus thuringiensis*," *Bio/Technol.*, 11:194–200, 1993.

Krieg et al., "*Bacillus thuringiensis var. tenebrionis*, a new pathotype effective against larvae of Coleoptera," *Z. ang. Ent.*, 96:500–508, 1983.

Krieg et al., "New results on *Bacillus thuringiensis var. tenebrionis* with special regard to its effect on the Colorado beetle (*Leptinotarsa decemlineata*)," *Anz. Schädlingskde Pflanzenschutz Umweltschutz*, 57(8):145–150, 1984.

Murray et al., "Analysis of unstable RNA transcripts of insecticidal crystal protein genes of *Bacillus thuringiensis* in transgenic plants and electroporated protoplasts," *Plant Mol. Biol.*, 16:1035–1050, 1991.

Perlak et al., "Genetically improved potatoes: protection from damage by Colorado potato beetles," *Plant Mol. Biol.*, 22:313–321, 1993.

Perlak et al., "Insect resistant cotton plants," *Bio/Technol.*, 8:939–943, 1990.

(List continued on next page.)

*Primary Examiner*—Mark Navarro
(74) *Attorney, Agent, or Firm*—T. K. Ball; Howrey Simon Arnold & White, LLP

(57) ABSTRACT

Disclosed are novel synthetically-modified *B. thuringiensis* chimeric crystal proteins having improved insecticidal activity against coleopteran, dipteran and lepidopteran insects. Also disclosed are the nucleic acid segments encoding these novel peptides. Methods of making and using these genes and proteins are disclosed as well as methods for the recombinant expression, and transformation of suitable host cells. Transformed host cells and tansgenic plants expressing the modified endotoxin are also aspects of the invention.

17 Claims, 3 Drawing Sheets

OTHER PUBLICATIONS

Figure 1A:
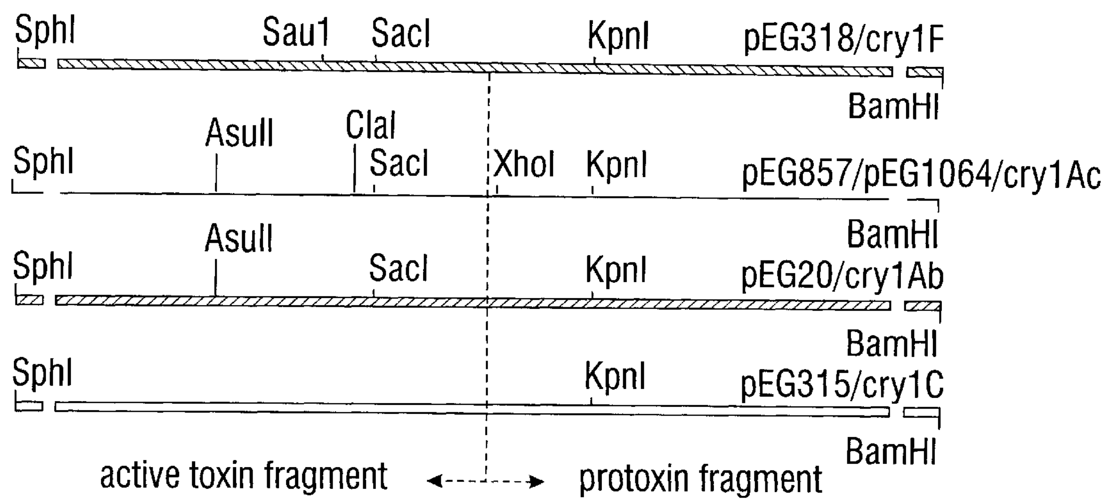

Perlak et al., "Modification of the coding sequence enhances plant expression of insect control protein genes," *Proc. Natl. Acad. Sci. USA, Biochem.*, 88:3324–3328, 1991.

Schnepf and Whiteley, "Cloning and expression of the *Bacillus thuringiensis* crystal protein gene in *Escherichia coli*," *Proc. Natl. Acad. Sci. USA*, 78(5), 2893–2897, 1981.

Baum et al., "Novel Cloning Vectors for *Bacillus thuringiensis*," *Appl. Envion. Microbiol.*, 56(11):3420–3428, 1990.

Bosch et al., "Recombinant *Bacillus thuringiensis* Crystal Proteins with New Properties: Possibilities for Resistance Management," *Bio/Technology*, 12:915–918, 1994.

Caramori et al., "In vivo generation of hybrids between two *Bacillus thuringiensis* insect–toxin–encoding genes, " *Gene*, 98(1):37–44, 1991.

Caramori et al., "*Bacillus thruingiensis kurstaki* hybrid endotoxin genes generated by In Vivo recombination," ISBN 1–56081–028–9, 0(0):259–267, 1990.

Gill et al., "Identification, Isolation, and Cloning of a *Bacillus thuringiensis* CryIAc Toxin–binding Protein from the Midgut of the Lepidopteran Insect *Heliothis virescens*," *J. Biol. Chem.* 270(45):27277–27282, 1995.

Grochulski et al., "*Bacillus thuringiensis* CrylA(a) Insecticidal Toxin: Crystal Structure and Channel Formation," *J. Mol. Biol.*, 254:447–464, 1995.

Honée et al., "The C–terminal domain of the toxic fragment of a *Bacillus thuringiensis* crystal protein determines receptor binding," *Mol. Microbiol.*, 5(11):2799–2806, 1991.

Knight et al., "Molecular Cloning of an Insect Aminopeptidase N that Serves as a Receptor for *Bacillus thuringiensis* CryIA(c) Toxin," *J. Biol. Chem.*, 270(30):17765–17770, 1995.

Lee et al., "Domain III Exchanges of *Bacillus thuringiensis* CryIA toxins affect binding to different gypsy moth midgut receptors," *Biochem. Biophysical Research Communications*, 216(1):306–312, 1995.

Masson et al., "The CryIA(c) Receptor Purified from *Manduca sexta* Displays Multiple Specificities" *J. Biol. Chem.*, 270(35):20309–20315, 1995.

Mettus et al., "Expression of *Bacillus thuringiensis* δ–Endotoxin Genes during Vegetative Growth," *Appl. Environ. Microbiol.*, 56(4):1128–1134, 1990.

Nakamura et al., "Construction of chimeric insecticidal proteins between the 130–kDa and 135–kDa proteins of *Bacillus thuringiensis* subsp. *aizawai* for analysis of structure–function relationship," *Agric. Biol. Chem.*, 54(3):715–724, 1990.

Racapéet al., "Properties of the pores formed by parental and chimeric *Bacillus thuringiensis* insecticidal toxins in planar lipid bilayer membranes," *Biophysical J.* 72(2) (part 2 of 2), A82, M–Pos329, 1997, ISSN: 0006–3495.

Raymond et al., "Larvicidal activity of chimeric *Bacillus thuringiensis* protoxins," *Mol. Microbiol.*, 4(11):1967–1973, 1990.

Rudd et al., "Domain III Substitution in *Bacillus thuringlensis* Delta–Endotoxin CryIA(b) Results in Superior Toxicity for *Spodoptera exigua* and Altered Membrane Protein Recognition," *Appl. Environ. Microbiol.*, 62(5):1537–1543, 1996.

Rudd et al., "Different Domains of *Bacillus thuringiensis* δ–Endotixins Can Bind to Insect Midgut Membrane Proteins on Ligand Blots," *Appl. Environ. Microbiol.*, 62(8):2753–2757, 1996.

Schnepf et al., "Specificity–determining Regions of a Lepidopteran–specific Insecticidal Protein Produced by *Bacillus thuringiensis*," *J. Biol. Chem.* 265(34):20923–20930, 1990.

Shadenkov et al., "Construction of a hybrid gene from CryIIIA and CryIA(a) δ–endotoxin genes of *Bacillus thuringiensis* and expression of its derivatives in *Escherichia coli* cells," *Mol. Biol.*, 27(4):586–591, Part 2, 1993.

Thompson et al., "Structure, Function and Engineering of *Bacillus thuringiensis* Toxins,"*Genetic Engineering*, 17:99–117, 1995.

Vachon et al., "Mode of action of *Bacillus thuringiensis* insecticidal crystal proteins: A study of chimeric toxins," *FASEB Journal* 10(3), A74, 429, 1996, ISSN: 0892–6638.

SEQUENCE LISTING

```
<160> NUMBER OF SEQ ID NOS:   35

<210> SEQ ID NO 1
<211> LENGTH: 23
<212> TYPE: DNA
<213> ORGANISM: Artificial
<220> FEATURE:
<223> OTHER INFORMATION: Description of Artificial Sequence: Synthetic

<400> SEQUENCE: 1

ggatagcact catcaaaggt acc                                              23


<210> SEQ ID NO 2
<211> LENGTH: 27
<212> TYPE: DNA
<213> ORGANISM: Artificial
<220> FEATURE:
<223> OTHER INFORMATION: Description of Artificial Sequence: Synthetic

<400> SEQUENCE: 2

gaagatatcc aattcgaaca gtttccc                                          27


<210> SEQ ID NO 3
<211> LENGTH: 28
<212> TYPE: DNA
<213> ORGANISM: Artificial
<220> FEATURE:
<223> OTHER INFORMATION: Description of Artificial Sequence: Synthetic

<400> SEQUENCE: 3

catattctgc ctcgagtgtt gcagtaac                                         28


<210> SEQ ID NO 4
<211> LENGTH: 17
<212> TYPE: DNA
<213> ORGANISM: Artificial
<220> FEATURE:
<223> OTHER INFORMATION: Description of Artificial Sequence: Synthetic

<400> SEQUENCE: 4

cccgatcggc cgcatgc                                                     17


<210> SEQ ID NO 5
<211> LENGTH: 17
<212> TYPE: DNA
<213> ORGANISM: Artificial
<220> FEATURE:
<223> OTHER INFORMATION: Description of Artificial Sequence: Synthetic

<400> SEQUENCE: 5

cattggagct ctccatg                                                     17


<210> SEQ ID NO 6
<211> LENGTH: 16
<212> TYPE: DNA
<213> ORGANISM: Artificial
<220> FEATURE:
<223> OTHER INFORMATION: Description of Artificial Sequence: Synthetic

<400> SEQUENCE: 6

gcactacgat gtatcc                                                      16


<210> SEQ ID NO 7
<211> LENGTH: 20
```

-continued

```
<212> TYPE: DNA
<213> ORGANISM: Artificial
<220> FEATURE:
<223> OTHER INFORMATION: Description of Artificial Sequence: Synthetic

<400> SEQUENCE: 7

catcgtagtg caactcttac                                                   20


<210> SEQ ID NO 8
<211> LENGTH: 39
<212> TYPE: DNA
<213> ORGANISM: Artificial
<220> FEATURE:
<223> OTHER INFORMATION: Description of Artificial Sequence: Synthetic

<400> SEQUENCE: 8

ccaagaaaat actagagctc ttgttaaaaa aggtgttcc                              39


<210> SEQ ID NO 9
<211> LENGTH: 3531
<212> TYPE: DNA
<213> ORGANISM: Artificial
<220> FEATURE:
<223> OTHER INFORMATION: Description of Artificial Sequence: Synthetic
<221> NAME/KEY: CDS
<222> LOCATION: (1)..(3531)

<400> SEQUENCE: 9

atg gat aac aat ccg aac atc aat gaa tgc att cct tat aat tgt tta       48
Met Asp Asn Asn Pro Asn Ile Asn Glu Cys Ile Pro Tyr Asn Cys Leu
1               5                   10                  15

agt aac cct gaa gta gaa gta tta ggt gga gaa aga ata gaa act ggt       96
Ser Asn Pro Glu Val Glu Val Leu Gly Gly Glu Arg Ile Glu Thr Gly
            20                  25                  30

tac acc cca atc gat att tcc ttg tcg cta acg caa ttt ctt ttg agt      144
Tyr Thr Pro Ile Asp Ile Ser Leu Ser Leu Thr Gln Phe Leu Leu Ser
        35                  40                  45

gaa ttt gtt ccc ggt gct gga ttt gtg tta gga cta gtt gat ata ata      192
Glu Phe Val Pro Gly Ala Gly Phe Val Leu Gly Leu Val Asp Ile Ile
    50                  55                  60

tgg gga att ttt ggt ccc tct caa tgg gac gca ttt ctt gta caa att      240
Trp Gly Ile Phe Gly Pro Ser Gln Trp Asp Ala Phe Leu Val Gln Ile
65                  70                  75                  80

gaa cag tta att aac caa aga ata gaa gaa ttc gct agg aac caa gcc      288
Glu Gln Leu Ile Asn Gln Arg Ile Glu Glu Phe Ala Arg Asn Gln Ala
                85                  90                  95

att tct aga tta gaa gga cta agc aat ctt tat caa att tac gca gaa      336
Ile Ser Arg Leu Glu Gly Leu Ser Asn Leu Tyr Gln Ile Tyr Ala Glu
            100                 105                 110

tct ttt aga gag tgg gaa gca gat cct act aat cca gca tta aga gaa      384
Ser Phe Arg Glu Trp Glu Ala Asp Pro Thr Asn Pro Ala Leu Arg Glu
        115                 120                 125

gag atg cgt att caa ttc aat gac atg aac agt gcc ctt aca acc gct      432
Glu Met Arg Ile Gln Phe Asn Asp Met Asn Ser Ala Leu Thr Thr Ala
    130                 135                 140

att cct ctt ttt gca gtt caa aat tat caa gtt cct ctt tta tca gta      480
Ile Pro Leu Phe Ala Val Gln Asn Tyr Gln Val Pro Leu Leu Ser Val
145                 150                 155                 160

tat gtt caa gct gca aat tta cat tta tca gtt ttg aga gat gtt tca      528
Tyr Val Gln Ala Ala Asn Leu His Leu Ser Val Leu Arg Asp Val Ser
                165                 170                 175

gtg ttt gga caa agg tgg gga ttt gat gcc gcg act atc aat agt cgt      576
Val Phe Gly Gln Arg Trp Gly Phe Asp Ala Ala Thr Ile Asn Ser Arg
```

-continued

```
            180                 185                 190

tat aat gat tta act agg ctt att ggc aac tat aca gat tat gct gta      624
Tyr Asn Asp Leu Thr Arg Leu Ile Gly Asn Tyr Thr Asp Tyr Ala Val
        195                 200                 205

cgc tgg tac aat acg gga tta gaa cgt gta tgg gga ccg gat tct aga      672
Arg Trp Tyr Asn Thr Gly Leu Glu Arg Val Trp Gly Pro Asp Ser Arg
    210                 215                 220

gat tgg gta agg tat aat caa ttt aga aga gaa tta aca cta act gta      720
Asp Trp Val Arg Tyr Asn Gln Phe Arg Arg Glu Leu Thr Leu Thr Val
225                 230                 235                 240

tta gat atc gtt gct ctg ttc ccg aat tat gat agt aga aga tat cca      768
Leu Asp Ile Val Ala Leu Phe Pro Asn Tyr Asp Ser Arg Arg Tyr Pro
                245                 250                 255

att cga aca gtt tcc caa tta aca aga gaa att tat aca aac cca gta      816
Ile Arg Thr Val Ser Gln Leu Thr Arg Glu Ile Tyr Thr Asn Pro Val
            260                 265                 270

tta gaa aat ttt gat ggt agt ttt cga ggc tcg gct cag ggc ata gaa      864
Leu Glu Asn Phe Asp Gly Ser Phe Arg Gly Ser Ala Gln Gly Ile Glu
        275                 280                 285

aga agt att agg agt cca cat ttg atg gat ata ctt aac agt ata acc      912
Arg Ser Ile Arg Ser Pro His Leu Met Asp Ile Leu Asn Ser Ile Thr
    290                 295                 300

atc tat acg gat gct cat agg ggt tat tat tat tgg tca ggg cat caa      960
Ile Tyr Thr Asp Ala His Arg Gly Tyr Tyr Tyr Trp Ser Gly His Gln
305                 310                 315                 320

ata atg gct tct cct gta ggg ttt tcg ggg cca gaa ttc act ttt ccg     1008
Ile Met Ala Ser Pro Val Gly Phe Ser Gly Pro Glu Phe Thr Phe Pro
                325                 330                 335

cta tat gga act atg gga aat gca gct cca caa caa cgt att gtt gct     1056
Leu Tyr Gly Thr Met Gly Asn Ala Ala Pro Gln Gln Arg Ile Val Ala
            340                 345                 350

caa cta ggt cag ggc gtg tat aga aca tta tcg tcc act tta tat aga     1104
Gln Leu Gly Gln Gly Val Tyr Arg Thr Leu Ser Ser Thr Leu Tyr Arg
        355                 360                 365

aga cct ttt aat ata ggg ata aat aat caa caa cta tct gtt ctt gac     1152
Arg Pro Phe Asn Ile Gly Ile Asn Asn Gln Gln Leu Ser Val Leu Asp
    370                 375                 380

ggg aca gaa ttt gct tat gga acc tcc tca aat ttg cca tcc gct gta     1200
Gly Thr Glu Phe Ala Tyr Gly Thr Ser Ser Asn Leu Pro Ser Ala Val
385                 390                 395                 400

tac aga aaa agc gga acg gta gat tcg ctg gat gaa ata ccg cca cag     1248
Tyr Arg Lys Ser Gly Thr Val Asp Ser Leu Asp Glu Ile Pro Pro Gln
                405                 410                 415

aat aac aac gtg cca cct agg caa gga ttt agt cat cga tta agc cat     1296
Asn Asn Asn Val Pro Pro Arg Gln Gly Phe Ser His Arg Leu Ser His
            420                 425                 430

gtt tca atg ttt cgt tca ggc ttt agt aat agt agt gta agt ata ata     1344
Val Ser Met Phe Arg Ser Gly Phe Ser Asn Ser Ser Val Ser Ile Ile
        435                 440                 445

aga gct cca atg ttt tct tgg acg cac cgt agt gca acc cct aca aat     1392
Arg Ala Pro Met Phe Ser Trp Thr His Arg Ser Ala Thr Pro Thr Asn
    450                 455                 460

aca att gat ccg gag agg att act caa ata cca ttg gta aaa gca cat     1440
Thr Ile Asp Pro Glu Arg Ile Thr Gln Ile Pro Leu Val Lys Ala His
465                 470                 475                 480

aca ctt cag tca ggt act act gtt gta aga ggg ccc ggg ttt acg gga     1488
Thr Leu Gln Ser Gly Thr Thr Val Val Arg Gly Pro Gly Phe Thr Gly
                485                 490                 495

gga gat att ctt cga cga aca agt gga gga cca ttt gct tat act att     1536
```

-continued

```
Gly Asp Ile Leu Arg Arg Thr Ser Gly Gly Pro Phe Ala Tyr Thr Ile
            500                 505                 510

gtt aat ata aat ggg caa tta ccc caa agg tat cgt gca aga ata cgc     1584
Val Asn Ile Asn Gly Gln Leu Pro Gln Arg Tyr Arg Ala Arg Ile Arg
        515                 520                 525

tat gcc tct act aca aat cta aga att tac gta acg gtt gca ggt gaa     1632
Tyr Ala Ser Thr Thr Asn Leu Arg Ile Tyr Val Thr Val Ala Gly Glu
    530                 535                 540

cgg att ttt gct ggt caa ttt aac aaa aca atg gat acc ggt gac cca     1680
Arg Ile Phe Ala Gly Gln Phe Asn Lys Thr Met Asp Thr Gly Asp Pro
545                 550                 555                 560

tta aca ttc caa tct ttt agt tac gca act att aat aca gct ttt aca     1728
Leu Thr Phe Gln Ser Phe Ser Tyr Ala Thr Ile Asn Thr Ala Phe Thr
                565                 570                 575

ttc cca atg agc cag agt agt ttc aca gta ggt gct gat act ttt agt     1776
Phe Pro Met Ser Gln Ser Ser Phe Thr Val Gly Ala Asp Thr Phe Ser
            580                 585                 590

tca ggg aat gaa gtt tat ata gac aga ttt gaa ttg att cca gtt act     1824
Ser Gly Asn Glu Val Tyr Ile Asp Arg Phe Glu Leu Ile Pro Val Thr
        595                 600                 605

gca aca ttt gaa gca gaa tat gat tta gaa aga gca caa aag gcg gtg     1872
Ala Thr Phe Glu Ala Glu Tyr Asp Leu Glu Arg Ala Gln Lys Ala Val
    610                 615                 620

aat gcg ctg ttt act tct ata aac caa ata ggg ata aaa aca gat gtg     1920
Asn Ala Leu Phe Thr Ser Ile Asn Gln Ile Gly Ile Lys Thr Asp Val
625                 630                 635                 640

acg gat tat cat att gat caa gta tcc aat tta gtg gat tgt tta tca     1968
Thr Asp Tyr His Ile Asp Gln Val Ser Asn Leu Val Asp Cys Leu Ser
                645                 650                 655

gat gaa ttt tgt ctg gat gaa aag cga gaa ttg tcc gag aaa gtc aaa     2016
Asp Glu Phe Cys Leu Asp Glu Lys Arg Glu Leu Ser Glu Lys Val Lys
            660                 665                 670

cat gcg aag cga ctc agt gat gag cgg aat tta ctt caa gat cca aac     2064
His Ala Lys Arg Leu Ser Asp Glu Arg Asn Leu Leu Gln Asp Pro Asn
        675                 680                 685

ttc aaa ggc atc aat agg caa cta gac cgt ggt tgg aga gga agt acg     2112
Phe Lys Gly Ile Asn Arg Gln Leu Asp Arg Gly Trp Arg Gly Ser Thr
    690                 695                 700

gat att acc atc caa aga gga gat gac gta ttc aaa gaa aat tat gtc     2160
Asp Ile Thr Ile Gln Arg Gly Asp Asp Val Phe Lys Glu Asn Tyr Val
705                 710                 715                 720

aca cta cca ggt acc ttt gat gag tgc tat cca aca tat ttg tat caa     2208
Thr Leu Pro Gly Thr Phe Asp Glu Cys Tyr Pro Thr Tyr Leu Tyr Gln
                725                 730                 735

aaa atc gat gaa tca aaa tta aaa gcc ttt acc cgt tat caa tta aga     2256
Lys Ile Asp Glu Ser Lys Leu Lys Ala Phe Thr Arg Tyr Gln Leu Arg
            740                 745                 750

ggg tat atc gaa gat agt caa gac tta gaa atc tat tta att cgc tac     2304
Gly Tyr Ile Glu Asp Ser Gln Asp Leu Glu Ile Tyr Leu Ile Arg Tyr
        755                 760                 765

aat gca aaa cat gaa aca gta aat gtg cca ggt acg ggt tcc tta tgg     2352
Asn Ala Lys His Glu Thr Val Asn Val Pro Gly Thr Gly Ser Leu Trp
    770                 775                 780

ccg ctt tca gcc caa agt cca atc gga aag tgt gga gag ccg aat cga     2400
Pro Leu Ser Ala Gln Ser Pro Ile Gly Lys Cys Gly Glu Pro Asn Arg
785                 790                 795                 800

tgc gcg cca cac ctt gaa tgg aat cct gac tta gat tgt tcg tgt agg     2448
Cys Ala Pro His Leu Glu Trp Asn Pro Asp Leu Asp Cys Ser Cys Arg
                805                 810                 815
```

-continued

```
gat gga gaa aag tgt gcc cat cat tcg cat cat ttc tcc tta gac att      2496
Asp Gly Glu Lys Cys Ala His His Ser His His Phe Ser Leu Asp Ile
            820                 825                 830

gat gta gga tgt aca gac tta aat gag gac cta ggt gta tgg gtg atc      2544
Asp Val Gly Cys Thr Asp Leu Asn Glu Asp Leu Gly Val Trp Val Ile
        835                 840                 845

ttt aag att aag acg caa gat ggg cac gca aga cta ggg aat cta gag      2592
Phe Lys Ile Lys Thr Gln Asp Gly His Ala Arg Leu Gly Asn Leu Glu
    850                 855                 860

ttt ctc gaa gag aaa cca tta gta gga gaa gcg cta gct cgt gtg aaa      2640
Phe Leu Glu Glu Lys Pro Leu Val Gly Glu Ala Leu Ala Arg Val Lys
865                 870                 875                 880

aga gcg gag aaa aaa tgg aga gac aaa cgt gaa aaa ttg gaa tgg gaa      2688
Arg Ala Glu Lys Lys Trp Arg Asp Lys Arg Glu Lys Leu Glu Trp Glu
                885                 890                 895

aca aat atc gtt tat aaa gag gca aaa gaa tct gta gat gct tta ttt      2736
Thr Asn Ile Val Tyr Lys Glu Ala Lys Glu Ser Val Asp Ala Leu Phe
            900                 905                 910

gta aac tct caa tat gat caa tta caa gcg gat acg aat att gcc atg      2784
Val Asn Ser Gln Tyr Asp Gln Leu Gln Ala Asp Thr Asn Ile Ala Met
        915                 920                 925

att cat gcg gca gat aaa cgt gtt cat agc att cga gaa gct tat ctg      2832
Ile His Ala Ala Asp Lys Arg Val His Ser Ile Arg Glu Ala Tyr Leu
    930                 935                 940

cct gag ctg tct gtg att ccg ggt gtc aat gcg gct att ttt gaa gaa      2880
Pro Glu Leu Ser Val Ile Pro Gly Val Asn Ala Ala Ile Phe Glu Glu
945                 950                 955                 960

tta gaa ggg cgt att ttc act gca ttc tcc cta tat gat gcg aga aat      2928
Leu Glu Gly Arg Ile Phe Thr Ala Phe Ser Leu Tyr Asp Ala Arg Asn
                965                 970                 975

gtc att aaa aat ggt gat ttt aat aat ggc tta tcc tgc tgg aac gtg      2976
Val Ile Lys Asn Gly Asp Phe Asn Asn Gly Leu Ser Cys Trp Asn Val
            980                 985                 990

aaa ggg cat gta gat gta gaa gaa  caa aac aac caa cgt  tcg gtc ctt    3024
Lys Gly His Val Asp Val Glu Glu  Gln Asn Asn Gln Arg  Ser Val Leu
        995                 1000                1005

gtt gtt  ccg gaa tgg gaa gca  gaa gtg tca caa gaa  gtt cgt gtc       3069
Val Val  Pro Glu Trp Glu Ala  Glu Val Ser Gln Glu  Val Arg Val
    1010                 1015                 1020

tgt ccg  ggt cgt ggc tat atc  ctt cgt gtc aca gcg  tac aag gag       3114
Cys Pro  Gly Arg Gly Tyr Ile  Leu Arg Val Thr Ala  Tyr Lys Glu
    1025                 1030                 1035

gga tat  gga gaa ggt tgc gta  acc att cat gag atc  gag aac aat       3159
Gly Tyr  Gly Glu Gly Cys Val  Thr Ile His Glu Ile  Glu Asn Asn
    1040                 1045                 1050

aca gac  gaa ctg aag ttt agc  aac tgc gta gaa gag  gaa atc tat       3204
Thr Asp  Glu Leu Lys Phe Ser  Asn Cys Val Glu Glu  Glu Ile Tyr
    1055                 1060                 1065

cca aat  aac acg gta acg tgt  aat gat tat act gta  aat caa gaa       3249
Pro Asn  Asn Thr Val Thr Cys  Asn Asp Tyr Thr Val  Asn Gln Glu
    1070                 1075                 1080

gaa tac  gga ggt gcg tac act  tct cgt aat cga gga  tat aac gaa       3294
Glu Tyr  Gly Gly Ala Tyr Thr  Ser Arg Asn Arg Gly  Tyr Asn Glu
    1085                 1090                 1095

gct cct  tcc gta cca gct gat  tat gcg tca gtc tat  gaa gaa aaa       3339
Ala Pro  Ser Val Pro Ala Asp  Tyr Ala Ser Val Tyr  Glu Glu Lys
    1100                 1105                 1110

tcg tat  aca gat gga cga aga  gag aat cct tgt gaa  ttt aac aga       3384
Ser Tyr  Thr Asp Gly Arg Arg  Glu Asn Pro Cys Glu  Phe Asn Arg
    1115                 1120                 1125
```

```
ggg tat  agg gat tac acg cca  cta cca gtt ggt tat  gtg aca aaa      3429
Gly Tyr  Arg Asp Tyr Thr Pro  Leu Pro Val Gly Tyr  Val Thr Lys
    1130                 1135                 1140

gaa tta  gaa tac ttc cca gaa  acc gat aag gta tgg  att gag att      3474
Glu Leu  Glu Tyr Phe Pro Glu  Thr Asp Lys Val Trp  Ile Glu Ile
    1145                 1150                 1155

gga gaa  acg gaa gga aca ttt  atc gtg gac agc gtg  gaa tta ctc      3519
Gly Glu  Thr Glu Gly Thr Phe  Ile Val Asp Ser Val  Glu Leu Leu
    1160                 1165                 1170

ctt atg  gag gaa                                                    3531
Leu Met  Glu Glu
    1175


<210> SEQ ID NO 10
<211> LENGTH: 1177
<212> TYPE: PRT
<213> ORGANISM: Artificial

<400> SEQUENCE: 10

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285
```

-continued

```
Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Thr His Arg Ser Ala Thr Pro Thr Asn
    450                 455                 460

Thr Ile Asp Pro Glu Arg Ile Thr Gln Ile Pro Leu Val Lys Ala His
465                 470                 475                 480

Thr Leu Gln Ser Gly Thr Thr Val Val Arg Gly Pro Gly Phe Thr Gly
                485                 490                 495

Gly Asp Ile Leu Arg Arg Thr Ser Gly Gly Pro Phe Ala Tyr Thr Ile
            500                 505                 510

Val Asn Ile Asn Gly Gln Leu Pro Gln Arg Tyr Arg Ala Arg Ile Arg
        515                 520                 525

Tyr Ala Ser Thr Thr Asn Leu Arg Ile Tyr Val Thr Val Ala Gly Glu
    530                 535                 540

Arg Ile Phe Ala Gly Gln Phe Asn Lys Thr Met Asp Thr Gly Asp Pro
545                 550                 555                 560

Leu Thr Phe Gln Ser Phe Ser Tyr Ala Thr Ile Asn Thr Ala Phe Thr
                565                 570                 575

Phe Pro Met Ser Gln Ser Ser Phe Thr Val Gly Ala Asp Thr Phe Ser
            580                 585                 590

Ser Gly Asn Glu Val Tyr Ile Asp Arg Phe Glu Leu Ile Pro Val Thr
        595                 600                 605

Ala Thr Phe Glu Ala Glu Tyr Asp Leu Glu Arg Ala Gln Lys Ala Val
    610                 615                 620

Asn Ala Leu Phe Thr Ser Ile Asn Gln Ile Gly Ile Lys Thr Asp Val
625                 630                 635                 640

Thr Asp Tyr His Ile Asp Gln Val Ser Asn Leu Val Asp Cys Leu Ser
                645                 650                 655

Asp Glu Phe Cys Leu Asp Glu Lys Arg Glu Leu Ser Glu Lys Val Lys
            660                 665                 670

His Ala Lys Arg Leu Ser Asp Glu Arg Asn Leu Leu Gln Asp Pro Asn
        675                 680                 685

Phe Lys Gly Ile Asn Arg Gln Leu Asp Arg Gly Trp Arg Gly Ser Thr
    690                 695                 700

Asp Ile Thr Ile Gln Arg Gly Asp Asp Val Phe Lys Glu Asn Tyr Val
```

-continued

```
705                 710                 715                 720

Thr Leu Pro Gly Thr Phe Asp Glu Cys Tyr Pro Thr Tyr Leu Tyr Gln
                725                 730                 735

Lys Ile Asp Glu Ser Lys Leu Lys Ala Phe Thr Arg Tyr Gln Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
    770                 775                 780

Pro Leu Ser Ala Gln Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
                805                 810                 815

Asp Gly Glu Lys Cys Ala His His Ser His His Phe Ser Leu Asp Ile
            820                 825                 830

Asp Val Gly Cys Thr Asp Leu Asn Glu Asp Leu Gly Val Trp Val Ile
        835                 840                 845

Phe Lys Ile Lys Thr Gln Asp Gly His Ala Arg Leu Gly Asn Leu Glu
    850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
            900                 905                 910

Val Asn Ser Gln Tyr Asp Gln Leu Gln Ala Asp Thr Asn Ile Ala Met
        915                 920                 925

Ile His Ala Ala Asp Lys Arg Val His Ser Ile Arg Glu Ala Tyr Leu
    930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu  Gln Asn Asn Gln Arg  Ser Val Leu
        995                 1000                1005

Val Val  Pro Glu Trp Glu Ala  Glu Val Ser Gln Glu  Val Arg Val
    1010                 1015                1020

Cys Pro  Gly Arg Gly Tyr Ile  Leu Arg Val Thr Ala  Tyr Lys Glu
    1025                 1030                1035

Gly Tyr  Gly Glu Gly Cys Val  Thr Ile His Glu Ile  Glu Asn Asn
    1040                 1045                1050

Thr Asp  Glu Leu Lys Phe Ser  Asn Cys Val Glu Glu  Glu Ile Tyr
    1055                 1060                1065

Pro Asn  Asn Thr Val Thr Cys  Asn Asp Tyr Thr Val  Asn Gln Glu
    1070                 1075                1080

Glu Tyr  Gly Gly Ala Tyr Thr  Ser Arg Asn Arg Gly  Tyr Asn Glu
    1085                 1090                1095

Ala Pro  Ser Val Pro Ala Asp  Tyr Ala Ser Val Tyr  Glu Glu Lys
    1100                 1105                1110

Ser Tyr  Thr Asp Gly Arg Arg  Glu Asn Pro Cys Glu  Phe Asn Arg
    1115                 1120                1125
```

```
Gly Tyr  Arg Asp Tyr Thr Pro  Leu Pro Val Gly Tyr  Val Thr Lys
    1130                 1135                 1140

Glu Leu  Glu Tyr Phe Pro Glu  Thr Asp Lys Val Trp  Ile Glu Ile
    1145                 1150                 1155

Gly Glu  Thr Glu Gly Thr Phe  Ile Val Asp Ser Val  Glu Leu Leu
    1160                 1165                 1170

Leu Met  Glu Glu
    1175


<210> SEQ ID NO 11
<211> LENGTH: 3531
<212> TYPE: DNA
<213> ORGANISM: Artificial
<220> FEATURE:
<223> OTHER INFORMATION: Description of Artificial Sequence: Synthetic
<221> NAME/KEY: CDS
<222> LOCATION: (1)..(3531)

<400> SEQUENCE: 11

atg gat aac aat ccg aac atc aat gaa tgc att cct tat aat tgt tta       48
Met Asp Asn Asn Pro Asn Ile Asn Glu Cys Ile Pro Tyr Asn Cys Leu
1               5                   10                  15

agt aac cct gaa gta gaa gta tta ggt gga gaa aga ata gaa act ggt       96
Ser Asn Pro Glu Val Glu Val Leu Gly Gly Glu Arg Ile Glu Thr Gly
            20                  25                  30

tac acc cca atc gat att tcc ttg tcg cta acg caa ttt ctt ttg agt      144
Tyr Thr Pro Ile Asp Ile Ser Leu Ser Leu Thr Gln Phe Leu Leu Ser
        35                  40                  45

gaa ttt gtt ccc ggt gct gga ttt gtg tta gga cta gtt gat ata ata      192
Glu Phe Val Pro Gly Ala Gly Phe Val Leu Gly Leu Val Asp Ile Ile
    50                  55                  60

tgg gga att ttt ggt ccc tct caa tgg gac gca ttt ctt gta caa att      240
Trp Gly Ile Phe Gly Pro Ser Gln Trp Asp Ala Phe Leu Val Gln Ile
65                  70                  75                  80

gaa cag tta att aac caa aga ata gaa gaa ttc gct agg aac caa gcc      288
Glu Gln Leu Ile Asn Gln Arg Ile Glu Glu Phe Ala Arg Asn Gln Ala
                85                  90                  95

att tct aga tta gaa gga cta agc aat ctt tat caa att tac gca gaa      336
Ile Ser Arg Leu Glu Gly Leu Ser Asn Leu Tyr Gln Ile Tyr Ala Glu
            100                 105                 110

tct ttt aga gag tgg gaa gca gat cct act aat cca gca tta aga gaa      384
Ser Phe Arg Glu Trp Glu Ala Asp Pro Thr Asn Pro Ala Leu Arg Glu
        115                 120                 125

gag atg cgt att caa ttc aat gac atg aac agt gcc ctt aca acc gct      432
Glu Met Arg Ile Gln Phe Asn Asp Met Asn Ser Ala Leu Thr Thr Ala
    130                 135                 140

att cct ctt ttt gca gtt caa aat tat caa gtt cct ctt tta tca gta      480
Ile Pro Leu Phe Ala Val Gln Asn Tyr Gln Val Pro Leu Leu Ser Val
145                 150                 155                 160

tat gtt caa gct gca aat tta cat tta tca gtt ttg aga gat gtt tca      528
Tyr Val Gln Ala Ala Asn Leu His Leu Ser Val Leu Arg Asp Val Ser
                165                 170                 175

gtg ttt gga caa agg tgg gga ttt gat gcc gcg act atc aat agt cgt      576
Val Phe Gly Gln Arg Trp Gly Phe Asp Ala Ala Thr Ile Asn Ser Arg
            180                 185                 190

tat aat gat tta act agg ctt att ggc aac tat aca gat tat gct gta      624
Tyr Asn Asp Leu Thr Arg Leu Ile Gly Asn Tyr Thr Asp Tyr Ala Val
        195                 200                 205

cgc tgg tac aat acg gga tta gaa cgt gta tgg gga ccg gat tct aga      672
Arg Trp Tyr Asn Thr Gly Leu Glu Arg Val Trp Gly Pro Asp Ser Arg
```

-continued

```
    210                 215                 220

gat tgg gta agg tat aat caa ttt aga aga gaa tta aca cta act gta      720
Asp Trp Val Arg Tyr Asn Gln Phe Arg Arg Glu Leu Thr Leu Thr Val
225                 230                 235                 240

tta gat atc gtt gct ctg ttc ccg aat tat gat agt aga aga tat cca      768
Leu Asp Ile Val Ala Leu Phe Pro Asn Tyr Asp Ser Arg Arg Tyr Pro
                245                 250                 255

att cga aca gtt tcc caa tta aca aga gaa att tat aca aac cca gta      816
Ile Arg Thr Val Ser Gln Leu Thr Arg Glu Ile Tyr Thr Asn Pro Val
            260                 265                 270

tta gaa aat ttt gat ggt agt ttt cga ggc tcg gct cag ggc ata gaa      864
Leu Glu Asn Phe Asp Gly Ser Phe Arg Gly Ser Ala Gln Gly Ile Glu
        275                 280                 285

aga agt att agg agt cca cat ttg atg gat ata ctt aac agt ata acc      912
Arg Ser Ile Arg Ser Pro His Leu Met Asp Ile Leu Asn Ser Ile Thr
    290                 295                 300

atc tat acg gat gct cat agg ggt tat tat tat tgg tca ggg cat caa      960
Ile Tyr Thr Asp Ala His Arg Gly Tyr Tyr Tyr Trp Ser Gly His Gln
305                 310                 315                 320

ata atg gct tct cct gta ggg ttt tcg ggg cca gaa ttc act ttt ccg     1008
Ile Met Ala Ser Pro Val Gly Phe Ser Gly Pro Glu Phe Thr Phe Pro
                325                 330                 335

cta tat gga act atg gga aat gca gct cca caa caa cgt att gtt gct     1056
Leu Tyr Gly Thr Met Gly Asn Ala Ala Pro Gln Gln Arg Ile Val Ala
            340                 345                 350

caa cta ggt cag ggc gtg tat aga aca tta tcg tcc act tta tat aga     1104
Gln Leu Gly Gln Gly Val Tyr Arg Thr Leu Ser Ser Thr Leu Tyr Arg
        355                 360                 365

aga cct ttt aat ata ggg ata aat aat caa caa cta tct gtt ctt gac     1152
Arg Pro Phe Asn Ile Gly Ile Asn Asn Gln Gln Leu Ser Val Leu Asp
    370                 375                 380

ggg aca gaa ttt gct tat gga acc tcc tca aat ttg cca tcc gct gta     1200
Gly Thr Glu Phe Ala Tyr Gly Thr Ser Ser Asn Leu Pro Ser Ala Val
385                 390                 395                 400

tac aga aaa agc gga acg gta gat tcg ctg gat gaa ata ccg cca cag     1248
Tyr Arg Lys Ser Gly Thr Val Asp Ser Leu Asp Glu Ile Pro Pro Gln
                405                 410                 415

aat aac aac gtg cca cct agg caa gga ttt agt cat cga tta agc cat     1296
Asn Asn Asn Val Pro Pro Arg Gln Gly Phe Ser His Arg Leu Ser His
            420                 425                 430

gtt tca atg ttt cgt tca ggc ttt agt aat agt agt gta agt ata ata     1344
Val Ser Met Phe Arg Ser Gly Phe Ser Asn Ser Ser Val Ser Ile Ile
        435                 440                 445

aga gct cca atg ttt tct tgg acg cac cgt agt gca acc cct aca aat     1392
Arg Ala Pro Met Phe Ser Trp Thr His Arg Ser Ala Thr Pro Thr Asn
    450                 455                 460

aca att gat ccg gag agg att act caa ata cca ttg gta aaa gca cat     1440
Thr Ile Asp Pro Glu Arg Ile Thr Gln Ile Pro Leu Val Lys Ala His
465                 470                 475                 480

aca ctt cag tca ggt act act gtt gta aga ggg ccc ggg ttt acg gga     1488
Thr Leu Gln Ser Gly Thr Thr Val Val Arg Gly Pro Gly Phe Thr Gly
                485                 490                 495

gga gat att ctt cga cga aca agt gga gga cca ttt gct tat act att     1536
Gly Asp Ile Leu Arg Arg Thr Ser Gly Gly Pro Phe Ala Tyr Thr Ile
            500                 505                 510

gtt aat ata aat ggg caa tta ccc caa agg tat cgt gca aga ata cgc     1584
Val Asn Ile Asn Gly Gln Leu Pro Gln Arg Tyr Arg Ala Arg Ile Arg
        515                 520                 525

tat gcc tct act aca aat cta aga att tac gta acg gtt gca ggt gaa     1632
```

-continued

```
Tyr Ala Ser Thr Thr Asn Leu Arg Ile Tyr Val Thr Val Ala Gly Glu
    530                 535                 540

cgg att ttt gct ggt caa ttt aac aaa aca atg gat acc ggt gac cca     1680
Arg Ile Phe Ala Gly Gln Phe Asn Lys Thr Met Asp Thr Gly Asp Pro
545                 550                 555                 560

tta aca ttc caa tct ttt agt tac gca act att aat aca gct ttt aca     1728
Leu Thr Phe Gln Ser Phe Ser Tyr Ala Thr Ile Asn Thr Ala Phe Thr
                565                 570                 575

ttc cca atg agc cag agt agt ttc aca gta ggt gct gat act ttt agt     1776
Phe Pro Met Ser Gln Ser Ser Phe Thr Val Gly Ala Asp Thr Phe Ser
            580                 585                 590

tca ggg aat gaa gtt tat ata gac aga ttt gaa ttg att cca gtt act     1824
Ser Gly Asn Glu Val Tyr Ile Asp Arg Phe Glu Leu Ile Pro Val Thr
        595                 600                 605

gca aca ctc gag gct gaa tat aat ctg gaa aga gcg cag aag gcg gtg     1872
Ala Thr Leu Glu Ala Glu Tyr Asn Leu Glu Arg Ala Gln Lys Ala Val
    610                 615                 620

aat gcg ctg ttt acg tct aca aac caa cta ggg cta aaa aca aat gta     1920
Asn Ala Leu Phe Thr Ser Thr Asn Gln Leu Gly Leu Lys Thr Asn Val
625                 630                 635                 640

acg gat tat cat att gat caa gtg tcc aat tta gtt acg tat tta tcg     1968
Thr Asp Tyr His Ile Asp Gln Val Ser Asn Leu Val Thr Tyr Leu Ser
                645                 650                 655

gat gaa ttt tgt ctg gat gaa aag cga gaa ttg tcc gag aaa gtc aaa     2016
Asp Glu Phe Cys Leu Asp Glu Lys Arg Glu Leu Ser Glu Lys Val Lys
            660                 665                 670

cat gcg aag cga ctc agt gat gaa cgc aat tta ctc caa gat tca aat     2064
His Ala Lys Arg Leu Ser Asp Glu Arg Asn Leu Leu Gln Asp Ser Asn
        675                 680                 685

ttc aaa gac att aat agg caa cca gaa cgt ggg tgg ggc gga agt aca     2112
Phe Lys Asp Ile Asn Arg Gln Pro Glu Arg Gly Trp Gly Gly Ser Thr
    690                 695                 700

ggg att acc atc caa gga ggg gat gac gta ttt aaa gaa aat tac gtc     2160
Gly Ile Thr Ile Gln Gly Gly Asp Asp Val Phe Lys Glu Asn Tyr Val
705                 710                 715                 720

aca cta tca ggt acc ttt gat gag tgc tat cca aca tat ttg tat caa     2208
Thr Leu Ser Gly Thr Phe Asp Glu Cys Tyr Pro Thr Tyr Leu Tyr Gln
                725                 730                 735

aaa atc gat gaa tca aaa tta aaa gcc ttt acc cgt tat caa tta aga     2256
Lys Ile Asp Glu Ser Lys Leu Lys Ala Phe Thr Arg Tyr Gln Leu Arg
            740                 745                 750

ggg tat atc gaa gat agt caa gac tta gaa atc tat tta att cgc tac     2304
Gly Tyr Ile Glu Asp Ser Gln Asp Leu Glu Ile Tyr Leu Ile Arg Tyr
        755                 760                 765

aat gca aaa cat gaa aca gta aat gtg cca ggt acg ggt tcc tta tgg     2352
Asn Ala Lys His Glu Thr Val Asn Val Pro Gly Thr Gly Ser Leu Trp
    770                 775                 780

ccg ctt tca gcc caa agt cca atc gga aag tgt gga gag ccg aat cga     2400
Pro Leu Ser Ala Gln Ser Pro Ile Gly Lys Cys Gly Glu Pro Asn Arg
785                 790                 795                 800

tgc gcg cca cac ctt gaa tgg aat cct gac tta gat tgt tcg tgt agg     2448
Cys Ala Pro His Leu Glu Trp Asn Pro Asp Leu Asp Cys Ser Cys Arg
                805                 810                 815

gat gga gaa aag tgt gcc cat cat tcg cat cat ttc tcc tta gac att     2496
Asp Gly Glu Lys Cys Ala His His Ser His His Phe Ser Leu Asp Ile
            820                 825                 830

gat gta gga tgt aca gac tta aat gag gac cta ggt gta tgg gtg atc     2544
Asp Val Gly Cys Thr Asp Leu Asn Glu Asp Leu Gly Val Trp Val Ile
        835                 840                 845
```

-continued

```
ttt aag att aag acg caa gat ggg cac gca aga cta ggg aat cta gag      2592
Phe Lys Ile Lys Thr Gln Asp Gly His Ala Arg Leu Gly Asn Leu Glu
    850                 855                 860

ttt ctc gaa gag aaa cca tta gta gga gaa gcg cta gct cgt gtg aaa      2640
Phe Leu Glu Glu Lys Pro Leu Val Gly Glu Ala Leu Ala Arg Val Lys
865                 870                 875                 880

aga gcg gag aaa aaa tgg aga gac aaa cgt gaa aaa ttg gaa tgg gaa      2688
Arg Ala Glu Lys Lys Trp Arg Asp Lys Arg Glu Lys Leu Glu Trp Glu
                885                 890                 895

aca aat atc gtt tat aaa gag gca aaa gaa tct gta gat gct tta ttt      2736
Thr Asn Ile Val Tyr Lys Glu Ala Lys Glu Ser Val Asp Ala Leu Phe
            900                 905                 910

gta aac tct caa tat gat caa tta caa gcg gat acg aat att gcc atg      2784
Val Asn Ser Gln Tyr Asp Gln Leu Gln Ala Asp Thr Asn Ile Ala Met
        915                 920                 925

att cat gcg gca gat aaa cgt gtt cat agc att cga gaa gct tat ctg      2832
Ile His Ala Ala Asp Lys Arg Val His Ser Ile Arg Glu Ala Tyr Leu
    930                 935                 940

cct gag ctg tct gtg att ccg ggt gtc aat gcg gct att ttt gaa gaa      2880
Pro Glu Leu Ser Val Ile Pro Gly Val Asn Ala Ala Ile Phe Glu Glu
945                 950                 955                 960

tta gaa ggg cgt att ttc act gca ttc tcc cta tat gat gcg aga aat      2928
Leu Glu Gly Arg Ile Phe Thr Ala Phe Ser Leu Tyr Asp Ala Arg Asn
                965                 970                 975

gtc att aaa aat ggt gat ttt aat aat ggc tta tcc tgc tgg aac gtg      2976
Val Ile Lys Asn Gly Asp Phe Asn Asn Gly Leu Ser Cys Trp Asn Val
            980                 985                 990

aaa ggg cat gta gat gta gaa gaa  caa aac aac caa cgt  tcg gtc ctt    3024
Lys Gly His Val Asp Val Glu Glu  Gln Asn Asn Gln Arg  Ser Val Leu
        995                 1000                1005

gtt gtt  ccg gaa tgg gaa gca  gaa gtg tca caa gaa  gtt cgt gtc      3069
Val Val  Pro Glu Trp Glu Ala  Glu Val Ser Gln Glu  Val Arg Val
    1010                1015                1020

tgt ccg  ggt cgt ggc tat atc  ctt cgt gtc aca gcg  tac aag gag      3114
Cys Pro  Gly Arg Gly Tyr Ile  Leu Arg Val Thr Ala  Tyr Lys Glu
    1025                1030                1035

gga tat  gga gaa ggt tgc gta  acc att cat gag atc  gag aac aat      3159
Gly Tyr  Gly Glu Gly Cys Val  Thr Ile His Glu Ile  Glu Asn Asn
    1040                1045                1050

aca gac  gaa ctg aag ttt agc  aac tgc gta gaa gag  gaa atc tat      3204
Thr Asp  Glu Leu Lys Phe Ser  Asn Cys Val Glu Glu  Glu Ile Tyr
    1055                1060                1065

cca aat  aac acg gta acg tgt  aat gat tat act gta  aat caa gaa      3249
Pro Asn  Asn Thr Val Thr Cys  Asn Asp Tyr Thr Val  Asn Gln Glu
    1070                1075                1080

gaa tac  gga ggt gcg tac act  tct cgt aat cga gga  tat aac gaa      3294
Glu Tyr  Gly Gly Ala Tyr Thr  Ser Arg Asn Arg Gly  Tyr Asn Glu
    1085                1090                1095

gct cct  tcc gta cca gct gat  tat gcg tca gtc tat  gaa gaa aaa      3339
Ala Pro  Ser Val Pro Ala Asp  Tyr Ala Ser Val Tyr  Glu Glu Lys
    1100                1105                1110

tcg tat  aca gat gga cga aga  gag aat cct tgt gaa  ttt aac aga      3384
Ser Tyr  Thr Asp Gly Arg Arg  Glu Asn Pro Cys Glu  Phe Asn Arg
    1115                1120                1125

ggg tat  agg gat tac acg cca  cta cca gtt ggt tat  gtg aca aaa      3429
Gly Tyr  Arg Asp Tyr Thr Pro  Leu Pro Val Gly Tyr  Val Thr Lys
    1130                1135                1140

gaa tta  gaa tac ttc cca gaa  acc gat aag gta tgg  att gag att      3474
Glu Leu  Glu Tyr Phe Pro Glu  Thr Asp Lys Val Trp  Ile Glu Ile
    1145                1150                1155
```

```
gga gaa  acg gaa gga aca ttt  atc gtg gac agc gtg  gaa tta ctc      3519
Gly Glu  Thr Glu Gly Thr Phe  Ile Val Asp Ser Val  Glu Leu Leu
    1160                 1165                 1170

ctt atg  gag gaa                                                     3531
Leu Met  Glu Glu
    1175


<210> SEQ ID NO 12
<211> LENGTH: 1177
<212> TYPE: PRT
<213> ORGANISM: Artificial

<400> SEQUENCE: 12

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335
```

-continued

```
Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Thr His Arg Ser Ala Thr Pro Thr Asn
    450                 455                 460

Thr Ile Asp Pro Glu Arg Ile Thr Gln Ile Pro Leu Val Lys Ala His
465                 470                 475                 480

Thr Leu Gln Ser Gly Thr Thr Val Val Arg Gly Pro Gly Phe Thr Gly
                485                 490                 495

Gly Asp Ile Leu Arg Arg Thr Ser Gly Gly Pro Phe Ala Tyr Thr Ile
            500                 505                 510

Val Asn Ile Asn Gly Gln Leu Pro Gln Arg Tyr Arg Ala Arg Ile Arg
        515                 520                 525

Tyr Ala Ser Thr Thr Asn Leu Arg Ile Tyr Val Thr Val Ala Gly Glu
    530                 535                 540

Arg Ile Phe Ala Gly Gln Phe Asn Lys Thr Met Asp Thr Gly Asp Pro
545                 550                 555                 560

Leu Thr Phe Gln Ser Phe Ser Tyr Ala Thr Ile Asn Thr Ala Phe Thr
                565                 570                 575

Phe Pro Met Ser Gln Ser Ser Phe Thr Val Gly Ala Asp Thr Phe Ser
            580                 585                 590

Ser Gly Asn Glu Val Tyr Ile Asp Arg Phe Glu Leu Ile Pro Val Thr
        595                 600                 605

Ala Thr Leu Glu Ala Glu Tyr Asn Leu Glu Arg Ala Gln Lys Ala Val
    610                 615                 620

Asn Ala Leu Phe Thr Ser Thr Asn Gln Leu Gly Leu Lys Thr Asn Val
625                 630                 635                 640

Thr Asp Tyr His Ile Asp Gln Val Ser Asn Leu Val Thr Tyr Leu Ser
                645                 650                 655

Asp Glu Phe Cys Leu Asp Glu Lys Arg Glu Leu Ser Glu Lys Val Lys
            660                 665                 670

His Ala Lys Arg Leu Ser Asp Glu Arg Asn Leu Leu Gln Asp Ser Asn
        675                 680                 685

Phe Lys Asp Ile Asn Arg Gln Pro Glu Arg Gly Trp Gly Gly Ser Thr
    690                 695                 700

Gly Ile Thr Ile Gln Gly Gly Asp Asp Val Phe Lys Glu Asn Tyr Val
705                 710                 715                 720

Thr Leu Ser Gly Thr Phe Asp Glu Cys Tyr Pro Thr Tyr Leu Tyr Gln
                725                 730                 735

Lys Ile Asp Glu Ser Lys Leu Lys Ala Phe Thr Arg Tyr Gln Leu Arg
            740                 745                 750
```

-continued

```
Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
    770                 775                 780

Pro Leu Ser Ala Gln Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
                805                 810                 815

Asp Gly Glu Lys Cys Ala His His Ser His His Phe Ser Leu Asp Ile
            820                 825                 830

Asp Val Gly Cys Thr Asp Leu Asn Glu Asp Leu Gly Val Trp Val Ile
        835                 840                 845

Phe Lys Ile Lys Thr Gln Asp Gly His Ala Arg Leu Gly Asn Leu Glu
    850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
            900                 905                 910

Val Asn Ser Gln Tyr Asp Gln Leu Gln Ala Asp Thr Asn Ile Ala Met
        915                 920                 925

Ile His Ala Ala Asp Lys Arg Val His Ser Ile Arg Glu Ala Tyr Leu
    930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu  Gln Asn Asn Gln Arg  Ser Val Leu
        995                 1000                 1005

Val Val  Pro Glu Trp Glu Ala  Glu Val Ser Gln Glu  Val Arg Val
    1010                 1015                 1020

Cys Pro  Gly Arg Gly Tyr Ile  Leu Arg Val Thr Ala  Tyr Lys Glu
    1025                 1030                 1035

Gly Tyr  Gly Glu Gly Cys Val  Thr Ile His Glu Ile  Glu Asn Asn
    1040                 1045                 1050

Thr Asp  Glu Leu Lys Phe Ser  Asn Cys Val Glu Glu  Glu Ile Tyr
    1055                 1060                 1065

Pro Asn  Asn Thr Val Thr Cys  Asn Asp Tyr Thr Val  Asn Gln Glu
    1070                 1075                 1080

Glu Tyr  Gly Gly Ala Tyr Thr  Ser Arg Asn Arg Gly  Tyr Asn Glu
    1085                 1090                 1095

Ala Pro  Ser Val Pro Ala Asp  Tyr Ala Ser Val Tyr  Glu Glu Lys
    1100                 1105                 1110

Ser Tyr  Thr Asp Gly Arg Arg  Glu Asn Pro Cys Glu  Phe Asn Arg
    1115                 1120                 1125

Gly Tyr  Arg Asp Tyr Thr Pro  Leu Pro Val Gly Tyr  Val Thr Lys
    1130                 1135                 1140

Glu Leu  Glu Tyr Phe Pro Glu  Thr Asp Lys Val Trp  Ile Glu Ile
    1145                 1150                 1155

Gly Glu  Thr Glu Gly Thr Phe  Ile Val Asp Ser Val  Glu Leu Leu
```

-continued

```
    1160                1165                1170

Leu Met  Glu Glu
    1175


<210> SEQ ID NO 13
<211> LENGTH: 3531
<212> TYPE: DNA
<213> ORGANISM: Artificial
<220> FEATURE:
<223> OTHER INFORMATION: Description of Artificial Sequence: Synthetic
<221> NAME/KEY: CDS
<222> LOCATION: (1)..(3531)

<400> SEQUENCE: 13

atg gat aac aat ccg aac atc aat gaa tgc att cct tat aat tgt tta       48
Met Asp Asn Asn Pro Asn Ile Asn Glu Cys Ile Pro Tyr Asn Cys Leu
1               5                   10                  15

agt aac cct gaa gta gaa gta tta ggt gga gaa aga ata gaa act ggt       96
Ser Asn Pro Glu Val Glu Val Leu Gly Gly Glu Arg Ile Glu Thr Gly
            20                  25                  30

tac acc cca atc gat att tcc ttg tcg cta acg caa ttt ctt ttg agt      144
Tyr Thr Pro Ile Asp Ile Ser Leu Ser Leu Thr Gln Phe Leu Leu Ser
        35                  40                  45

gaa ttt gtt ccc ggt gct gga ttt gtg tta gga cta gtt gat ata ata      192
Glu Phe Val Pro Gly Ala Gly Phe Val Leu Gly Leu Val Asp Ile Ile
    50                  55                  60

tgg gga att ttt ggt ccc tct caa tgg gac gca ttt ctt gta caa att      240
Trp Gly Ile Phe Gly Pro Ser Gln Trp Asp Ala Phe Leu Val Gln Ile
65                  70                  75                  80

gaa cag tta att aac caa aga ata gaa gaa ttc gct agg aac caa gcc      288
Glu Gln Leu Ile Asn Gln Arg Ile Glu Glu Phe Ala Arg Asn Gln Ala
                85                  90                  95

att tct aga tta gaa gga cta agc aat ctt tat caa att tac gca gaa      336
Ile Ser Arg Leu Glu Gly Leu Ser Asn Leu Tyr Gln Ile Tyr Ala Glu
            100                 105                 110

tct ttt aga gag tgg gaa gca gat cct act aat cca gca tta aga gaa      384
Ser Phe Arg Glu Trp Glu Ala Asp Pro Thr Asn Pro Ala Leu Arg Glu
        115                 120                 125

gag atg cgt att caa ttc aat gac atg aac agt gcc ctt aca acc gct      432
Glu Met Arg Ile Gln Phe Asn Asp Met Asn Ser Ala Leu Thr Thr Ala
    130                 135                 140

att cct ctt ttt gca gtt caa aat tat caa gtt cct ctt tta tca gta      480
Ile Pro Leu Phe Ala Val Gln Asn Tyr Gln Val Pro Leu Leu Ser Val
145                 150                 155                 160

tat gtt caa gct gca aat tta cat tta tca gtt ttg aga gat gtt tca      528
Tyr Val Gln Ala Ala Asn Leu His Leu Ser Val Leu Arg Asp Val Ser
                165                 170                 175

gtg ttt gga caa agg tgg gga ttt gat gcc gcg act atc aat agt cgt      576
Val Phe Gly Gln Arg Trp Gly Phe Asp Ala Ala Thr Ile Asn Ser Arg
            180                 185                 190

tat aat gat tta act agg ctt att ggc aac tat aca gat cat gct gta      624
Tyr Asn Asp Leu Thr Arg Leu Ile Gly Asn Tyr Thr Asp His Ala Val
        195                 200                 205

cgc tgg tac aat acg gga tta gag cgt gta tgg gga ccg gat tct aga      672
Arg Trp Tyr Asn Thr Gly Leu Glu Arg Val Trp Gly Pro Asp Ser Arg
    210                 215                 220

gat tgg ata aga tat aat caa ttt aga aga gaa tta aca cta act gta      720
Asp Trp Ile Arg Tyr Asn Gln Phe Arg Arg Glu Leu Thr Leu Thr Val
225                 230                 235                 240

tta gat atc gtt tct cta ttt ccg aac tat gat agt aga acg tat cca      768
Leu Asp Ile Val Ser Leu Phe Pro Asn Tyr Asp Ser Arg Thr Tyr Pro
```

-continued

```
            245                 250                 255

att cga aca gtt tcc caa tta aca aga gaa att tat aca aac cca gta      816
Ile Arg Thr Val Ser Gln Leu Thr Arg Glu Ile Tyr Thr Asn Pro Val
        260                 265                 270

tta gaa aat ttt gat ggt agt ttt cga ggc tcg gct cag ggc ata gaa      864
Leu Glu Asn Phe Asp Gly Ser Phe Arg Gly Ser Ala Gln Gly Ile Glu
    275                 280                 285

gga agt att agg agt cca cat ttg atg gat ata ctt aac agt ata acc      912
Gly Ser Ile Arg Ser Pro His Leu Met Asp Ile Leu Asn Ser Ile Thr
290                 295                 300

atc tat acg gat gct cat aga gga gaa tat tat tgg tca ggg cat caa      960
Ile Tyr Thr Asp Ala His Arg Gly Glu Tyr Tyr Trp Ser Gly His Gln
305                 310                 315                 320

ata atg gct tct cct gta ggg ttt tcg ggg cca gaa ttc act ttt ccg     1008
Ile Met Ala Ser Pro Val Gly Phe Ser Gly Pro Glu Phe Thr Phe Pro
                325                 330                 335

cta tat gga act atg gga aat gca gct cca caa caa cgt att gtt gct     1056
Leu Tyr Gly Thr Met Gly Asn Ala Ala Pro Gln Gln Arg Ile Val Ala
            340                 345                 350

caa cta ggt cag ggc gtg tat aga aca tta tcg tcc act tta tat aga     1104
Gln Leu Gly Gln Gly Val Tyr Arg Thr Leu Ser Ser Thr Leu Tyr Arg
        355                 360                 365

aga cct ttt aat ata ggg ata aat aat caa caa cta tct gtt ctt gac     1152
Arg Pro Phe Asn Ile Gly Ile Asn Asn Gln Gln Leu Ser Val Leu Asp
    370                 375                 380

ggg aca gaa ttt gct tat gga acc tcc tca aat ttg cca tcc gct gta     1200
Gly Thr Glu Phe Ala Tyr Gly Thr Ser Ser Asn Leu Pro Ser Ala Val
385                 390                 395                 400

tac aga aaa agc gga acg gta gat tcg ctg gat gaa ata ccg cca cag     1248
Tyr Arg Lys Ser Gly Thr Val Asp Ser Leu Asp Glu Ile Pro Pro Gln
                405                 410                 415

aat aac aac gtg cca cct agg caa gga ttt agt cat cga tta agc cat     1296
Asn Asn Asn Val Pro Pro Arg Gln Gly Phe Ser His Arg Leu Ser His
            420                 425                 430

gtt tca atg ttt cgt tca ggc ttt agt aat agt agt gta agt ata ata     1344
Val Ser Met Phe Arg Ser Gly Phe Ser Asn Ser Ser Val Ser Ile Ile
        435                 440                 445

aga gct cca atg ttt tct tgg acg cac cgt agt gca acc cct aca aat     1392
Arg Ala Pro Met Phe Ser Trp Thr His Arg Ser Ala Thr Pro Thr Asn
    450                 455                 460

aca att gat ccg gag agg att act caa ata cca ttg gta aaa gca cat     1440
Thr Ile Asp Pro Glu Arg Ile Thr Gln Ile Pro Leu Val Lys Ala His
465                 470                 475                 480

aca ctt cag tca ggt act act gtt gta aga ggg ccc ggg ttt acg gga     1488
Thr Leu Gln Ser Gly Thr Thr Val Val Arg Gly Pro Gly Phe Thr Gly
                485                 490                 495

gga gat att ctt cga cga aca agt gga gga cca ttt gct tat act att     1536
Gly Asp Ile Leu Arg Arg Thr Ser Gly Gly Pro Phe Ala Tyr Thr Ile
            500                 505                 510

gtt aat ata aat ggg caa tta ccc caa agg tat cgt gca aga ata cgc     1584
Val Asn Ile Asn Gly Gln Leu Pro Gln Arg Tyr Arg Ala Arg Ile Arg
        515                 520                 525

tat gcc tct act aca aat cta aga att tac gta acg gtt gca ggt gaa     1632
Tyr Ala Ser Thr Thr Asn Leu Arg Ile Tyr Val Thr Val Ala Gly Glu
    530                 535                 540

cgg att ttt gct ggt caa ttt aac aaa aca atg gat acc ggt gac cca     1680
Arg Ile Phe Ala Gly Gln Phe Asn Lys Thr Met Asp Thr Gly Asp Pro
545                 550                 555                 560

tta aca ttc caa tct ttt agt tac gca act att aat aca gct ttt aca     1728
```

-continued

```
Leu Thr Phe Gln Ser Phe Ser Tyr Ala Thr Ile Asn Thr Ala Phe Thr
                565                 570                 575

ttc cca atg agc cag agt agt ttc aca gta ggt gct gat act ttt agt     1776
Phe Pro Met Ser Gln Ser Ser Phe Thr Val Gly Ala Asp Thr Phe Ser
            580                 585                 590

tca ggg aat gaa gtt tat ata gac aga ttt gaa ttg att cca gtt act     1824
Ser Gly Asn Glu Val Tyr Ile Asp Arg Phe Glu Leu Ile Pro Val Thr
        595                 600                 605

gca aca ttt gaa gca gaa tat gat tta gaa aga gca caa aag gcg gtg     1872
Ala Thr Phe Glu Ala Glu Tyr Asp Leu Glu Arg Ala Gln Lys Ala Val
    610                 615                 620

aat gcg ctg ttt act tct ata aac caa ata ggg ata aaa aca gat gtg     1920
Asn Ala Leu Phe Thr Ser Ile Asn Gln Ile Gly Ile Lys Thr Asp Val
625                 630                 635                 640

acg gat tat cat att gat caa gta tcc aat tta gtg gat tgt tta tca     1968
Thr Asp Tyr His Ile Asp Gln Val Ser Asn Leu Val Asp Cys Leu Ser
                645                 650                 655

gat gaa ttt tgt ctg gat gaa aag cga gaa ttg tcc gag aaa gtc aaa     2016
Asp Glu Phe Cys Leu Asp Glu Lys Arg Glu Leu Ser Glu Lys Val Lys
            660                 665                 670

cat gcg aag cga ctc agt gat gag cgg aat tta ctt caa gat cca aac     2064
His Ala Lys Arg Leu Ser Asp Glu Arg Asn Leu Leu Gln Asp Pro Asn
        675                 680                 685

ttc aaa ggc atc aat agg caa cta gac cgt ggt tgg aga gga agt acg     2112
Phe Lys Gly Ile Asn Arg Gln Leu Asp Arg Gly Trp Arg Gly Ser Thr
    690                 695                 700

gat att acc atc caa aga gga gat gac gta ttc aaa gaa aat tat gtc     2160
Asp Ile Thr Ile Gln Arg Gly Asp Asp Val Phe Lys Glu Asn Tyr Val
705                 710                 715                 720

aca cta cca ggt acc ttt gat gag tgc tat cca aca tat ttg tat caa     2208
Thr Leu Pro Gly Thr Phe Asp Glu Cys Tyr Pro Thr Tyr Leu Tyr Gln
                725                 730                 735

aaa atc gat gaa tca aaa tta aaa gcc ttt acc cgt tat caa tta aga     2256
Lys Ile Asp Glu Ser Lys Leu Lys Ala Phe Thr Arg Tyr Gln Leu Arg
            740                 745                 750

ggg tat atc gaa gat agt caa gac tta gaa atc tat tta att cgc tac     2304
Gly Tyr Ile Glu Asp Ser Gln Asp Leu Glu Ile Tyr Leu Ile Arg Tyr
        755                 760                 765

aat gca aaa cat gaa aca gta aat gtg cca ggt acg ggt tcc tta tgg     2352
Asn Ala Lys His Glu Thr Val Asn Val Pro Gly Thr Gly Ser Leu Trp
    770                 775                 780

ccg ctt tca gcc caa agt cca atc gga aag tgt gga gag ccg aat cga     2400
Pro Leu Ser Ala Gln Ser Pro Ile Gly Lys Cys Gly Glu Pro Asn Arg
785                 790                 795                 800

tgc gcg cca cac ctt gaa tgg aat cct gac tta gat tgt tcg tgt agg     2448
Cys Ala Pro His Leu Glu Trp Asn Pro Asp Leu Asp Cys Ser Cys Arg
                805                 810                 815

gat gga gaa aag tgt gcc cat cat tcg cat cat ttc tcc tta gac att     2496
Asp Gly Glu Lys Cys Ala His His Ser His His Phe Ser Leu Asp Ile
            820                 825                 830

gat gta gga tgt aca gac tta aat gag gac cta ggt gta tgg gtg atc     2544
Asp Val Gly Cys Thr Asp Leu Asn Glu Asp Leu Gly Val Trp Val Ile
        835                 840                 845

ttt aag att aag acg caa gat ggg cac gca aga cta ggg aat cta gag     2592
Phe Lys Ile Lys Thr Gln Asp Gly His Ala Arg Leu Gly Asn Leu Glu
    850                 855                 860

ttt ctc gaa gag aaa cca tta gta gga gaa gcg cta gct cgt gtg aaa     2640
Phe Leu Glu Glu Lys Pro Leu Val Gly Glu Ala Leu Ala Arg Val Lys
865                 870                 875                 880
```

-continued

```
aga gcg gag aaa aaa tgg aga gac aaa cgt gaa aaa ttg gaa tgg gaa     2688
Arg Ala Glu Lys Lys Trp Arg Asp Lys Arg Glu Lys Leu Glu Trp Glu
            885                 890                 895

aca aat atc gtt tat aaa gag gca aaa gaa tct gta gat gct tta ttt     2736
Thr Asn Ile Val Tyr Lys Glu Ala Lys Glu Ser Val Asp Ala Leu Phe
            900                 905                 910

gta aac tct caa tat gat caa tta caa gcg gat acg aat att gcc atg     2784
Val Asn Ser Gln Tyr Asp Gln Leu Gln Ala Asp Thr Asn Ile Ala Met
        915                 920                 925

att cat gcg gca gat aaa cgt gtt cat agc att cga gaa gct tat ctg     2832
Ile His Ala Ala Asp Lys Arg Val His Ser Ile Arg Glu Ala Tyr Leu
    930                 935                 940

cct gag ctg tct gtg att ccg ggt gtc aat gcg gct att ttt gaa gaa     2880
Pro Glu Leu Ser Val Ile Pro Gly Val Asn Ala Ala Ile Phe Glu Glu
945                 950                 955                 960

tta gaa ggg cgt att ttc act gca ttc tcc cta tat gat gcg aga aat     2928
Leu Glu Gly Arg Ile Phe Thr Ala Phe Ser Leu Tyr Asp Ala Arg Asn
            965                 970                 975

gtc att aaa aat ggt gat ttt aat aat ggc tta tcc tgc tgg aac gtg     2976
Val Ile Lys Asn Gly Asp Phe Asn Asn Gly Leu Ser Cys Trp Asn Val
            980                 985                 990

aaa ggg cat gta gat gta gaa gaa  caa aac aac caa cgt  tcg gtc ctt   3024
Lys Gly His Val Asp Val Glu Glu  Gln Asn Asn Gln Arg  Ser Val Leu
        995                 1000                 1005

gtt gtt  ccg gaa tgg gaa gca  gaa gtg tca caa gaa  gtt cgt gtc      3069
Val Val  Pro Glu Trp Glu Ala  Glu Val Ser Gln Glu  Val Arg Val
    1010                 1015                 1020

tgt ccg  ggt cgt ggc tat atc  ctt cgt gtc aca gcg  tac aag gag      3114
Cys Pro  Gly Arg Gly Tyr Ile  Leu Arg Val Thr Ala  Tyr Lys Glu
    1025                 1030                 1035

gga tat  gga gaa ggt tgc gta  acc att cat gag atc  gag aac aat      3159
Gly Tyr  Gly Glu Gly Cys Val  Thr Ile His Glu Ile  Glu Asn Asn
    1040                 1045                 1050

aca gac  gaa ctg aag ttt agc  aac tgc gta gaa gag  gaa atc tat      3204
Thr Asp  Glu Leu Lys Phe Ser  Asn Cys Val Glu Glu  Glu Ile Tyr
    1055                 1060                 1065

cca aat  aac acg gta acg tgt  aat gat tat act gta  aat caa gaa      3249
Pro Asn  Asn Thr Val Thr Cys  Asn Asp Tyr Thr Val  Asn Gln Glu
    1070                 1075                 1080

gaa tac  gga ggt gcg tac act  tct cgt aat cga gga  tat aac gaa      3294
Glu Tyr  Gly Gly Ala Tyr Thr  Ser Arg Asn Arg Gly  Tyr Asn Glu
    1085                 1090                 1095

gct cct  tcc gta cca gct gat  tat gcg tca gtc tat  gaa gaa aaa      3339
Ala Pro  Ser Val Pro Ala Asp  Tyr Ala Ser Val Tyr  Glu Glu Lys
    1100                 1105                 1110

tcg tat  aca gat gga cga aga  gag aat cct tgt gaa  ttt aac aga      3384
Ser Tyr  Thr Asp Gly Arg Arg  Glu Asn Pro Cys Glu  Phe Asn Arg
    1115                 1120                 1125

ggg tat  agg gat tac acg cca  cta cca gtt ggt tat  gtg aca aaa      3429
Gly Tyr  Arg Asp Tyr Thr Pro  Leu Pro Val Gly Tyr  Val Thr Lys
    1130                 1135                 1140

gaa tta  gaa tac ttc cca gaa  acc gat aag gta tgg  att gag att      3474
Glu Leu  Glu Tyr Phe Pro Glu  Thr Asp Lys Val Trp  Ile Glu Ile
    1145                 1150                 1155

gga gaa  acg gaa gga aca ttt  atc gtg gac agc gtg  gaa tta ctc      3519
Gly Glu  Thr Glu Gly Thr Phe  Ile Val Asp Ser Val  Glu Leu Leu
    1160                 1165                 1170

ctt atg  gag gaa                                                    3531
Leu Met  Glu Glu
    1175
```

<210> SEQ ID NO 14
<211> LENGTH: 1177
<212> TYPE: PRT
<213> ORGANISM: Artificial

<400> SEQUENCE: 14

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
```

-continued

```
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Thr His Arg Ser Ala Thr Pro Thr Asn
    450                 455                 460

Thr Ile Asp Pro Glu Arg Ile Thr Gln Ile Pro Leu Val Lys Ala His
465                 470                 475                 480

Thr Leu Gln Ser Gly Thr Thr Val Val Arg Gly Pro Gly Phe Thr Gly
                485                 490                 495

Gly Asp Ile Leu Arg Arg Thr Ser Gly Gly Pro Phe Ala Tyr Thr Ile
            500                 505                 510

Val Asn Ile Asn Gly Gln Leu Pro Gln Arg Tyr Arg Ala Arg Ile Arg
        515                 520                 525

Tyr Ala Ser Thr Thr Asn Leu Arg Ile Tyr Val Thr Val Ala Gly Glu
    530                 535                 540

Arg Ile Phe Ala Gly Gln Phe Asn Lys Thr Met Asp Thr Gly Asp Pro
545                 550                 555                 560

Leu Thr Phe Gln Ser Phe Ser Tyr Ala Thr Ile Asn Thr Ala Phe Thr
                565                 570                 575

Phe Pro Met Ser Gln Ser Ser Phe Thr Val Gly Ala Asp Thr Phe Ser
            580                 585                 590

Ser Gly Asn Glu Val Tyr Ile Asp Arg Phe Glu Leu Ile Pro Val Thr
        595                 600                 605

Ala Thr Phe Glu Ala Glu Tyr Asp Leu Glu Arg Ala Gln Lys Ala Val
    610                 615                 620

Asn Ala Leu Phe Thr Ser Ile Asn Gln Ile Gly Ile Lys Thr Asp Val
625                 630                 635                 640

Thr Asp Tyr His Ile Asp Gln Val Ser Asn Leu Val Asp Cys Leu Ser
                645                 650                 655

Asp Glu Phe Cys Leu Asp Glu Lys Arg Glu Leu Ser Glu Lys Val Lys
            660                 665                 670

His Ala Lys Arg Leu Ser Asp Glu Arg Asn Leu Leu Gln Asp Pro Asn
        675                 680                 685

Phe Lys Gly Ile Asn Arg Gln Leu Asp Arg Gly Trp Arg Gly Ser Thr
    690                 695                 700

Asp Ile Thr Ile Gln Arg Gly Asp Asp Val Phe Lys Glu Asn Tyr Val
705                 710                 715                 720

Thr Leu Pro Gly Thr Phe Asp Glu Cys Tyr Pro Thr Tyr Leu Tyr Gln
                725                 730                 735

Lys Ile Asp Glu Ser Lys Leu Lys Ala Phe Thr Arg Tyr Gln Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
    770                 775                 780

Pro Leu Ser Ala Gln Ser Pro Ile Gly Lys Cys Gly Glu Pro Asn Arg
785                 790                 795                 800
```

```
Cys Ala Pro His Leu Glu Trp Asn Pro Asp Leu Asp Cys Ser Cys Arg
                805                 810                 815

Asp Gly Glu Lys Cys Ala His His Ser His His Phe Ser Leu Asp Ile
            820                 825                 830

Asp Val Gly Cys Thr Asp Leu Asn Glu Asp Leu Gly Val Trp Val Ile
        835                 840                 845

Phe Lys Ile Lys Thr Gln Asp Gly His Ala Arg Leu Gly Asn Leu Glu
    850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
            900                 905                 910

Val Asn Ser Gln Tyr Asp Gln Leu Gln Ala Asp Thr Asn Ile Ala Met
        915                 920                 925

Ile His Ala Ala Asp Lys Arg Val His Ser Ile Arg Glu Ala Tyr Leu
    930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu  Gln Asn Asn Gln Arg  Ser Val Leu
        995                 1000                1005

Val Val  Pro Glu Trp Glu Ala  Glu Val Ser Gln Glu  Val Arg Val
    1010                1015                1020

Cys Pro  Gly Arg Gly Tyr Ile  Leu Arg Val Thr Ala  Tyr Lys Glu
    1025                1030                1035

Gly Tyr  Gly Glu Gly Cys Val  Thr Ile His Glu Ile  Glu Asn Asn
    1040                1045                1050

Thr Asp  Glu Leu Lys Phe Ser  Asn Cys Val Glu Glu  Glu Ile Tyr
    1055                1060                1065

Pro Asn  Asn Thr Val Thr Cys  Asn Asp Tyr Thr Val  Asn Gln Glu
    1070                1075                1080

Glu Tyr  Gly Gly Ala Tyr Thr  Ser Arg Asn Arg Gly  Tyr Asn Glu
    1085                1090                1095

Ala Pro  Ser Val Pro Ala Asp  Tyr Ala Ser Val Tyr  Glu Glu Lys
    1100                1105                1110

Ser Tyr  Thr Asp Gly Arg Arg  Glu Asn Pro Cys Glu  Phe Asn Arg
    1115                1120                1125

Gly Tyr  Arg Asp Tyr Thr Pro  Leu Pro Val Gly Tyr  Val Thr Lys
    1130                1135                1140

Glu Leu  Glu Tyr Phe Pro Glu  Thr Asp Lys Val Trp  Ile Glu Ile
    1145                1150                1155

Gly Glu  Thr Glu Gly Thr Phe  Ile Val Asp Ser Val  Glu Leu Leu
    1160                1165                1170

Leu Met  Glu Glu
    1175

<210> SEQ ID NO 15
<211> LENGTH: 20
```

-continued

<212> TYPE: DNA
<213> ORGANISM: Artificial
<220> FEATURE:
<223> OTHER INFORMATION: Description of Artificial Sequence: Synthetic

<400> SEQUENCE: 15
tatccaattc gaacgtcatc 20

<210> SEQ ID NO 16
<211> LENGTH: 20
<212> TYPE: DNA
<213> ORGANISM: Artificial
<220> FEATURE:
<223> OTHER INFORMATION: Description of Artificial Sequence: Synthetic

<400> SEQUENCE: 16
tttagtcatc gattaaatca 20

<210> SEQ ID NO 17
<211> LENGTH: 20
<212> TYPE: DNA
<213> ORGANISM: Artificial
<220> FEATURE:
<223> OTHER INFORMATION: Description of Artificial Sequence: Synthetic

<400> SEQUENCE: 17
ataataagag ctccaatgtt 20

<210> SEQ ID NO 18
<211> LENGTH: 20
<212> TYPE: DNA
<213> ORGANISM: Artificial
<220> FEATURE:
<223> OTHER INFORMATION: Description of Artificial Sequence: Synthetic

<400> SEQUENCE: 18
tacatcgtag tgcaactctt 20

<210> SEQ ID NO 19
<211> LENGTH: 20
<212> TYPE: DNA
<213> ORGANISM: Artificial
<220> FEATURE:
<223> OTHER INFORMATION: Description of Artificial Sequence: Synthetic

<400> SEQUENCE: 19
tcatggagag ctcctatgtt 20

<210> SEQ ID NO 20
<211> LENGTH: 20
<212> TYPE: DNA
<213> ORGANISM: Artificial
<220> FEATURE:
<223> OTHER INFORMATION: Description of Artificial Sequence: Synthetic

<400> SEQUENCE: 20
ttaacaagag ctcctatgtt 20

<210> SEQ ID NO 21
<211> LENGTH: 20
<212> TYPE: DNA
<213> ORGANISM: Artificial
<220> FEATURE:
<223> OTHER INFORMATION: Description of Artificial Sequence: Synthetic

<400> SEQUENCE: 21

-continued actaccaggt acctttgatg 20

<210> SEQ ID NO 22
<211> LENGTH: 20
<212> TYPE: DNA
<213> ORGANISM: Artificial
<220> FEATURE:
<223> OTHER INFORMATION: Description of Artificial Sequence: Synthetic

<400> SEQUENCE: 22
actaccgggt acctttgata 20

<210> SEQ ID NO 23
<211> LENGTH: 18
<212> TYPE: DNA
<213> ORGANISM: Artificial
<220> FEATURE:
<223> OTHER INFORMATION: Description of Artificial Sequence: Synthetic

<400> SEQUENCE: 23
atttgagtaa tactatcc 18

<210> SEQ ID NO 24
<211> LENGTH: 19
<212> TYPE: DNA
<213> ORGANISM: Artificial
<220> FEATURE:
<223> OTHER INFORMATION: Description of Artificial Sequence: Synthetic

<400> SEQUENCE: 24
attactcaaa taccattgg 19

<210> SEQ ID NO 25
<211> LENGTH: 3534
<212> TYPE: DNA
<213> ORGANISM: Artificial
<220> FEATURE:
<223> OTHER INFORMATION: Description of Artificial Sequence: Synthetic
<221> NAME/KEY: CDS
<222> LOCATION: (1)..(3531)

<400> SEQUENCE: 25

```
atg gat aac aat ccg aac atc aat gaa tgc att cct tat aat tgt tta       48
Met Asp Asn Asn Pro Asn Ile Asn Glu Cys Ile Pro Tyr Asn Cys Leu
1               5                   10                  15

agt aac cct gaa gta gaa gta tta ggt gga gaa aga ata gaa act ggt       96
Ser Asn Pro Glu Val Glu Val Leu Gly Gly Glu Arg Ile Glu Thr Gly
            20                  25                  30

tac acc cca atc gat att tcc ttg tcg cta acg caa ttt ctt ttg agt      144
Tyr Thr Pro Ile Asp Ile Ser Leu Ser Leu Thr Gln Phe Leu Leu Ser
        35                  40                  45

gaa ttt gtt ccc ggt gct gga ttt gtg tta gga cta gtt gat ata ata      192
Glu Phe Val Pro Gly Ala Gly Phe Val Leu Gly Leu Val Asp Ile Ile
    50                  55                  60

tgg gga att ttt ggt ccc tct caa tgg gac gca ttt ctt gta caa att      240
Trp Gly Ile Phe Gly Pro Ser Gln Trp Asp Ala Phe Leu Val Gln Ile
65                  70                  75                  80

gaa cag tta att aac caa aga ata gaa gaa ttc gct agg aac caa gcc      288
Glu Gln Leu Ile Asn Gln Arg Ile Glu Glu Phe Ala Arg Asn Gln Ala
                85                  90                  95

att tct aga tta gaa gga cta agc aat ctt tat caa att tac gca gaa      336
Ile Ser Arg Leu Glu Gly Leu Ser Asn Leu Tyr Gln Ile Tyr Ala Glu
            100                 105                 110

tct ttt aga gag tgg gaa gca gat cct act aat cca gca tta aga gaa      384
```

-continued

```
Ser Phe Arg Glu Trp Glu Ala Asp Pro Thr Asn Pro Ala Leu Arg Glu
        115                 120                 125

gag atg cgt att caa ttc aat gac atg aac agt gcc ctt aca acc gct      432
Glu Met Arg Ile Gln Phe Asn Asp Met Asn Ser Ala Leu Thr Thr Ala
    130                 135                 140

att cct ctt ttt gca gtt caa aat tat caa gtt cct ctt tta tca gta      480
Ile Pro Leu Phe Ala Val Gln Asn Tyr Gln Val Pro Leu Leu Ser Val
145                 150                 155                 160

tat gtt caa gct gca aat tta cat tta tca gtt ttg aga gat gtt tca      528
Tyr Val Gln Ala Ala Asn Leu His Leu Ser Val Leu Arg Asp Val Ser
                165                 170                 175

gtg ttt gga caa agg tgg gga ttt gat gcc gcg act atc aat agt cgt      576
Val Phe Gly Gln Arg Trp Gly Phe Asp Ala Ala Thr Ile Asn Ser Arg
            180                 185                 190

tat aat gat tta act agg ctt att ggc aac tat aca gat cat gct gta      624
Tyr Asn Asp Leu Thr Arg Leu Ile Gly Asn Tyr Thr Asp His Ala Val
        195                 200                 205

cgc tgg tac aat acg gga tta gag cgt gta tgg gga ccg gat tct aga      672
Arg Trp Tyr Asn Thr Gly Leu Glu Arg Val Trp Gly Pro Asp Ser Arg
    210                 215                 220

gat tgg ata aga tat aat caa ttt aga aga gaa tta aca cta act gta      720
Asp Trp Ile Arg Tyr Asn Gln Phe Arg Arg Glu Leu Thr Leu Thr Val
225                 230                 235                 240

tta gat atc gtt tct cta ttt ccg aac tat gat agt aga acg tat cca      768
Leu Asp Ile Val Ser Leu Phe Pro Asn Tyr Asp Ser Arg Thr Tyr Pro
                245                 250                 255

att cga aca gtt tcc caa tta aca aga gaa att tat aca aac cca gta      816
Ile Arg Thr Val Ser Gln Leu Thr Arg Glu Ile Tyr Thr Asn Pro Val
            260                 265                 270

tta gaa aat ttt gat ggt agt ttt cga ggc tcg gct cag ggc ata gaa      864
Leu Glu Asn Phe Asp Gly Ser Phe Arg Gly Ser Ala Gln Gly Ile Glu
        275                 280                 285

aga agt att agg agt cca cat ttg atg gat ata ctt aac agt ata acc      912
Arg Ser Ile Arg Ser Pro His Leu Met Asp Ile Leu Asn Ser Ile Thr
    290                 295                 300

atc tat acg gat gct cat agg ggt tat tat tat tgg tca ggg cat caa      960
Ile Tyr Thr Asp Ala His Arg Gly Tyr Tyr Tyr Trp Ser Gly His Gln
305                 310                 315                 320

ata atg gct tct cct gta ggg ttt tcg ggg cca gaa ttc act ttt ccg     1008
Ile Met Ala Ser Pro Val Gly Phe Ser Gly Pro Glu Phe Thr Phe Pro
                325                 330                 335

cta tat gga act atg gga aat gca gct cca caa caa cgt att gtt gct     1056
Leu Tyr Gly Thr Met Gly Asn Ala Ala Pro Gln Gln Arg Ile Val Ala
            340                 345                 350

caa cta ggt cag ggc gtg tat aga aca tta tcg tcc act tta tat aga     1104
Gln Leu Gly Gln Gly Val Tyr Arg Thr Leu Ser Ser Thr Leu Tyr Arg
        355                 360                 365

aga cct ttt aat ata ggg ata aat aat caa caa cta tct gtt ctt gac     1152
Arg Pro Phe Asn Ile Gly Ile Asn Asn Gln Gln Leu Ser Val Leu Asp
    370                 375                 380

ggg aca gaa ttt gct tat gga acc tcc tca aat ttg cca tcc gct gta     1200
Gly Thr Glu Phe Ala Tyr Gly Thr Ser Ser Asn Leu Pro Ser Ala Val
385                 390                 395                 400

tac aga aaa agc gga acg gta gat tcg ctg gat gaa ata ccg cca cag     1248
Tyr Arg Lys Ser Gly Thr Val Asp Ser Leu Asp Glu Ile Pro Pro Gln
                405                 410                 415

aat aac aac gtg cca cct agg caa gga ttt agt cat cga tta agc cat     1296
Asn Asn Asn Val Pro Pro Arg Gln Gly Phe Ser His Arg Leu Ser His
            420                 425                 430
```

-continued

```
gtt tca atg ttt cgt tca ggc ttt agt aat agt agt gta agt ata ata      1344
Val Ser Met Phe Arg Ser Gly Phe Ser Asn Ser Ser Val Ser Ile Ile
        435                 440                 445

aga gct cca atg ttt tct tgg acg cac cgt agt gca acc cct aca aat      1392
Arg Ala Pro Met Phe Ser Trp Thr His Arg Ser Ala Thr Pro Thr Asn
    450                 455                 460

aca att gat ccg gag agg att act caa ata cca ttg gta aaa gca cat      1440
Thr Ile Asp Pro Glu Arg Ile Thr Gln Ile Pro Leu Val Lys Ala His
465                 470                 475                 480

aca ctt cag tca ggt act act gtt gta aga ggg ccc ggg ttt acg gga      1488
Thr Leu Gln Ser Gly Thr Thr Val Val Arg Gly Pro Gly Phe Thr Gly
                485                 490                 495

gga gat att ctt cga cga aca agt gga gga cca ttt gct tat act att      1536
Gly Asp Ile Leu Arg Arg Thr Ser Gly Gly Pro Phe Ala Tyr Thr Ile
            500                 505                 510

gtt aat ata aat ggg caa tta ccc caa agg tat cgt gca aga ata cgc      1584
Val Asn Ile Asn Gly Gln Leu Pro Gln Arg Tyr Arg Ala Arg Ile Arg
        515                 520                 525

tat gcc tct act aca aat cta aga att tac gta acg gtt gca ggt gaa      1632
Tyr Ala Ser Thr Thr Asn Leu Arg Ile Tyr Val Thr Val Ala Gly Glu
    530                 535                 540

cgg att ttt gct ggt caa ttt aac aaa aca atg gat acc ggt gac cca      1680
Arg Ile Phe Ala Gly Gln Phe Asn Lys Thr Met Asp Thr Gly Asp Pro
545                 550                 555                 560

tta aca ttc caa tct ttt agt tac gca act att aat aca gct ttt aca      1728
Leu Thr Phe Gln Ser Phe Ser Tyr Ala Thr Ile Asn Thr Ala Phe Thr
                565                 570                 575

ttc cca atg agc cag agt agt ttc aca gta ggt gct gat act ttt agt      1776
Phe Pro Met Ser Gln Ser Ser Phe Thr Val Gly Ala Asp Thr Phe Ser
            580                 585                 590

tca ggg aat gaa gtt tat ata gac aga ttt gaa ttg att cca gtt act      1824
Ser Gly Asn Glu Val Tyr Ile Asp Arg Phe Glu Leu Ile Pro Val Thr
        595                 600                 605

gca aca ttt gaa gca gaa tat gat tta gaa aga gca caa aag gcg gtg      1872
Ala Thr Phe Glu Ala Glu Tyr Asp Leu Glu Arg Ala Gln Lys Ala Val
    610                 615                 620

aat gcg ctg ttt act tct ata aac caa ata ggg ata aaa aca gat gtg      1920
Asn Ala Leu Phe Thr Ser Ile Asn Gln Ile Gly Ile Lys Thr Asp Val
625                 630                 635                 640

acg gat tat cat att gat caa gta tcc aat tta gtg gat tgt tta tca      1968
Thr Asp Tyr His Ile Asp Gln Val Ser Asn Leu Val Asp Cys Leu Ser
                645                 650                 655

gat gaa ttt tgt ctg gat gaa aag cga gaa ttg tcc gag aaa gtc aaa      2016
Asp Glu Phe Cys Leu Asp Glu Lys Arg Glu Leu Ser Glu Lys Val Lys
            660                 665                 670

cat gcg aag cga ctc agt gat gag cgg aat tta ctt caa gat cca aac      2064
His Ala Lys Arg Leu Ser Asp Glu Arg Asn Leu Leu Gln Asp Pro Asn
        675                 680                 685

ttc aaa ggc atc aat agg caa cta gac cgt ggt tgg aga gga agt acg      2112
Phe Lys Gly Ile Asn Arg Gln Leu Asp Arg Gly Trp Arg Gly Ser Thr
    690                 695                 700

gat att acc atc caa aga gga gat gac gta ttc aaa gaa aat tat gtc      2160
Asp Ile Thr Ile Gln Arg Gly Asp Asp Val Phe Lys Glu Asn Tyr Val
705                 710                 715                 720

aca cta cca ggt acc ttt gat gag tgc tat cca aca tat ttg tat caa      2208
Thr Leu Pro Gly Thr Phe Asp Glu Cys Tyr Pro Thr Tyr Leu Tyr Gln
                725                 730                 735

aaa atc gat gaa tca aaa tta aaa gcc ttt acc cgt tat caa tta aga      2256
Lys Ile Asp Glu Ser Lys Leu Lys Ala Phe Thr Arg Tyr Gln Leu Arg
            740                 745                 750
```

-continued

```
ggg tat atc gaa gat agt caa gac tta gaa atc tat tta att cgc tac      2304
Gly Tyr Ile Glu Asp Ser Gln Asp Leu Glu Ile Tyr Leu Ile Arg Tyr
        755                 760                 765

aat gca aaa cat gaa aca gta aat gtg cca ggt acg ggt tcc tta tgg      2352
Asn Ala Lys His Glu Thr Val Asn Val Pro Gly Thr Gly Ser Leu Trp
    770                 775                 780

ccg ctt tca gcc caa agt cca atc gga aag tgt gga gag ccg aat cga      2400
Pro Leu Ser Ala Gln Ser Pro Ile Gly Lys Cys Gly Glu Pro Asn Arg
785                 790                 795                 800

tgc gcg cca cac ctt gaa tgg aat cct gac tta gat tgt tcg tgt agg      2448
Cys Ala Pro His Leu Glu Trp Asn Pro Asp Leu Asp Cys Ser Cys Arg
                805                 810                 815

gat gga gaa aag tgt gcc cat cat tcg cat cat ttc tcc tta gac att      2496
Asp Gly Glu Lys Cys Ala His His Ser His His Phe Ser Leu Asp Ile
            820                 825                 830

gat gta gga tgt aca gac tta aat gag gac cta ggt gta tgg gtg atc      2544
Asp Val Gly Cys Thr Asp Leu Asn Glu Asp Leu Gly Val Trp Val Ile
        835                 840                 845

ttt aag att aag acg caa gat ggg cac gca aga cta ggg aat cta gag      2592
Phe Lys Ile Lys Thr Gln Asp Gly His Ala Arg Leu Gly Asn Leu Glu
    850                 855                 860

ttt ctc gaa gag aaa cca tta gta gga gaa gcg cta gct cgt gtg aaa      2640
Phe Leu Glu Glu Lys Pro Leu Val Gly Glu Ala Leu Ala Arg Val Lys
865                 870                 875                 880

aga gcg gag aaa aaa tgg aga gac aaa cgt gaa aaa ttg gaa tgg gaa      2688
Arg Ala Glu Lys Lys Trp Arg Asp Lys Arg Glu Lys Leu Glu Trp Glu
                885                 890                 895

aca aat atc gtt tat aaa gag gca aaa gaa tct gta gat gct tta ttt      2736
Thr Asn Ile Val Tyr Lys Glu Ala Lys Glu Ser Val Asp Ala Leu Phe
            900                 905                 910

gta aac tct caa tat gat caa tta caa gcg gat acg aat att gcc atg      2784
Val Asn Ser Gln Tyr Asp Gln Leu Gln Ala Asp Thr Asn Ile Ala Met
        915                 920                 925

att cat gcg gca gat aaa cgt gtt cat agc att cga gaa gct tat ctg      2832
Ile His Ala Ala Asp Lys Arg Val His Ser Ile Arg Glu Ala Tyr Leu
    930                 935                 940

cct gag ctg tct gtg att ccg ggt gtc aat gcg gct att ttt gaa gaa      2880
Pro Glu Leu Ser Val Ile Pro Gly Val Asn Ala Ala Ile Phe Glu Glu
945                 950                 955                 960

tta gaa ggg cgt att ttc act gca ttc tcc cta tat gat gcg aga aat      2928
Leu Glu Gly Arg Ile Phe Thr Ala Phe Ser Leu Tyr Asp Ala Arg Asn
                965                 970                 975

gtc att aaa aat ggt gat ttt aat aat ggc tta tcc tgc tgg aac gtg      2976
Val Ile Lys Asn Gly Asp Phe Asn Asn Gly Leu Ser Cys Trp Asn Val
            980                 985                 990

aaa ggg cat gta gat gta gaa gaa  caa aac aac caa cgt  tcg gtc ctt    3024
Lys Gly His Val Asp Val Glu Glu  Gln Asn Asn Gln Arg  Ser Val Leu
        995                 1000                1005

gtt gtt  ccg gaa tgg gaa gca  gaa gtg tca caa gaa  gtt cgt gtc      3069
Val Val  Pro Glu Trp Glu Ala  Glu Val Ser Gln Glu  Val Arg Val
    1010                1015                1020

tgt ccg  ggt cgt ggc tat atc  ctt cgt gtc aca gcg  tac aag gag      3114
Cys Pro  Gly Arg Gly Tyr Ile  Leu Arg Val Thr Ala  Tyr Lys Glu
    1025                1030                1035

gga tat  gga gaa ggt tgc gta  acc att cat gag atc  gag aac aat      3159
Gly Tyr  Gly Glu Gly Cys Val  Thr Ile His Glu Ile  Glu Asn Asn
    1040                1045                1050

aca gac  gaa ctg aag ttt agc  aac tgc gta gaa gag  gaa atc tat      3204
Thr Asp  Glu Leu Lys Phe Ser  Asn Cys Val Glu Glu  Glu Ile Tyr
```

-continued

```
    1055                1060                1065

cca aat  aac acg gta acg tgt  aat gat tat act gta  aat caa gaa      3249
Pro Asn  Asn Thr Val Thr Cys  Asn Asp Tyr Thr Val  Asn Gln Glu
    1070                1075                1080

gaa tac  gga ggt gcg tac act  tct cgt aat cga gga  tat aac gaa      3294
Glu Tyr  Gly Gly Ala Tyr Thr  Ser Arg Asn Arg Gly  Tyr Asn Glu
    1085                1090                1095

gct cct  tcc gta cca gct gat  tat gcg tca gtc tat  gaa gaa aaa      3339
Ala Pro  Ser Val Pro Ala Asp  Tyr Ala Ser Val Tyr  Glu Glu Lys
    1100                1105                1110

tcg tat  aca gat gga cga aga  gag aat cct tgt gaa  ttt aac aga      3384
Ser Tyr  Thr Asp Gly Arg Arg  Glu Asn Pro Cys Glu  Phe Asn Arg
    1115                1120                1125

ggg tat  agg gat tac acg cca  cta cca gtt ggt tat  gtg aca aaa      3429
Gly Tyr  Arg Asp Tyr Thr Pro  Leu Pro Val Gly Tyr  Val Thr Lys
    1130                1135                1140

gaa tta  gaa tac ttc cca gaa  acc gat aag gta tgg  att gag att      3474
Glu Leu  Glu Tyr Phe Pro Glu  Thr Asp Lys Val Trp  Ile Glu Ile
    1145                1150                1155

gga gaa  acg gaa gga aca ttt  atc gtg gac agc gtg  gaa tta ctc      3519
Gly Glu  Thr Glu Gly Thr Phe  Ile Val Asp Ser Val  Glu Leu Leu
    1160                1165                1170

ctt atg  gag gaa tag                                                3534
Leu Met  Glu Glu
    1175


<210> SEQ ID NO 26
<211> LENGTH: 1177
<212> TYPE: PRT
<213> ORGANISM: Artificial

<400> SEQUENCE: 26

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
```

-continued

```
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Thr His Arg Ser Ala Thr Pro Thr Asn
    450                 455                 460

Thr Ile Asp Pro Glu Arg Ile Thr Gln Ile Pro Leu Val Lys Ala His
465                 470                 475                 480

Thr Leu Gln Ser Gly Thr Thr Val Val Arg Gly Pro Gly Phe Thr Gly
                485                 490                 495

Gly Asp Ile Leu Arg Arg Thr Ser Gly Gly Pro Phe Ala Tyr Thr Ile
            500                 505                 510

Val Asn Ile Asn Gly Gln Leu Pro Gln Arg Tyr Arg Ala Arg Ile Arg
        515                 520                 525

Tyr Ala Ser Thr Thr Asn Leu Arg Ile Tyr Val Thr Val Ala Gly Glu
    530                 535                 540

Arg Ile Phe Ala Gly Gln Phe Asn Lys Thr Met Asp Thr Gly Asp Pro
545                 550                 555                 560

Leu Thr Phe Gln Ser Phe Ser Tyr Ala Thr Ile Asn Thr Ala Phe Thr
                565                 570                 575

Phe Pro Met Ser Gln Ser Ser Phe Thr Val Gly Ala Asp Thr Phe Ser
            580                 585                 590

Ser Gly Asn Glu Val Tyr Ile Asp Arg Phe Glu Leu Ile Pro Val Thr
        595                 600                 605

Ala Thr Phe Glu Ala Glu Tyr Asp Leu Glu Arg Ala Gln Lys Ala Val
    610                 615                 620
```

-continued

```
Asn Ala Leu Phe Thr Ser Ile Asn Gln Ile Gly Ile Lys Thr Asp Val
625                 630                 635                 640

Thr Asp Tyr His Ile Asp Gln Val Ser Asn Leu Val Asp Cys Leu Ser
                645                 650                 655

Asp Glu Phe Cys Leu Asp Glu Lys Arg Glu Leu Ser Glu Lys Val Lys
            660                 665                 670

His Ala Lys Arg Leu Ser Asp Glu Arg Asn Leu Leu Gln Asp Pro Asn
        675                 680                 685

Phe Lys Gly Ile Asn Arg Gln Leu Asp Arg Gly Trp Arg Gly Ser Thr
    690                 695                 700

Asp Ile Thr Ile Gln Arg Gly Asp Asp Val Phe Lys Glu Asn Tyr Val
705                 710                 715                 720

Thr Leu Pro Gly Thr Phe Asp Glu Cys Tyr Pro Thr Tyr Leu Tyr Gln
                725                 730                 735

Lys Ile Asp Glu Ser Lys Leu Lys Ala Phe Thr Arg Tyr Gln Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
    770                 775                 780

Pro Leu Ser Ala Gln Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
                805                 810                 815

Asp Gly Glu Lys Cys Ala His His Ser His His Phe Ser Leu Asp Ile
            820                 825                 830

Asp Val Gly Cys Thr Asp Leu Asn Glu Asp Leu Gly Val Trp Val Ile
        835                 840                 845

Phe Lys Ile Lys Thr Gln Asp Gly His Ala Arg Leu Gly Asn Leu Glu
    850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
            900                 905                 910

Val Asn Ser Gln Tyr Asp Gln Leu Gln Ala Asp Thr Asn Ile Ala Met
        915                 920                 925

Ile His Ala Ala Asp Lys Arg Val His Ser Ile Arg Glu Ala Tyr Leu
    930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu  Gln Asn Asn Gln Arg  Ser Val Leu
        995                 1000                1005

Val Val  Pro Glu Trp Glu Ala  Glu Val Ser Gln Glu  Val Arg Val
    1010                1015                1020

Cys Pro  Gly Arg Gly Tyr Ile  Leu Arg Val Thr Ala  Tyr Lys Glu
    1025                1030                1035
```

-continued

```
Gly Tyr  Gly Glu Gly Cys Val  Thr Ile His Glu Ile  Glu Asn Asn
    1040                 1045                 1050

Thr Asp  Glu Leu Lys Phe Ser  Asn Cys Val Glu Glu  Glu Ile Tyr
    1055                 1060                 1065

Pro Asn  Asn Thr Val Thr Cys  Asn Asp Tyr Thr Val  Asn Gln Glu
    1070                 1075                 1080

Glu Tyr  Gly Gly Ala Tyr Thr  Ser Arg Asn Arg Gly  Tyr Asn Glu
    1085                 1090                 1095

Ala Pro  Ser Val Pro Ala Asp  Tyr Ala Ser Val Tyr  Glu Glu Lys
    1100                 1105                 1110

Ser Tyr  Thr Asp Gly Arg Arg  Glu Asn Pro Cys Glu  Phe Asn Arg
    1115                 1120                 1125

Gly Tyr  Arg Asp Tyr Thr Pro  Leu Pro Val Gly Tyr  Val Thr Lys
    1130                 1135                 1140

Glu Leu  Glu Tyr Phe Pro Glu  Thr Asp Lys Val Trp  Ile Glu Ile
    1145                 1150                 1155

Gly Glu  Thr Glu Gly Thr Phe  Ile Val Asp Ser Val  Glu Leu Leu
    1160                 1165                 1170

Leu Met  Glu Glu
    1175


<210> SEQ ID NO 27
<211> LENGTH: 3534
<212> TYPE: DNA
<213> ORGANISM: Artificial
<220> FEATURE:
<223> OTHER INFORMATION: Description of Artificial Sequence: Synthetic
<221> NAME/KEY: CDS
<222> LOCATION: (1)..(3531)

<400> SEQUENCE: 27

atg gat aac aat ccg aac atc aat gaa tgc att cct tat aat tgt tta       48
Met Asp Asn Asn Pro Asn Ile Asn Glu Cys Ile Pro Tyr Asn Cys Leu
1               5                   10                  15

agt aac cct gaa gta gaa gta tta ggt gga gaa aga ata gaa act ggt       96
Ser Asn Pro Glu Val Glu Val Leu Gly Gly Glu Arg Ile Glu Thr Gly
            20                  25                  30

tac acc cca atc gat att tcc ttg tcg cta acg caa ttt ctt ttg agt      144
Tyr Thr Pro Ile Asp Ile Ser Leu Ser Leu Thr Gln Phe Leu Leu Ser
        35                  40                  45

gaa ttt gtt ccc ggt gct gga ttt gtg tta gga cta gtt gat ata ata      192
Glu Phe Val Pro Gly Ala Gly Phe Val Leu Gly Leu Val Asp Ile Ile
    50                  55                  60

tgg gga att ttt ggt ccc tct caa tgg gac gca ttt ctt gta caa att      240
Trp Gly Ile Phe Gly Pro Ser Gln Trp Asp Ala Phe Leu Val Gln Ile
65                  70                  75                  80

gaa cag tta att aac caa aga ata gaa gaa ttc gct agg aac caa gcc      288
Glu Gln Leu Ile Asn Gln Arg Ile Glu Glu Phe Ala Arg Asn Gln Ala
                85                  90                  95

att tct aga tta gaa gga cta agc aat ctt tat caa att tac gca gaa      336
Ile Ser Arg Leu Glu Gly Leu Ser Asn Leu Tyr Gln Ile Tyr Ala Glu
            100                 105                 110

tct ttt aga gag tgg gaa gca gat cct act aat cca gca tta aga gaa      384
Ser Phe Arg Glu Trp Glu Ala Asp Pro Thr Asn Pro Ala Leu Arg Glu
        115                 120                 125

gag atg cgt att caa ttc aat gac atg aac agt gcc ctt aca acc gct      432
Glu Met Arg Ile Gln Phe Asn Asp Met Asn Ser Ala Leu Thr Thr Ala
    130                 135                 140

att cct ctt ttt gca gtt caa aat tat caa gtt cct ctt tta tca gta      480
```

-continued

```
Ile Pro Leu Phe Ala Val Gln Asn Tyr Gln Val Pro Leu Leu Ser Val
145                 150                 155                 160

tat gtt caa gct gca aat tta cat tta tca gtt ttg aga gat gtt tca      528
Tyr Val Gln Ala Ala Asn Leu His Leu Ser Val Leu Arg Asp Val Ser
                165                 170                 175

gtg ttt gga caa agg tgg gga ttt gat gcc gcg act atc aat agt cgt      576
Val Phe Gly Gln Arg Trp Gly Phe Asp Ala Ala Thr Ile Asn Ser Arg
            180                 185                 190

tat aat gat tta act agg ctt att ggc aac tat aca gat tat gct gta      624
Tyr Asn Asp Leu Thr Arg Leu Ile Gly Asn Tyr Thr Asp Tyr Ala Val
        195                 200                 205

cgc tgg tac aat acg gga tta gaa cgt gta tgg gga ccg gat tct aga      672
Arg Trp Tyr Asn Thr Gly Leu Glu Arg Val Trp Gly Pro Asp Ser Arg
    210                 215                 220

gat tgg gta agg tat aat caa ttt aga aga gaa tta aca cta act gta      720
Asp Trp Val Arg Tyr Asn Gln Phe Arg Arg Glu Leu Thr Leu Thr Val
225                 230                 235                 240

tta gat atc gtt gct ctg ttc ccg aat tat gat agt aga aga tat cca      768
Leu Asp Ile Val Ala Leu Phe Pro Asn Tyr Asp Ser Arg Arg Tyr Pro
                245                 250                 255

att cga aca gtt tcc caa tta aca aga gaa att tat aca aac cca gta      816
Ile Arg Thr Val Ser Gln Leu Thr Arg Glu Ile Tyr Thr Asn Pro Val
            260                 265                 270

tta gaa aat ttt gat ggt agt ttt cga ggc tcg gct cag ggc ata gaa      864
Leu Glu Asn Phe Asp Gly Ser Phe Arg Gly Ser Ala Gln Gly Ile Glu
        275                 280                 285

aga agt att agg agt cca cat ttg atg gat ata ctt aac agt ata acc      912
Arg Ser Ile Arg Ser Pro His Leu Met Asp Ile Leu Asn Ser Ile Thr
    290                 295                 300

atc tat acg gat gct cat agg ggt tat tat tat tgg tca ggg cat caa      960
Ile Tyr Thr Asp Ala His Arg Gly Tyr Tyr Tyr Trp Ser Gly His Gln
305                 310                 315                 320

ata atg gct tct cct gta ggg ttt tcg ggg cca gaa ttc act ttt ccg     1008
Ile Met Ala Ser Pro Val Gly Phe Ser Gly Pro Glu Phe Thr Phe Pro
                325                 330                 335

cta tat gga act atg gga aat gca gct cca caa caa cgt att gtt gct     1056
Leu Tyr Gly Thr Met Gly Asn Ala Ala Pro Gln Gln Arg Ile Val Ala
            340                 345                 350

caa cta ggt cag ggc gtg tat aga aca tta tcg tcc act tta tat aga     1104
Gln Leu Gly Gln Gly Val Tyr Arg Thr Leu Ser Ser Thr Leu Tyr Arg
        355                 360                 365

aga cct ttt aat ata ggg ata aat aat caa caa cta tct gtt ctt gac     1152
Arg Pro Phe Asn Ile Gly Ile Asn Asn Gln Gln Leu Ser Val Leu Asp
    370                 375                 380

ggg aca gaa ttt gct tat gga acc tcc tca aat ttg cca tcc gct gta     1200
Gly Thr Glu Phe Ala Tyr Gly Thr Ser Ser Asn Leu Pro Ser Ala Val
385                 390                 395                 400

tac aga aaa agc gga acg gta gat tcg ctg gat gaa ata ccg cca cag     1248
Tyr Arg Lys Ser Gly Thr Val Asp Ser Leu Asp Glu Ile Pro Pro Gln
                405                 410                 415

aat aac aac gtg cca cct agg caa gga ttt agt cat cga tta agc cat     1296
Asn Asn Asn Val Pro Pro Arg Gln Gly Phe Ser His Arg Leu Ser His
            420                 425                 430

gtt tca atg ttt cgt tca ggc ttt agt aat agt agt gta agt ata ata     1344
Val Ser Met Phe Arg Ser Gly Phe Ser Asn Ser Ser Val Ser Ile Ile
        435                 440                 445

aga gct cct atg ttc tct tgg ata cat cgt agt gct gaa ttt aat aat     1392
Arg Ala Pro Met Phe Ser Trp Ile His Arg Ser Ala Glu Phe Asn Asn
    450                 455                 460
```

-continued

```
ata att gca tcg gat agt att act caa ata cca ttg gta aaa gca cat      1440
Ile Ile Ala Ser Asp Ser Ile Thr Gln Ile Pro Leu Val Lys Ala His
465                 470                 475                 480

aca ctt cag tca ggt act act gtt gta aga ggg ccc ggg ttt acg gga      1488
Thr Leu Gln Ser Gly Thr Thr Val Val Arg Gly Pro Gly Phe Thr Gly
                485                 490                 495

gga gat att ctt cga cga aca agt gga gga cca ttt gct tat act att      1536
Gly Asp Ile Leu Arg Arg Thr Ser Gly Gly Pro Phe Ala Tyr Thr Ile
            500                 505                 510

gtt aat ata aat ggg caa tta ccc caa agg tat cgt gca aga ata cgc      1584
Val Asn Ile Asn Gly Gln Leu Pro Gln Arg Tyr Arg Ala Arg Ile Arg
        515                 520                 525

tat gcc tct act aca aat cta aga att tac gta acg gtt gca ggt gaa      1632
Tyr Ala Ser Thr Thr Asn Leu Arg Ile Tyr Val Thr Val Ala Gly Glu
    530                 535                 540

cgg att ttt gct ggt caa ttt aac aaa aca atg gat acc ggt gac cca      1680
Arg Ile Phe Ala Gly Gln Phe Asn Lys Thr Met Asp Thr Gly Asp Pro
545                 550                 555                 560

tta aca ttc caa tct ttt agt tac gca act att aat aca gct ttt aca      1728
Leu Thr Phe Gln Ser Phe Ser Tyr Ala Thr Ile Asn Thr Ala Phe Thr
                565                 570                 575

ttc cca atg agc cag agt agt ttc aca gta ggt gct gat act ttt agt      1776
Phe Pro Met Ser Gln Ser Ser Phe Thr Val Gly Ala Asp Thr Phe Ser
            580                 585                 590

tca ggg aat gaa gtt tat ata gac aga ttt gaa ttg att cca gtt act      1824
Ser Gly Asn Glu Val Tyr Ile Asp Arg Phe Glu Leu Ile Pro Val Thr
        595                 600                 605

gca aca ttt gaa gca gaa tat gat tta gaa aga gca caa aag gcg gtg      1872
Ala Thr Phe Glu Ala Glu Tyr Asp Leu Glu Arg Ala Gln Lys Ala Val
    610                 615                 620

aat gcg ctg ttt act tct ata aac caa ata ggg ata aaa aca gat gtg      1920
Asn Ala Leu Phe Thr Ser Ile Asn Gln Ile Gly Ile Lys Thr Asp Val
625                 630                 635                 640

acg gat tat cat att gat caa gta tcc aat tta gtg gat tgt tta tca      1968
Thr Asp Tyr His Ile Asp Gln Val Ser Asn Leu Val Asp Cys Leu Ser
                645                 650                 655

gat gaa ttt tgt ctg gat gaa aag cga gaa ttg tcc gag aaa gtc aaa      2016
Asp Glu Phe Cys Leu Asp Glu Lys Arg Glu Leu Ser Glu Lys Val Lys
            660                 665                 670

cat gcg aag cga ctc agt gat gag cgg aat tta ctt caa gat cca aac      2064
His Ala Lys Arg Leu Ser Asp Glu Arg Asn Leu Leu Gln Asp Pro Asn
        675                 680                 685

ttc aaa ggc atc aat agg caa cta gac cgt ggt tgg aga gga agt acg      2112
Phe Lys Gly Ile Asn Arg Gln Leu Asp Arg Gly Trp Arg Gly Ser Thr
    690                 695                 700

gat att acc atc caa aga gga gat gac gta ttc aaa gaa aat tat gtc      2160
Asp Ile Thr Ile Gln Arg Gly Asp Asp Val Phe Lys Glu Asn Tyr Val
705                 710                 715                 720

aca cta cca ggt acc ttt gat gag tgc tat cca aca tat ttg tat caa      2208
Thr Leu Pro Gly Thr Phe Asp Glu Cys Tyr Pro Thr Tyr Leu Tyr Gln
                725                 730                 735

aaa atc gat gaa tca aaa tta aaa gcc ttt acc cgt tat caa tta aga      2256
Lys Ile Asp Glu Ser Lys Leu Lys Ala Phe Thr Arg Tyr Gln Leu Arg
            740                 745                 750

ggg tat atc gaa gat agt caa gac tta gaa atc tat tta att cgc tac      2304
Gly Tyr Ile Glu Asp Ser Gln Asp Leu Glu Ile Tyr Leu Ile Arg Tyr
        755                 760                 765

aat gca aaa cat gaa aca gta aat gtg cca ggt acg ggt tcc tta tgg      2352
Asn Ala Lys His Glu Thr Val Asn Val Pro Gly Thr Gly Ser Leu Trp
    770                 775                 780
```

-continued

```
ccg ctt tca gcc caa agt cca atc gga aag tgt gga gag ccg aat cga     2400
Pro Leu Ser Ala Gln Ser Pro Ile Gly Lys Cys Gly Glu Pro Asn Arg
785                 790                 795                 800

tgc gcg cca cac ctt gaa tgg aat cct gac tta gat tgt tcg tgt agg     2448
Cys Ala Pro His Leu Glu Trp Asn Pro Asp Leu Asp Cys Ser Cys Arg
                805                 810                 815

gat gga gaa aag tgt gcc cat cat tcg cat cat ttc tcc tta gac att     2496
Asp Gly Glu Lys Cys Ala His His Ser His His Phe Ser Leu Asp Ile
            820                 825                 830

gat gta gga tgt aca gac tta aat gag gac cta ggt gta tgg gtg atc     2544
Asp Val Gly Cys Thr Asp Leu Asn Glu Asp Leu Gly Val Trp Val Ile
        835                 840                 845

ttt aag att aag acg caa gat ggg cac gca aga cta ggg aat cta gag     2592
Phe Lys Ile Lys Thr Gln Asp Gly His Ala Arg Leu Gly Asn Leu Glu
    850                 855                 860

ttt ctc gaa gag aaa cca tta gta gga gaa gcg cta gct cgt gtg aaa     2640
Phe Leu Glu Glu Lys Pro Leu Val Gly Glu Ala Leu Ala Arg Val Lys
865                 870                 875                 880

aga gcg gag aaa aaa tgg aga gac aaa cgt gaa aaa ttg gaa tgg gaa     2688
Arg Ala Glu Lys Lys Trp Arg Asp Lys Arg Glu Lys Leu Glu Trp Glu
                885                 890                 895

aca aat atc gtt tat aaa gag gca aaa gaa tct gta gat gct tta ttt     2736
Thr Asn Ile Val Tyr Lys Glu Ala Lys Glu Ser Val Asp Ala Leu Phe
            900                 905                 910

gta aac tct caa tat gat caa tta caa gcg gat acg aat att gcc atg     2784
Val Asn Ser Gln Tyr Asp Gln Leu Gln Ala Asp Thr Asn Ile Ala Met
        915                 920                 925

att cat gcg gca gat aaa cgt gtt cat agc att cga gaa gct tat ctg     2832
Ile His Ala Ala Asp Lys Arg Val His Ser Ile Arg Glu Ala Tyr Leu
    930                 935                 940

cct gag ctg tct gtg att ccg ggt gtc aat gcg gct att ttt gaa gaa     2880
Pro Glu Leu Ser Val Ile Pro Gly Val Asn Ala Ala Ile Phe Glu Glu
945                 950                 955                 960

tta gaa ggg cgt att ttc act gca ttc tcc cta tat gat gcg aga aat     2928
Leu Glu Gly Arg Ile Phe Thr Ala Phe Ser Leu Tyr Asp Ala Arg Asn
                965                 970                 975

gtc att aaa aat ggt gat ttt aat aat ggc tta tcc tgc tgg aac gtg     2976
Val Ile Lys Asn Gly Asp Phe Asn Asn Gly Leu Ser Cys Trp Asn Val
            980                 985                 990

aaa ggg cat gta gat gta gaa gaa  caa aac aac caa cgt  tcg gtc ctt    3024
Lys Gly His Val Asp Val Glu Glu  Gln Asn Asn Gln Arg  Ser Val Leu
        995                 1000                1005

gtt gtt  ccg gaa tgg gaa gca  gaa gtg tca caa gaa  gtt cgt gtc     3069
Val Val  Pro Glu Trp Glu Ala  Glu Val Ser Gln Glu  Val Arg Val
    1010                1015                1020

tgt ccg  ggt cgt ggc tat atc  ctt cgt gtc aca gcg  tac aag gag     3114
Cys Pro  Gly Arg Gly Tyr Ile  Leu Arg Val Thr Ala  Tyr Lys Glu
    1025                1030                1035

gga tat  gga gaa ggt tgc gta  acc att cat gag atc  gag aac aat     3159
Gly Tyr  Gly Glu Gly Cys Val  Thr Ile His Glu Ile  Glu Asn Asn
    1040                1045                1050

aca gac  gaa ctg aag ttt agc  aac tgc gta gaa gag  gaa atc tat     3204
Thr Asp  Glu Leu Lys Phe Ser  Asn Cys Val Glu Glu  Glu Ile Tyr
    1055                1060                1065

cca aat  aac acg gta acg tgt  aat gat tat act gta  aat caa gaa     3249
Pro Asn  Asn Thr Val Thr Cys  Asn Asp Tyr Thr Val  Asn Gln Glu
    1070                1075                1080

gaa tac  gga ggt gcg tac act  tct cgt aat cga gga  tat aac gaa     3294
Glu Tyr  Gly Gly Ala Tyr Thr  Ser Arg Asn Arg Gly  Tyr Asn Glu
```

```
    1085                1090                1095

gct cct  tcc gta cca gct gat  tat gcg tca gtc tat  gaa gaa aaa      3339
Ala Pro  Ser Val Pro Ala Asp  Tyr Ala Ser Val Tyr  Glu Glu Lys
    1100                1105                1110

tcg tat  aca gat gga cga aga  gag aat cct tgt gaa  ttt aac aga      3384
Ser Tyr  Thr Asp Gly Arg Arg  Glu Asn Pro Cys Glu  Phe Asn Arg
    1115                1120                1125

ggg tat  agg gat tac acg cca  cta cca gtt ggt tat  gtg aca aaa      3429
Gly Tyr  Arg Asp Tyr Thr Pro  Leu Pro Val Gly Tyr  Val Thr Lys
    1130                1135                1140

gaa tta  gaa tac ttc cca gaa  acc gat aag gta tgg  att gag att      3474
Glu Leu  Glu Tyr Phe Pro Glu  Thr Asp Lys Val Trp  Ile Glu Ile
    1145                1150                1155

gga gaa  acg gaa gga aca ttt  atc gtg gac agc gtg  gaa tta ctc      3519
Gly Glu  Thr Glu Gly Thr Phe  Ile Val Asp Ser Val  Glu Leu Leu
    1160                1165                1170

ctt atg  gag gaa tag                                                3534
Leu Met  Glu Glu
    1175


<210> SEQ ID NO 28
<211> LENGTH: 1177
<212> TYPE: PRT
<213> ORGANISM: Artificial

<400> SEQUENCE: 28

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240
```

-continued

```
Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Ala Ser Asp Ser Ile Thr Gln Ile Pro Leu Val Lys Ala His
465                 470                 475                 480

Thr Leu Gln Ser Gly Thr Thr Val Val Arg Gly Pro Gly Phe Thr Gly
                485                 490                 495

Gly Asp Ile Leu Arg Arg Thr Ser Gly Gly Pro Phe Ala Tyr Thr Ile
            500                 505                 510

Val Asn Ile Asn Gly Gln Leu Pro Gln Arg Tyr Arg Ala Arg Ile Arg
        515                 520                 525

Tyr Ala Ser Thr Thr Asn Leu Arg Ile Tyr Val Thr Val Ala Gly Glu
    530                 535                 540

Arg Ile Phe Ala Gly Gln Phe Asn Lys Thr Met Asp Thr Gly Asp Pro
545                 550                 555                 560

Leu Thr Phe Gln Ser Phe Ser Tyr Ala Thr Ile Asn Thr Ala Phe Thr
                565                 570                 575

Phe Pro Met Ser Gln Ser Ser Phe Thr Val Gly Ala Asp Thr Phe Ser
            580                 585                 590

Ser Gly Asn Glu Val Tyr Ile Asp Arg Phe Glu Leu Ile Pro Val Thr
        595                 600                 605

Ala Thr Phe Glu Ala Glu Tyr Asp Leu Glu Arg Ala Gln Lys Ala Val
    610                 615                 620

Asn Ala Leu Phe Thr Ser Ile Asn Gln Ile Gly Ile Lys Thr Asp Val
625                 630                 635                 640

Thr Asp Tyr His Ile Asp Gln Val Ser Asn Leu Val Asp Cys Leu Ser
                645                 650                 655

Asp Glu Phe Cys Leu Asp Glu Lys Arg Glu Leu Ser Glu Lys Val Lys
```

-continued

```
            660                 665                 670

His Ala Lys Arg Leu Ser Asp Glu Arg Asn Leu Leu Gln Asp Pro Asn
        675                 680                 685

Phe Lys Gly Ile Asn Arg Gln Leu Asp Arg Gly Trp Arg Gly Ser Thr
    690                 695                 700

Asp Ile Thr Ile Gln Arg Gly Asp Asp Val Phe Lys Glu Asn Tyr Val
705                 710                 715                 720

Thr Leu Pro Gly Thr Phe Asp Glu Cys Tyr Pro Thr Tyr Leu Tyr Gln
                725                 730                 735

Lys Ile Asp Glu Ser Lys Leu Lys Ala Phe Thr Arg Tyr Gln Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
    770                 775                 780

Pro Leu Ser Ala Gln Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
                805                 810                 815

Asp Gly Glu Lys Cys Ala His His Ser His His Phe Ser Leu Asp Ile
            820                 825                 830

Asp Val Gly Cys Thr Asp Leu Asn Glu Asp Leu Gly Val Trp Val Ile
        835                 840                 845

Phe Lys Ile Lys Thr Gln Asp Gly His Ala Arg Leu Gly Asn Leu Glu
    850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
            900                 905                 910

Val Asn Ser Gln Tyr Asp Gln Leu Gln Ala Asp Thr Asn Ile Ala Met
        915                 920                 925

Ile His Ala Ala Asp Lys Arg Val His Ser Ile Arg Glu Ala Tyr Leu
    930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu  Gln Asn Asn Gln Arg  Ser Val Leu
        995                 1000                1005

Val Val  Pro Glu Trp Glu Ala  Glu Val Ser Gln Glu  Val Arg Val
    1010                1015                1020

Cys Pro  Gly Arg Gly Tyr Ile  Leu Arg Val Thr Ala  Tyr Lys Glu
    1025                1030                1035

Gly Tyr  Gly Glu Gly Cys Val  Thr Ile His Glu Ile  Glu Asn Asn
    1040                1045                1050

Thr Asp  Glu Leu Lys Phe Ser  Asn Cys Val Glu Glu  Glu Ile Tyr
    1055                1060                1065

Pro Asn  Asn Thr Val Thr Cys  Asn Asp Tyr Thr Val  Asn Gln Glu
    1070                1075                1080
```

```
Glu Tyr  Gly Gly Ala Tyr Thr  Ser Arg Asn Arg Gly  Tyr Asn Glu
    1085                 1090                 1095

Ala Pro  Ser Val Pro Ala Asp  Tyr Ala Ser Val Tyr  Glu Glu Lys
    1100                 1105                 1110

Ser Tyr  Thr Asp Gly Arg Arg  Glu Asn Pro Cys Glu  Phe Asn Arg
    1115                 1120                 1125

Gly Tyr  Arg Asp Tyr Thr Pro  Leu Pro Val Gly Tyr  Val Thr Lys
    1130                 1135                 1140

Glu Leu  Glu Tyr Phe Pro Glu  Thr Asp Lys Val Trp  Ile Glu Ile
    1145                 1150                 1155

Gly Glu  Thr Glu Gly Thr Phe  Ile Val Asp Ser Val  Glu Leu Leu
    1160                 1165                 1170

Leu Met  Glu Glu
    1175


<210> SEQ ID NO 29
<211> LENGTH: 3579
<212> TYPE: DNA
<213> ORGANISM: Artificial
<220> FEATURE:
<223> OTHER INFORMATION: Description of Artificial Sequence: Synthetic

<400> SEQUENCE: 29

atggataaca atccgaacat caatgaatgc attccttata attgtttaag taaccctgaa     60

gtagaagtat taggtggaga aagaatagaa actggttaca ccccaatcga tatttccttg    120

tcgctaacgc aatttctttt gagtgaattt gttcccggtg ctggatttgt gttaggacta    180

gttgatataa tatggggaat ttttggtccc tctcaatggg acgcatttct tgtacaaatt    240

gaacagttaa ttaaccaaag aatagaagaa ttcgctagga accaagccat ttctagatta    300

gaaggactaa gcaatcttta tcaaatttac gcagaatctt ttagagagtg ggaagcagat    360

cctactaatc cagcattaag agaagagatg cgtattcaat tcaatgacat gaacagtgcc    420

cttacaaccg ctattcctct tttgcagtt caaaattatc aagttcctct tttatcagta     480

tatgttcaag ctgcaaattt acatttatca gttttgagag atgtttcagt gtttggacaa    540

aggtggggat ttgatgccgc gactatcaat agtcgttata atgatttaac taggcttatt    600

ggcaactata cagattatgc tgtacgctgg tacaatacgg gattagaacg tgtatgggga    660

ccggattcta gagattgggt aaggtataat caatttagaa gagaattaac actaactgta    720

ttagatatcg ttgctctgtt cccgaattat gatagtagaa gatatccaat tcgaacagtt    780

tcccaattaa caagagaaat ttatacaaac ccagtattag aaaattttga tggtagtttt    840

cgaggctcgg ctcagggcat agaaagaagt attaggagtc cacatttgat ggatatactt    900

aacagtataa ccatctatac ggatgctcat aggggttatt attattggtc agggcatcaa    960

ataatggctt ctcctgtagg gttttcgggg ccagaattca cttttccgct atatggaact   1020

atgggaaatg cagctccaca acaacgtatt gttgctcaac taggtcaggg cgtgtataga   1080

acattatcgt ccactttata tagaagacct tttaatatag ggataaataa tcaacaacta   1140

tctgttcttg acgggacaga atttgcttat ggaacctcct caaatttgcc atccgctgta   1200

tacagaaaaa gcggaacggt agattcgctg gatgaaatac cgccacagaa taacaacgtg   1260

ccacctaggc aaggatttag tcatcgatta agccatgttt caatgtttcg ttcaggcttt   1320

agtaatagta gtgtaagtat aataagagct cctatgttct cttggataca tcgtagtgca   1380

actcttacaa atacaattga tccagagaga attaatcaaa tacctttagt gaaaggattt   1440
```

```
agagtttggg ggggcacctc tgtcattaca ggaccaggat ttacaggagg ggatatcctt   1500

cgaagaaata cctttggtga ttttgtatct ctacaagtca atattaattc accaattacc   1560

caaagatacc gtttaagatt tcgttacgct tccagtaggg atgcacgagt tatagtatta   1620

acaggagcgg catccacagg agtgggaggc caagttagtg taaatatgcc tcttcagaaa   1680

actatggaaa taggggagaa cttaacatct agaacattta gatataccga ttttagtaat   1740

ccttttcat ttagagctaa tccagatata attgggataa gtgaacaacc tctatttggt   1800

gcaggttcta ttagtagcgg tgaactttat atagataaaa ttgaaattat tctagcagat   1860

gcaacatttg aagcagaatc tgatttagaa agagcacaaa aggcggtgaa tgccctgttt   1920

acttcttcca atcaaatcgg gttaaaaacc gatgtgacgg attatcatat tgatcaagta   1980

tccaatttag tggattgttt atcagatgaa ttttgtctgg atgaaaagcg agaattgtcc   2040

gagaaagtca aacatgcgaa gcgactcagt gatgagcgga atttacttca agatccaaac   2100

ttcagaggga tcaatagaca accagaccgt ggctggagag gaagtacaga tattaccatc   2160

caaggaggag atgacgtatt caaagagaat tacgtcacac taccgggtac cgttgatgag   2220

tgctatccaa cgtatttata tcagaaaata gatgagtcga aattaaaagc ttatacccgt   2280

tatgaattaa gagggtatat cgaagatagt caagacttag aaatctattt gatccgttac   2340

aatgcaaaac acgaaatagt aaatgtgcca ggcacgggtt ccttatggcc gctttcagcc   2400

caaagtccaa tcggaaagtg tggagaaccg aatcgatgcg cgccacacct tgaatggaat   2460

cctgatctag attgttcctg cagagacggg gaaaaatgtg cacatcattc ccatcatttc   2520

accttggata ttgatgttgg atgtacagac ttaaatgagg acttaggtgt atgggtgata   2580

ttcaagatta agacgcaaga tggccatgca agactaggga atctagagtt tctcgaagag   2640

aaaccattat taggggaagc actagctcgt gtgaaaagag cggagaagaa gtggagagac   2700

aaacgagaga aactgcagtt ggaaacaaat attgtttata aagaggcaaa agaatctgta   2760

gatgctttat ttgtaaactc tcaatatgat agattacaag tggatacgaa catcgcaatg   2820

attcatgcgg cagataaacg cgttcataga atccgggaag cgtatctgcc agagttgtct   2880

gtgattccag gtgtcaatgc ggccattttc gaagaattag agggacgtat ttttacagcg   2940

tattccttat atgatgcgag aaatgtcatt aaaaatggcg atttcaataa tggcttatta   3000

tgctggaacg tgaaaggtca tgtagatgta gaagagcaaa acaaccaccg ttcggtcctt   3060

gttatcccag aatgggaggc agaagtgtca caagaggttc gtgtctgtcc aggtcgtggc   3120

tatatccttc gtgtcacagc atataaagag ggatatggag agggctgcgt aacgatccat   3180

gagatcgaag acaatacaga cgaactgaaa ttcagcaact gtgtagaaga ggaagtatat   3240

ccaaacaaca cagtaacgtg taataattat actgggactc aagaagaata tgagggtacg   3300

tacacttctc gtaatcaagg atatgacgaa gcctatggta ataacccttc cgtaccagct   3360

gattacgctt cagtctatga agaaaaatcg tatacagatg gacgaagaga gaatccttgt   3420

gaatctaaca gaggctatgg ggattacaca ccactaccgg ctggttatgt aacaaaggat   3480

ttagagtact tcccagagac cgataaggta tggattgaga tcggagaaac agaaggaaca   3540

ttcatcgtgg atagcgtgga attactcctt atggaggaa                          3579
```

<210> SEQ ID NO 30
<211> LENGTH: 1193
<212> TYPE: PRT
<213> ORGANISM: Artificial
<220> FEATURE:

-continued

<223> OTHER INFORMATION: Description of Artificial Sequence: Synthetic

<400> SEQUENCE: 30

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400
```

-continued

```
Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Thr Leu Thr Asn
    450                 455                 460

Thr Ile Asp Pro Glu Arg Ile Asn Gln Ile Pro Leu Val Lys Gly Phe
465                 470                 475                 480

Arg Val Trp Gly Gly Thr Ser Val Ile Thr Gly Pro Gly Phe Thr Gly
                485                 490                 495

Gly Asp Ile Leu Arg Arg Asn Thr Phe Gly Asp Phe Val Ser Leu Gln
            500                 505                 510

Val Asn Ile Asn Ser Pro Ile Thr Gln Arg Tyr Arg Leu Arg Phe Arg
        515                 520                 525

Tyr Ala Ser Ser Arg Asp Ala Arg Val Ile Val Leu Thr Gly Ala Ala
    530                 535                 540

Ser Thr Gly Val Gly Gly Gln Val Ser Val Asn Met Pro Leu Gln Lys
545                 550                 555                 560

Thr Met Glu Ile Gly Glu Asn Leu Thr Ser Arg Thr Phe Arg Tyr Thr
                565                 570                 575

Asp Phe Ser Asn Pro Phe Ser Phe Arg Ala Asn Pro Asp Ile Ile Gly
            580                 585                 590

Ile Ser Glu Gln Pro Leu Phe Gly Ala Gly Ser Ile Ser Ser Gly Glu
        595                 600                 605

Leu Tyr Ile Asp Lys Ile Glu Ile Ile Leu Ala Asp Ala Thr Phe Glu
    610                 615                 620

Ala Glu Ser Asp Leu Glu Arg Ala Gln Lys Ala Val Asn Ala Leu Phe
625                 630                 635                 640

Thr Ser Ser Asn Gln Ile Gly Leu Lys Thr Asp Val Thr Asp Tyr His
                645                 650                 655

Ile Asp Gln Val Ser Asn Leu Val Asp Cys Leu Ser Asp Glu Phe Cys
            660                 665                 670

Leu Asp Glu Lys Arg Glu Leu Ser Glu Lys Val Lys His Ala Lys Arg
        675                 680                 685

Leu Ser Asp Glu Arg Asn Leu Leu Gln Asp Pro Asn Phe Arg Gly Ile
    690                 695                 700

Asn Arg Gln Pro Asp Arg Gly Trp Arg Gly Ser Thr Asp Ile Thr Ile
705                 710                 715                 720

Gln Gly Gly Asp Asp Val Phe Lys Glu Asn Tyr Val Thr Leu Pro Gly
                725                 730                 735

Thr Val Asp Glu Cys Tyr Pro Thr Tyr Leu Tyr Gln Lys Ile Asp Glu
            740                 745                 750

Ser Lys Leu Lys Ala Tyr Thr Arg Tyr Glu Leu Arg Gly Tyr Ile Glu
        755                 760                 765

Asp Ser Gln Asp Leu Glu Ile Tyr Leu Ile Arg Tyr Asn Ala Lys His
    770                 775                 780

Glu Ile Val Asn Val Pro Gly Thr Gly Ser Leu Trp Pro Leu Ser Ala
785                 790                 795                 800

Gln Ser Pro Ile Gly Lys Cys Gly Glu Pro Asn Arg Cys Ala Pro His
                805                 810                 815

Leu Glu Trp Asn Pro Asp Leu Asp Cys Ser Cys Arg Asp Gly Glu Lys
```

-continued

```
            820                 825                 830

Cys Ala His His Ser His His Phe Thr Leu Asp Ile Asp Val Gly Cys
        835                 840                 845

Thr Asp Leu Asn Glu Asp Leu Gly Val Trp Val Ile Phe Lys Ile Lys
    850                 855                 860

Thr Gln Asp Gly His Ala Arg Leu Gly Asn Leu Glu Phe Leu Glu Glu
865                 870                 875                 880

Lys Pro Leu Leu Gly Glu Ala Leu Ala Arg Val Lys Arg Ala Glu Lys
                885                 890                 895

Lys Trp Arg Asp Lys Arg Glu Lys Leu Gln Leu Glu Thr Asn Ile Val
            900                 905                 910

Tyr Lys Glu Ala Lys Glu Ser Val Asp Ala Leu Phe Val Asn Ser Gln
        915                 920                 925

Tyr Asp Arg Leu Gln Val Asp Thr Asn Ile Ala Met Ile His Ala Ala
    930                 935                 940

Asp Lys Arg Val His Arg Ile Arg Glu Ala Tyr Leu Pro Glu Leu Ser
945                 950                 955                 960

Val Ile Pro Gly Val Asn Ala Ala Ile Phe Glu Glu Leu Glu Gly Arg
                965                 970                 975

Ile Phe Thr Ala Tyr Ser Leu Tyr Asp Ala Arg Asn Val Ile Lys Asn
            980                 985                 990

Gly Asp Phe Asn Asn Gly Leu Leu  Cys Trp Asn Val Lys  Gly His Val
        995                 1000                1005

Asp Val  Glu Glu Gln Asn Asn  His Arg Ser Val Leu  Val Ile Pro
    1010                1015                1020

Glu Trp  Glu Ala Glu Val Ser  Gln Glu Val Arg Val  Cys Pro Gly
    1025                1030                1035

Arg Gly  Tyr Ile Leu Arg Val  Thr Ala Tyr Lys Glu  Gly Tyr Gly
    1040                1045                1050

Glu Gly  Cys Val Thr Ile His  Glu Ile Glu Asp Asn  Thr Asp Glu
    1055                1060                1065

Leu Lys  Phe Ser Asn Cys Val  Glu Glu Glu Val Tyr  Pro Asn Asn
    1070                1075                1080

Thr Val  Thr Cys Asn Asn Tyr  Thr Gly Thr Gln Glu  Glu Tyr Glu
    1085                1090                1095

Gly Thr  Tyr Thr Ser Arg Asn  Gln Gly Tyr Asp Glu  Ala Tyr Gly
    1100                1105                1110

Asn Asn  Pro Ser Val Pro Ala  Asp Tyr Ala Ser Val  Tyr Glu Glu
    1115                1120                1125

Lys Ser  Tyr Thr Asp Gly Arg  Arg Glu Asn Pro Cys  Glu Ser Asn
    1130                1135                1140

Arg Gly  Tyr Gly Asp Tyr Thr  Pro Leu Pro Ala Gly  Tyr Val Thr
    1145                1150                1155

Lys Asp  Leu Glu Tyr Phe Pro  Glu Thr Asp Lys Val  Trp Ile Glu
    1160                1165                1170

Ile Gly  Glu Thr Glu Gly Thr  Phe Ile Val Asp Ser  Val Glu Leu
    1175                1180                1185

Leu Leu  Met Glu Glu
    1190
```

<210> SEQ ID NO 31
<211> LENGTH: 16
<212> TYPE: DNA
<213> ORGANISM: Artificial

-continued

<220> FEATURE:
<223> OTHER INFORMATION: Description of Artificial Sequence: Synthetic

<400> SEQUENCE: 31
cgttgctctg ttcccg 16

<210> SEQ ID NO 32
<211> LENGTH: 20
<212> TYPE: DNA
<213> ORGANISM: Artificial
<220> FEATURE:
<223> OTHER INFORMATION: Description of Artificial Sequence: Synthetic

<400> SEQUENCE: 32
tcaaatacca ttggtaaaag 20

<210> SEQ ID NO 33
<211> LENGTH: 3534
<212> TYPE: DNA
<213> ORGANISM: Artificial
<220> FEATURE:
<223> OTHER INFORMATION: Description of Artificial Sequence: Synthetic

<400> SEQUENCE: 33
atggataaca atccgaacat caatgaatgc attccttata attgtttaag taaccctgaa 60
gtagaagtat taggtggaga aagaatagaa actggttaca ccccaatcga tatttccttg 120
tcgctaacgc aatttctttt gagtgaattt gttcccggtg ctggatttgt gttaggacta 180
gttgatataa tatggggaat ttttggtccc tctcaatggg acgcatttct tgtacaaatt 240
gaacagttaa ttaaccaaag aatagaagaa ttcgctagga accaagccat ttctagatta 300
gaaggactaa gcaatcttta tcaaatttac gcagaatctt ttagagagtg ggaagcagat 360
cctactaatc cagcattaag agaagagatg cgtattcaat tcaatgacat gaacagtgcc 420
cttacaaccg ctattcctct tttgcagtt caaaattatc aagttcctct tttatcagta 480
tatgttcaag ctgcaaattt acatttatca gttttgagag atgtttcagt gtttggacaa 540
aggtggggat ttgatgccgc gactatcaat agtcgttata atgatttaac taggcttatt 600
ggcaactata cagattatgc tgtacgctgg tacaatacgg gattagaacg tgtatgggga 660
ccggattcta gagattgggt aaggtataat caatttagaa gagaattaac actaactgta 720
ttagatatcg ttgctctgtt cccgaattat gatagtagaa gatatccaat tcgaacagtt 780
tcccaattaa caagagaaat ttatacaaac ccagtattag aaaattttga tggtagtttt 840
cgaggctcgg ctcagggcat agaaagaagt attaggagtc cacatttgat ggatatactt 900
aacagtataa ccatctatac ggatgctcat aggggttatt attattggtc agggcatcaa 960
ataatggctt ctcctgtagg gttttcgggg ccagaattca cttttccgct atatggaact 1020
atgggaaatg cagctccaca acaacgtatt gttgctcaac taggtcaggg cgtgtataga 1080
acattatcgt ccactttata tagaagacct tttaatatag ggataaataa tcaacaacta 1140
tctgttcttg acgggacaga atttgcttat ggaacctcct caaatttgcc atccgctgta 1200
tacagaaaaa gcggaacggt agattcgctg gatgaaatac cgccacagaa taacaacgtg 1260
ccacctaggc aaggatttag tcatcgatta agccatgttt caatgtttcg ttcaggcttt 1320
agtaatagta gtgtaagtat aataagagct cctatgttct cttggataca tcgtagtgct 1380
gaatttaata atataattgc atcggatagt attactcaaa taccattggt aaaagcacat 1440
acacttcagt caggtactac tgttgtaaga gggcccgggt ttacgggagg agatattctt 1500

-continued

```
cgacgaacaa gtggaggacc atttgcttat actattgtta atataaatgg gcaattaccc   1560

caaaggtatc gtgcaagaat acgctatgcc tctactacaa atctaagaat ttacgtaacg   1620

gttgcaggtg aacggatttt tgctggtcaa tttaacaaaa caatggatac cggtgaccca   1680

ttaacattcc aatcttttag ttacgcaact attaatacag cttttacatt cccaatgagc   1740

cagagtagtt tcacagtagg tgctgatact tttagttcag ggaatgaagt ttatatagac   1800

agatttgaat tgattccagt tactgcaaca ctcgaggctg aatataatct ggaaagagcg   1860

cagaaggcgg tgaatgcgct gtttacgtct acaaaccaac tagggctaaa aacaaatgta   1920

acggattatc atattgatca agtgtccaat ttagttacgt atttatcgga tgaattttgt   1980

ctggatgaaa agcgagaatt gtccgagaaa gtcaaacatg cgaagcgact cagtgatgaa   2040

cgcaatttac tccaagattc aaatttcaaa gacattaata ggcaaccaga acgtgggtgg   2100

ggcggaagta cagggattac catccaagga ggggatgacg tatttaaaga aaattacgtc   2160

acactatcag gtacctttga tgagtgctat ccaacatatt tgtatcaaaa aatcgatgaa   2220

tcaaaattaa aagcctttac ccgttatcaa ttaagagggt atatcgaaga tagtcaagac   2280

ttagaaatct atttaattcg ctacaatgca aaacatgaaa cagtaaatgt gccaggtacg   2340

ggttccttat ggccgctttc agcccaaagt ccaatcggaa agtgtggaga gccgaatcga   2400

tgcgcgccac accttgaatg gaatcctgac ttagattgtt cgtgtaggga tggagaaaag   2460

tgtgcccatc attcgcatca tttctcctta gacattgatg taggatgtac agacttaaat   2520

gaggacctag gtgtatgggt gatctttaag attaagacgc aagatgggca cgcaagacta   2580

gggaatctag agtttctcga agagaaacca ttagtaggag aagcgctagc tcgtgtgaaa   2640

agagcggaga aaaaatggag agacaaacgt gaaaaattgg aatgggaaac aaatatcgtt   2700

tataaagagg caaaagaatc tgtagatgct ttatttgtaa actctcaata tgatcaatta   2760

caagcggata cgaatattgc catgattcat gcggcagata aacgtgttca tagcattcga   2820

gaagcttatc tgcctgagct gtctgtgatt ccgggtgtca atgcggctat ttttgaagaa   2880

ttagaagggc gtattttcac tgcattctcc ctatatgatg cgagaaatgt cattaaaaat   2940

ggtgatttta ataatggctt atcctgctgg aacgtgaaag ggcatgtaga tgtagaagaa   3000

caaaacaacc aacgttcggt ccttgttgtt ccggaatggg aagcagaagt gtcacaagaa   3060

gttcgtgtct gtccgggtcg tggctatatc cttcgtgtca cagcgtacaa ggagggatat   3120

ggagaaggtt gcgtaaccat tcatgagatc gagaacaata cagacgaact gaagtttagc   3180

aactgcgtag aagaggaaat ctatccaaat aacacggtaa cgtgtaatga ttatactgta   3240

aatcaagaag aatacggagg tgcgtacact tctcgtaatc gaggatataa cgaagctcct   3300

tccgtaccag ctgattatgc gtcagtctat gaagaaaaat cgtatacaga tggacgaaga   3360

gagaatcctt gtgaatttaa cagagggtat agggattaca cgccactacc agttggttat   3420

gtgacaaaag aattagaata cttcccagaa accgataagg tatggattga gattggagaa   3480

acggaaggaa catttatcgt ggacagcgtg gaattactcc ttatggagga atag         3534
```

```
<210> SEQ ID NO 34
<211> LENGTH: 1177
<212> TYPE: PRT
<213> ORGANISM: Artificial
<220> FEATURE:
<223> OTHER INFORMATION: Description of Artificial Sequence: Synthetic

<400> SEQUENCE: 34

Met Asp Asn Asn Pro Asn Ile Asn Glu Cys Ile Pro Tyr Asn Cys Leu
```

-continued

```
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430
```

```
Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Ala Ser Asp Ser Ile Thr Gln Ile Pro Leu Val Lys Ala His
465                 470                 475                 480

Thr Leu Gln Ser Gly Thr Thr Val Val Arg Gly Pro Gly Phe Thr Gly
                485                 490                 495

Gly Asp Ile Leu Arg Arg Thr Ser Gly Gly Pro Phe Ala Tyr Thr Ile
            500                 505                 510

Val Asn Ile Asn Gly Gln Leu Pro Gln Arg Tyr Arg Ala Arg Ile Arg
        515                 520                 525

Tyr Ala Ser Thr Thr Asn Leu Arg Ile Tyr Val Thr Val Ala Gly Glu
    530                 535                 540

Arg Ile Phe Ala Gly Gln Phe Asn Lys Thr Met Asp Thr Gly Asp Pro
545                 550                 555                 560

Leu Thr Phe Gln Ser Phe Ser Tyr Ala Thr Ile Asn Thr Ala Phe Thr
                565                 570                 575

Phe Pro Met Ser Gln Ser Ser Phe Thr Val Gly Ala Asp Thr Phe Ser
            580                 585                 590

Ser Gly Asn Glu Val Tyr Ile Asp Arg Phe Glu Leu Ile Pro Val Thr
        595                 600                 605

Ala Thr Leu Glu Ala Glu Tyr Asn Leu Glu Arg Ala Gln Lys Ala Val
    610                 615                 620

Asn Ala Leu Phe Thr Ser Thr Asn Gln Leu Gly Leu Lys Thr Asn Val
625                 630                 635                 640

Thr Asp Tyr His Ile Asp Gln Val Ser Asn Leu Val Thr Tyr Leu Ser
                645                 650                 655

Asp Glu Phe Cys Leu Asp Glu Lys Arg Glu Leu Ser Glu Lys Val Lys
            660                 665                 670

His Ala Lys Arg Leu Ser Asp Glu Arg Asn Leu Leu Gln Asp Ser Asn
        675                 680                 685

Phe Lys Asp Ile Asn Arg Gln Pro Glu Arg Gly Trp Gly Gly Ser Thr
    690                 695                 700

Gly Ile Thr Ile Gln Gly Gly Asp Asp Val Phe Lys Glu Asn Tyr Val
705                 710                 715                 720

Thr Leu Ser Gly Thr Phe Asp Glu Cys Tyr Pro Thr Tyr Leu Tyr Gln
                725                 730                 735

Lys Ile Asp Glu Ser Lys Leu Lys Ala Phe Thr Arg Tyr Gln Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
    770                 775                 780

Pro Leu Ser Ala Gln Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
                805                 810                 815

Asp Gly Glu Lys Cys Ala His His Ser His His Phe Ser Leu Asp Ile
            820                 825                 830

Asp Val Gly Cys Thr Asp Leu Asn Glu Asp Leu Gly Val Trp Val Ile
        835                 840                 845
```

-continued

```
Phe Lys Ile Lys Thr Gln Asp Gly His Ala Arg Leu Gly Asn Leu Glu
    850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
            900                 905                 910

Val Asn Ser Gln Tyr Asp Gln Leu Gln Ala Asp Thr Asn Ile Ala Met
        915                 920                 925

Ile His Ala Ala Asp Lys Arg Val His Ser Ile Arg Glu Ala Tyr Leu
    930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu  Gln Asn Asn Gln Arg  Ser Val Leu
        995                 1000                1005

Val Val  Pro Glu Trp Glu Ala  Glu Val Ser Gln Glu  Val Arg Val
    1010                1015                1020

Cys Pro  Gly Arg Gly Tyr Ile  Leu Arg Val Thr Ala  Tyr Lys Glu
    1025                1030                1035

Gly Tyr  Gly Glu Gly Cys Val  Thr Ile His Glu Ile  Glu Asn Asn
    1040                1045                1050

Thr Asp  Glu Leu Lys Phe Ser  Asn Cys Val Glu Glu  Glu Ile Tyr
    1055                1060                1065

Pro Asn  Asn Thr Val Thr Cys  Asn Asp Tyr Thr Val  Asn Gln Glu
    1070                1075                1080

Glu Tyr  Gly Gly Ala Tyr Thr  Ser Arg Asn Arg Gly  Tyr Asn Glu
    1085                1090                1095

Ala Pro  Ser Val Pro Ala Asp  Tyr Ala Ser Val Tyr  Glu Glu Lys
    1100                1105                1110

Ser Tyr  Thr Asp Gly Arg Arg  Glu Asn Pro Cys Glu  Phe Asn Arg
    1115                1120                1125

Gly Tyr  Arg Asp Tyr Thr Pro  Leu Pro Val Gly Tyr  Val Thr Lys
    1130                1135                1140

Glu Leu  Glu Tyr Phe Pro Glu  Thr Asp Lys Val Trp  Ile Glu Ile
    1145                1150                1155

Gly Glu  Thr Glu Gly Thr Phe  Ile Val Asp Ser Val  Glu Leu Leu
    1160                1165                1170

Leu Met  Glu Glu
    1175


<210> SEQ ID NO 35
<211> LENGTH: 20
<212> TYPE: DNA
<213> ORGANISM: Artificial
<220> FEATURE:
<223> OTHER INFORMATION: Description of Artificial Sequence: Synthetic

<400> SEQUENCE: 35

tgcaacactc gaggctgaat                                                20
```

BROAD-SPECTRUM INSECT RESISTANT TRANSGENIC PLANTS

The present application is a divisional of U.S. application Ser. No. 08/922,505, filed Sep. 3, 1997, now U.S. Pat. No. 6,110,464, which is a continuation-in-part of U.S. patent application Ser. No. 08/754,490 filed Nov. 20, 1996, now U.S. Pat. No. 6,017,534. The entire contents of which is specifically incorporated herein by reference in its entirety.

1. BACKGROUND OF THE INVENTION

1.1 Field of the Invention

The present invention provides new proteins for combatting insects, and particularly, coleopteran, dipteran, and lepidopteran insects sensitive to the disclosed δ-endotoxins derived from *Bacillus thuringiensis*. The invention provides novel chimeric crystal proteins and the chimeric cry gene segments which encode them, as well as methods for making and usmg these DNA segments, methods of producing the encoded proteins, methods for making synthetically-modified chimeric crystal proteins, and methods of making and using the synthetic crystal proteins.

1.2 Description of Related Art

1.2.1 *B. Thuringiensis* Crystal Proteins

The Gram-positive soil bacteriumn *B. thuringiensis* is well known for its production of proteinaceous parasporal crystals, or δ-endotoxins, that are toxic to a variety of lepidopteran, coleopteran, and dipteran larvae. *B. thuringiensis* produces crystal proteins during sporulation which are specifically toxic to certain species of insects. Many different strains of *B. thuringiensis* have been shown to produce insecticidal crystal proteins, and compositions comprising *B. thuringiensis* strains which produce proteins having insecticidal activity have been used commercially as environmentally-acceptable insecticides because of their toxicity to the specific target insect, and nontoxicity to plants and other non-targeted organisms.

Commercial formulations of naturally occurring *B. thuringiensis* isolates have long been used for the biological control of agricultural insect pests. In commercial production, the spores and crystals obtained from the fermentation process are concentrated and formulated for foliar application according to conventional agricultural practices.

1.2.2 Nomenclature of Crystal Proteins

A review by Hӧfte et al., (1989) describes the general state of the art with respect to the majority of insecticidal *B. thuringiensis* strains that have been identified which are active against insects of the Order Lepidoptera, i.e., caterpillar insects. This treatise also describes *B. thuringiensis* strains having insecticidal activity against insects of the Orders Diptera (ie. flies and mosquitoes) and Coleoptera (ie. beetles). A number of genes encoding crystal proteins have been cloned from several strains of *B. thuringiensis*. Hӧfte et al. (1989) discusses the genes and proteins that were identified in *B. thuringiensis* prior to 1990, and sets forth the nomenclature and classification scheme which has traditionally been applied to *B. thuringiensis* genes and proteins. cry1 genes encode lepidopteran-toxic Cry1 proteins. cry2 genes encode Cry2 proteins that are toxic to both lepidopterans and dipterans. cry3 genes encode coleopteran-toxic Cry3 proteins, while cry4 genes encode dipteran-toxic Cry4 proteins, etc.

Recently a new nomenclature has been proposed which systematically classifies the Cry proteins based upon amino acid sequence homology rather than upon insect target specificities. This classification scheme is summarized in Table 1.

TABLE 1

REVISED *B. THURINGIENSIS* δ-ENDOTOXIN NOMENCLATURE[A]

| New | Old | GenBank Accession # |
|---|---|---|
| Cry1Aa | CryIA(a) | M11250 |
| Cry1Ab | CryIA(b) | M13898 |
| Cry1Ac | CryIA(c) | M11068 |
| Cry1Ad | CryIA(d) | M73250 |
| Cry1Ae | CryIA(e) | M65252 |
| Cry1Ba | CryIB | X06711 |
| Cry1Bb | ET5 | L32020 |
| Cry1Bc | PEG5 | Z46442 |
| Cry1Bd | CryE1 | U70726 |
| Cry1Ca | CryIC | X07518 |
| Cry1Cb | CryIC(b) | M97880 |
| Cry1Da | CryID | X54160 |
| Cry1Db | PrtB | Z22511 |
| Cry1Ea | CryIE | X53985 |
| Cry1Eb | CryIE(b) | M73253 |
| Cry1Fa | CryIF | M63897 |
| Cry1Fb | PrtD | Z22512 |
| Cry1Ga | PrtA | Z22510 |
| Cry1Gb | CryH2 | U70725 |
| Cry1Ha | PrtC | Z22513 |
| Cry1Hb | | U35780 |
| Cry1Ia | CryV | X62821 |
| Cry1Ib | CryV | U07642 |
| Cry1Ja | ET4 | L32019 |
| Cry1Jb | ET1 | U31527 |
| Cry1K | | U28801 |
| Cry2Aa | CryIIA | M31738 |
| Cry2Ab | CryIIB | M23724 |
| Cry2Ac | CryIIC | X57252 |
| Cry3A | CryIIIA | M22472 |
| Cry3Ba | CryIIIB | X17123 |
| Cry3Bb | CryIIIB2 | M89794 |
| Cry3C | CryIIID | X59797 |
| Cry4A | CryIVA | Y00423 |
| Cry4B | CryIVB | X07423 |
| Cry5Aa | CryVA(a) | L07025 |
| Cry5Ab | CryVA(b) | L07026 |
| Cry5B | | U19725 |
| Cry6A | CryVIA | L07022 |
| Cry6B | CryVIB | L07024 |
| Cry7Aa | CryIIIC | M64478 |
| Cry7Ab | CryIIICb | U04367 |
| Cry8A | CryIIIE | U04364 |
| Cry8B | CryIIIG | U04365 |
| Cry8C | CryIIIF | U04366 |
| Cry9A | CryIG | X58120 |
| Cry9B | CryIX | X75019 |
| Cry9C | CryIH | Z37527 |
| Cry10A | CryIVC | M12662 |
| Cry11A | CryIVD | M31737 |
| Cry11B | Jeg80 | X86902 |
| Cry12A | CryVB | L07027 |
| Cry13A | CryVC | L07023 |
| Cry14A | CryVD | U13955 |
| Cry15A | 34kDa | M76442 |
| Cry16A | cbm71 | X94146 |
| Cry17A | cbm71 | X99478 |
| Cry18A | CryBP1 | X99049 |
| Cry19A | Jeg65 | Y08920 |
| Cyt1Aa | CytA | X03182 |
| Cyt1Ab | CytM | X98793 |
| Cyt1B | | U37196 |
| Cyt2A | CytB | Z14147 |
| Cyt2B | CytB | U52043 |

[A]Adapted from: http://epunix.biols.susx.ac.uk/Home/Neil__Crickmore/Bt/index.html

1.23 Mode of Crystal Protein Toxicity

All δ-endotoxin crystals are toxic to insect larvae by ingestion. Solubilization of the crystal in the midgut of the insect releases the protoxin form of the δ-endotoxin which, in most instances, is subsequently processed to an active toxin by midgut protease. The activated toxins recognize and bind to the brush-border of the insect midgut epithelium through receptor proteins. Several putative crystal protein receptors have been isolated from certain insect larvae (Knight et al., 1995; Gill et al., 1995; Masson et al., 1995). The binding of active toxins is followed by intercalation and aggregation of toxin molecules to form pores within the midgut epithelium. This process leads to osmotic imbalance, swelling, lysis of the cells lining the midgut epithelium, and eventual larvae mortality.

1.2.4 Molecular Biology of δ-Endotoxins

With the advent of molecular genetic techniques, various δ-endotoxin genes have been isolated and their DNA sequences determined. These genes have been used to construct certain genetically engineered *B. thuringiensis* products that have been approved for commercial use. Recent developments have seen new δ-endotoxin delivery systems developed, including plants that contain and express genetically engineered δ-endotoxin genes.

The cloning and sequencing of a number of δ-endotoxin genes from a variety of *Bacillus thuringiensis* strains have been described and are summarized by Höfte and Whiteley, 1989. Plasmid shuttle vectors designed for the cloning and expression of δ-endotoxin genes in *E. coli* or *B. thuringiensis* are described by Gawron-Burke and Baum (1991). U.S. Pat. No. 5,441,884 discloses a site-specific recombination system for constructing recombinant *B. thuringiensis* strans containing δ-endotoxin genes that are free of DNA not native to *B. thuringiensis.*

The Cry1 family of crystal proteins, which are primarily active against lepidopteran pests, are the best studied class of δ-endotoxins. The pro-toxin form of Cry1 δ-endotoxins consist of two approximately equal sized segments. The carboxyl-half, or pro-toxin segment, is not toxic and is thought to be important for crystal formation (Arvidson et al., 1989). The amino-half of the protoxin comprises the active-toxin segment of the Cry1 molecule and may be further divided into three structural domains as determined by the recently described crystallographic structure for the active toxin segment of the Cry1Aa δ-endotoxin (Grochulski et al., 1995). Domain 1 occupies the first third of the active toxin and is essential for channel formation (Thompson et al., 1995). Domain 2 and domain 3 occupy the middle and last third of the active toxin, respectively. Both domains 2 and 3 have been implicated in receptor binding and insect specificity, depending on the insect and δ-endotoxin being examined (Thompson et al., 1995).

1.2.5 Chumeric Crystal Proteins

In recent years, researchers have focused effort on the construction of hybrid δ-endotoxins with the hope of producing proteins with enhanced activity or improved properties. Advances in the art of molecular genetics over the past decade have facilitated a logical and orderly approach to engineering proteins with improved properties. Site-specific and random mutagenesis methods, the advent of polymerase chain reaction (PCR™) methodologies, and the development of recombinant methods for generating gene fusions and constructing chimeric proteins have facilitated an assortment of methods for changing amino acid sequences of proteins, fusing portions of two or more proteins together in a single recombinant protein, and altering genetic sequences that encode proteins of commercial interest.

Unfortunately, for crystal proteins, these techniques have only been exploited in limited fashion. The likelihood of arbitrarily creating a chimeric protein with enhanced properties from portions of the numerous native proteins which have been identified is remote given the complex nature of protein structure, folding, oligomerization, activation, and correct processing of the chimeric protoxin to an active moiety. Only by careful selection of specific target regions within each protein, and subsequent protein engineering can toxins be synthesized which have improved insecticidal activity.

Some success in the area, however, has been reported in the literature. For example, the construction of a few hybrid δ-endotoxins is reported in the following related art Intl. Pat. Appl. Publ. No. WO 95/30753 discloses the construction of hybrid *B. thuringiensis* δ-endotoxins for production in *Pseudomonas fluorescens* in which the non-toxic protoxin fragment of Cry1F has been replaced by the non-toxic protoxin fragment from the Cry1Ac/Cry1Ab that is disclosed in U.S. Pat. No. 5,128,130.

U.S. Pat. No. 5,128,130 discloses the construction of hybrid *B. thuringiensis* δ-endotoxins for production in *P. fluorescens* in which a portion of the non-toxic protoxin segment of Cry1Ac is replaced with the corresponding non-toxic protoxin fragment of Cry1Ab. U.S. Pat. No. 5,055,294 discloses the construction of a specific hybrid δ-endotoxin between Cry1Ac (amino acid residues 1–466) and Cry1Ab (amino acid residues 466–1155) for production in *P. fluorescens*. Although the aforementioned patent discloses the construction of a hybrid toxin within the active toxin segment, no specifics are presented in regard to the hybrid toxin's insecticidal activity. Intl. Pat. Appl. Publ. No. WO 95/30752 discloses the consuction of hybrid *B. thuringiensis* δ-endotoxins for production in *P. fluorescens* in which the non-toxic protoxin segment of Cry1C is replaced by the nontoxic protoxin segment from Cry1Ab. The aforementioned application further discloses that the activity against *Spodoptera exigua* for the hybrid δ-endotoxin is improved over that of the parent active toxin, Cry1C.

Intl. Pat. Appi. Publ. No. WO 95/06730 discloses the construction of a hybrid *B. thuringiensis* δ-endotoxin consisting of domains 1 and 2 of Cry1E coupled to domain 3 and the non-toxic protoxin segment of Cry1C. Insect bioassays performed against *Manduca sexta* (sensitive to Cry1C and Cry1E), *Spodoptera exigua* (sensitive to Cry1C), and *Mamestra brassicae* (sensitive to Cry1C) show that the hybrid Cry1E/Cry1C hybrid toxin is active against *M. sexta, S. exigua*, and *M. brassicae*. The bioassay results were expressed as $EC_{50}$ values (toxin concentration giving a 50% growth reduction) rather than $LC_{50}$ values (toxin concentration giving 50% mortality). Although the δ-endotoxins used for bioassay were produced in *B. thuringiensis*, only artificially-generated active segments of the δ-endotoxins were used, not the naturally-produced crystals typically produced by *B. thuringiensis* that are present in commercial *B. thuringiensis* formulations. Bioassay results indicated that the $LC_{50}$ values for the hybrid Cry1E/Cry1C crystal against *S. frugiperda* were 1.5 to 1.7 fold lower (more active) than for native Cry1C. This art also discloses the construction of a hybrid *B. thuringiensis* δ-endotoxin between Cry1Ab (domains 1 and 2) and Cry1C (domain 3 and the non-toxic protoxin segment), although no data are given regarding the hybrid toxin's activity or usefulness.

Lee et al. (1995) report the construction of hybrid *B. thuringiensis* δ-endotoxins between Cry1Ac and Cry1Aa within the active toxin segment. Artificially generated active segments of the hybrid toxins were used to examine protein interactions in susceptible insect brush border membranes vesicles (BBMV). The bioactivity of the hybrid toxins was not reported.

Honee et al. (1991) report the construction of hybrid δ-endotoxins between Cry1C (domain 1) and Cry1Ab (domains 2 and 3) and the reciprocal hybrid between Cry1Ab (domain 1) and Cry1C (domains 2 and 3). These hybrids failed to show any significant increase in activity against susceptible insects. Furthermore, the Cry1C (domain 1)/Cry1Ab (domains 2 and 3) hybrid toxin was found to be hypersensitive to protease degradation. A report by Schnepf et al. (1990) discloses the construction of Cry1Ac hybrid toxin in which a small portion of domain 2 was replaced by the corresponding region of Cry1Aa, although no significant increase in activity against susceptible insect larvae was observed.

1.3 Deficiencies in the Prior Art

The limited successes in producing chimeric crystal proteins which have improved activity have negatively impacted the field by thwarting efforts to produce recombinantly-engineered crystal protein for commercial development, and to extend the toxic properties and host specificities of the known endotoxins. Therefore, what is lacking in the prior art are reliable methods and compositions comprising recombinantly-engineered crystal proteins which have improved insecticidal activity, broad-host-range specificities, and which are suitable for commercial production in *B. thuringiensis.*

2. SUMMARY OF THE INVENTION

The present invention overcomes these and other limitations in the prior art by providing novel chimeric δ-endotoxins which have improved insecticidal properties, and broad-range specificities.

Disclosed are methods for the construction of *B. thuringiensis* hybrid δ-endotoxins comprising amino acid sequences from native Cry1Ac and Cry1F crystal proteins. These hybrid proteins, in which. all or a portion of Cry1Ac domain 2, all or a portion of Cry1Ac domain 3, and all or a portion of the Cry1Ac protoxin segment is replaced by the corresponding portions of Cry1F, possess not only the insecticidal characteristics of the parent δ-endotoxins, but also have the unexpected and remarkable properties of enhanced broad-range specificity which is not proficiently displayed by either of the native δ-endotoxins from which the chimeric proteins were engineered.

Specifically, the present invention discloses and claims genetically-engineered hybrid δ-endotoxins which comprise a portion of a Cry1Ac crystal protein fused to a portion of a Cry1F crystal protein. These chimeric endotoxins have broad-range specificity for the insect pests described herein.

In a further embodiment, the present invention also discloses and claims recombinant *B. thuringiensis* hybrid δ-endotoxins which comprise a portion of Cry1Ab, Cry1F, and Cry1Ac in which all or a portion of Cry1Ab domain 2 or all or a portion of Cry1Ab domain 3 is replaced by the corresponding portions of Cry1F and all or a portion of the Cry1Ab protoxin segment is replaced by the corresponding portions of Cry1Ac. Exemplary hybrid δ-endotoxins between Cry1Ab and Cry1F are identified in SEQ ID NO:13 and SEQ ID NO:14.

One aspect of the present invention demonstrates the unexpected result that certain hybrid δ-endotoxins derived from Cry1Ac and Cry1F proteins exhibit not only the insecticidal characteristics of the parent δ-endotoxins, but also possess insecticidal activity which is not proficiently displayed by either of the parent δ-endotoxins.

Another aspect of the invention further demonstrates the unexpected result that certain chimeric Cry1Ab/Cry1F proteins maintain not only the insecticidal characteristics of the parent δ-endotoxins, but also exhibit insecticidal activity which is not displayed by either the native Cry1Ab or Cry1F endotoxins.

The present invention also encompasses Cry1Ac/Cry1F and Cry1Ab/Cry1F hybrid δ-endotoxins that maintain the desirable characteristics needed for commercial production in *B. thuringiensis*. Specifically, the hybrid δ-endotoxins identified in SEQ ID NO:10, SEQ ID NO:12, SEQ ID NO:14, SEQ ID NO:26, SEQ ID NO:28, SEQ ID NO:30, and SEQ ID NO:34 can efficiently form proteinaceous parasporal inclusions in *B. thuringiensis* and have the favorable characteristics of solubility, protease susceptibility, and insecticidal activity of the parent δ-endotoxins.

In a further embodiment, the present invention also discloses and claims recombinant *B. thuringiensis* hybrid δ-endotoxins which comprise a portion of Cry1Ac and Cry1C in which all or a portion of Cry1Ac domain 3 is replaced by the corresponding portions of Cry1C and all or a portion of the Cry1Ac protoxin segment is replaced by the corresponding portion of Cry1C. Exemplary hybrid δ-endotoxins between Cry1Ac and Cry1C are identified in SEQ ID NO:29 and SEQ ID NO:30.

One aspect of the present invention demonstrates the unexpected result that, although neither Cry1Ac nor Cry1C possess *S. frugiperda* activity, the Cry1Ac/Cry1C hybrid δ-endotoxin identified by SEQ ID NO:29 and SEQ ID NO:30 has significant activity against *S. frugiperda*. Furthermore, the Cry1Ac/Cry1C hybrid δ-endotoxin identified by SEQ ID NO:29 and SEQ ID NO:30 has significantly better activity against *S. exigua* than the Cry1C parental δ-endotoxin.

The present invention further pertains to the recombinant nucleic acid sequences which encode the novel crystal proteins disclosed herein. Specifically, the invention discloses and claims the nucleic acid sequences of SEQ ID NO:9, SEQ ID NO:1 1, SEQ ID NO:13, SEQ ID NO:25, SEQ ID NO:27, SEQ ID NO:29, and SEQ ID NO:33; nucleic acid sequences which are complementary to the nucleic acid sequences of SEQ ID NO:9, SEQ ID NO:11, SEQ ID NO:13, SEQ ID NO:25, SEQ ID NO:27, SEQ ID NO:29; and SEQ ID NO:33, and nucleic acid sequences which hybridize to the sequences of SEQ ID NO:9, SEQ ID NO:11, SEQ ID NO:13, SEQ ID NO:25, SEQ ID NO:27, SEQ ID NO:29, and SEQ ID NO:33.

The novel hybrid δ-endotoxins disclosed herein are useful in the control of a broad range of insect pests. These hybrid δ-endotoxins are described in FIG. 1 and FIG. 4 and are disclosed in SEQ ID NO:10, SEQ ID NO:12, SEQ ID NO:14, SEQ ID NO:26, SEQ ID NO:28, SEQ ID NO:30, and SEQ ID NO:34. The nucleic acid segments encoding these proteins are disclosed in SEQ ID NO:9, SEQ ID NO:11, SEQ ID NO:13, SEQ ID NO:25, SEQ ID NO:27, SEQ ID NO:29, and SEQ ID NO:33. The insecticidal and biochemical properties of the hybrid δ-endotoxins are described in FIG. 2, FIG. 3, and Table 4, Table 5, Table 6, and Table 7. The broad host range of the improved δ-endotoxins specified in the present invention is useful in circumventing dilution effects caused by expressing multiple δ-endotoxin genes within a single *B. thuringiensis* strain. Expression of such a broad host range δ-endotoxin in plants is expected to impart protection against a wider variety of insect pests.

The impetus for constructing these and other hybrid δ-endotoxins is to create novel toxins with improved insecticidal activity, increased host-range specificity, and improved production characteristics. The DNA sequences listed in Table 7 define the exchange points for the hybrid δ-endotoxins pertinent to the present invention and as oligonucleotide primers, may be used to identify like or similar hybrid δ-endotoxins by Southern or colony hybridization under conditions of moderate to high stringency. Researchers skilled in the art will recognize the importance of the exchange site chosen between two or more δ-endotoxins can be achieved using a number of in vivo or in vitro molecular genetic techniques. Small variations in the exchange region between two or more δ-endotoxins may yield similar results or, as demonstrated for EG11062 and EG11063, adversely affect desirable traits. Similarly, large variations in the exchange region between two or more δ-endotoxins may have no effect on desired traits, as demonstrated by EG11063 and EG11074, or may adversely affect desirable traits, as demonstrated by EG11060 and EG11063.

Favorable traits with regard to improved insecticidal activity, increased host range, and improved production characteristics may be achieved by other such hybrid δ-endotoxins including, but not limited to, the cry1, cry2, cry3, cry4, cry5, cry6, cry7, cry8, cry9, cry10, cry11, cry12, cry13, cry14, cry15 class of δ-endotoxin genes and thuringiensis cytolytic cyt1 and cyt2 genes. Members of these classes of *B. thuringiensis* insecticidal proteins include, but are not limited to Cry1Aa, Cry1Ab, Cry1Ac, Cry1Ad, Cry1Ae, Cry1Ba, Cry1Bb, Cry1Ca, Cry1Cb, Cry1Da, Cry1Db, Cry1Ea, Cry1Eb, Cry1Fa, Cry1Fb, Cry1Ga, Cry1Ha, Cry2a, Cry2b, Cry1Ja, Cry1Ka, Cry1Aa, Cry11Ab, Cry12Aa, Cry3Ba, Cry3Bb, Cry3C, Cry4a, Cry4Ba, Cry5a, Cry5Ab, Cry6Aa, Cry6Ba, Cry7Aa, Cry7Ab, Cry8Aa, Cry8Ba, Cry8Ca, Cry9Aa, Cry9Ba, Cry9Ca, Cry10Aa, Cry11Aa, Cry12Aa, Cry13Aa, Cry14Aa, Cry15Aa, CytlAa, and Cyt2Aa. Related hybrid δ-endotoxins would consist of the amino portion of one of the aforementioned δ-endotoxins, including all or part of domain 1 or domain 2, fused to all or part of domain 3 from another of the aforementioned δ-endotoxins. The non-active protoxin fragment of such hybrid δ-endotoxins may consist of the protoxin fragment from any of the aforementioned δ-endotoxins which may act to stabilize the hybrid δ-endotoxin as demonstrated by EG11087 and EG11091 (see e.g., Table 4). Hybrid δ-endotoxins possessing similar traits as those described in the present invention could be constructed by conservative, or "similar" replacements of amino acids within hybrid δ-endotoxins. Such substitutions would mimic the biochemical and biophysical properties of the native amino acid at any position in the protein. Amino acids considered similar include for example, but are not limited to:

Ala, Ser, and Thr,

Asp and Glu;

Asn and Gln;

Lys and Arg;

Ile, Leu, Met, and Val; and

Phe, Tyr, and Trp.

Researchers skilled in the art will recognize that improved insecticidal activity, increased host range, and improved production characteristics imparted upon hybrid δ-endotoxins may be further improved by altering the genetic code for one or more amino acid positions in the hybrid δ-endotoxin such that the position, or positions, is replaced by any other amino acid. This may be accomplished by targeting a region or regions of the protein for mutagenesis by any number of established mutagenic techniques, including those procedures relevant to the present invention. Such techniques include site-specific mutagenesis (Kunkle, 1985; Kunkle et al., 1987), DNA shuffling (Stemmer, 1994), and PCRTM overlap extension (Horton et al., 1989). Since amino acids situated at or near the surface of a protein are likely responsible for its interaction with other proteinaceous or non-proteinaceous moieties, they may serve as "target" regions for mutagenesis. Such surface exposed regions may consist of, but not be limited to, surface exposed amino acid residues within the active toxin fragment of the protein and include the inter-α-helical or inter-β-strand "loop" -regions of δ-endotoxins that separate a-helices within domain 1 and β-strands within domain 2 and domain 3. Such procedures may favorably change the protein's biochemical and biophysical characteristics or its mode of action as outlined in the Section 1. These include, but are not limited to: 1) improved crystal formation, 2) improved protein stability or reduced protease degradation, 3) improved insect membrane receptor recognition and binding, 4) improved oligomerization or channel formation in the insect midgut endothelium, and 5) improved insecticidal activity or insecticidal specificity due to any or all of the reasons stated above.

2.1 Crystal Protein Transgenes and Transgenic Plants

In yet another aspect, the present invention provides methods for producing a transgenic plant which expresses a nucleic acid segment encoding the novel chimeric crystal proteins of the present invention. The process of producing transgenic plants is well-known in the art. In general, the method comprises transforning a suitable host cell with a DNA segment which contains a promoter operatively linked to a coding region that encodes a *B. thuringiensis* Cry1Ac-1F or Cry1Ab-1F, Cry1Ac-1C, or a Cry1Ab-1Ac-1F chimeric crystal protein. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant crystal protein expressed in a particular transgenic cell, the invention also provides for the expression of crystal protein antisense mRNA. The use of antisense mRNA as a means of controlling or decreasing the amount of a given protein of interest in a cell is well-known in the art.

Another aspect of the invention comprises a transgenic plant which express a gene or gene segment encoding one or more of the novel polypeptide compositions disclosed herein. As used herein, the term "transgenic plant" is intended to refer to a plant that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression. The construction and expression of synthetic *B. thuringiensis* genes in plants has been described in detail in U.S. Pat. Nos. 5,500,365 and 5,380,831 (each specifically incorporated herein by reference).

It is contemplated that in some instances the genome of a transgenic plant of the present invention will have been augmented through the stable introduction of one or more cry1Ac-1F, cry1Ab-1F, cry1Ac-1C, or cry1Ab-1Ac-1F transgenes, either native, synthetically-modified, or further mutated. In some instances, more than one transgene will be incorporated into the genome of the transformed host plant cell. Such is the case when more than one crystal proteinencoding DNA segment is incorporated into the genome of such a plant. In certain situations, it may be desirable to have one, two, three, four, or even more *B. thuringiensis* crystal proteins (either native or recombinantly-engineered) incorporated and stably expressed in the transformed transgenic plant.

A preferred gene, such as those disclosed in SEQ ID NO:9, SEQ ID NO:11, SEQ ID NO:13, SEQ ID NO:25, SEQ ID NO:27, SEQ ID NO:29, and SEQ ID NO:33 which may be introduced includes, for example, a crystal protein-encoding a DNA sequence from bacterial origin, and particularly one or more of those described herein which are obtained from Bacillus spp. Highly preferred nucleic acid sequences are those obtained from *B. thuringiensis*, or any of those sequences which have been genetically engineered to decrease or increase the insecticidal activity of the crystal protein in such a transformed host cell.

Means for transforming a plant cell and the preparation of a transgenic cell line are well-known in the art, and are discussed herein. Vectors, plasmids, cosmids, yeast artificial chromosomes (YACs) and nucleic acid segments for use in transforming such cells will, of course, generally comprise either the operons, genes, or gene-derived sequences of the present invention, either native, or synthetically-derived, and particularly those encoding the disclosed crystal proteins. These DNA constructs can further include structures such as promoters, enhancers, polylinkers, or even gene sequences which have positively- or negatively-regulating activity upon the particular genes of interest as desired. The DNA segment or gene may encode either a native or modified crystal protein, which will be expressed in the resultant recombinant cells, and/or which will impart an improved phenotype to the regenerated plant. Nucleic acid sequences optimized for expression in plants have been disclosed in Intl. Pat. Appi. Publ. No. WO 93/07278 (specifically incorporated herein by reference).

Such transgenic plants may be desirable for increasing the insecticidal resistance of a monocotyledonous or dicotyledonous plant, by incorporating into such a plant, a transgenic DNA segment encoding Cry1Ac-1F and/or Cry1Ac-1C, and/or Cry1Ab-1F and/or Cry1Ab-1Ac-1F crystal protein(s) which possess broad-insect specificity. Particularly preferred plants such as grains, including but not limited to corn, wheat, oats, rice, maize, and barley; cotton; soybeans and other legumes; trees, including but not limited to ornamentals, shrubs, fruits, nuts; vegetables, turf and pasture grasses, berries, citrus, and other crops of commercial interest; such as garden crops and/or houseplants, succulents, cacti, and flowering species.

In a related aspect, the present invention also encompasses a seed produced by the transformed plant, a progeny from such seed, and a seed produced by the progeny of the original transgenic plant, produced in accordance with the above process. Such progeny and seeds will have a stably crystal protein transgene stably incorporated into its genome, and such progeny plants will inherit the traits afforded by the introduction of a stable transgene in Mendelian fashion. All such ansgenic plants having incorporated into their genome transgenic DNA segments encoding one or more chimeric crystal proteins or polypeptides are aspects of this invention.

2.2 Crystal Protein Screening and Immunodetection Kits

The present invention contemplates methods and kits for screening samples suspected of containing crystal protein polypeptides or crystal protein-related polypeptides, or cells producing such polypeptides. Exemplary proteins include those disclosed in SEQ ID NO:10, SEQ ID NO:12, SEQ ID NO:14, SEQ ID NO:26, SEQ ID NO:28, SEQ ID NO:30, and SEQ ID NO:34. Said kit can contain a nucleic acid segment or an antibody of the present invention. The kit can contain reagents for detecting an interaction between a sample and a nucleic acid or antibody of the present invention. The provided reagent can be radio-, fluorescently- or enzymatically-labeled. The kit can contain a known radiolabeled agent capable of binding or interacting with a nucleic acid or antibody of the present invention.

The reagent of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media, a test plate having a plurality of wells, or a microscope slide. When the reagent provided is a dry powder, the powder can be reconstituted by the addition of a suitable solvent, that may be provided.

In still further embodiments, the present invention concerns immunodetection methods and associated kits. It is proposed that the crystal proteins or peptides of the present invention may be employed to detect antibodies having reactivity therewith, or, alternatively, antibodies prepared in accordance with the present invention, may be employed to detect crystal proteins or crystal protein-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either a crystal protein or peptide or a crystal protein-related peptide or antibody sought to be detected, as the case may be, may be employed. It is contemplated that such embodiments may have application in the titering of antigen or antibody samples, in the selection of hybridomas, and the like. In related embodiments, the present invention contemplates the preparation of kits that may be employed to detect the presence of crystal proteins or related peptides and/or antibodies in a sample. Samples may include cells, cell supernatants, cell suspensions, cell extracts, enzyme fractions, protein extracts, or other cell-free compositions suspected of containing crystal proteins or peptides. Generally speaking, kits in accordance with the present invention will include a suitable crystal protein, peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

2.3 ELISAs and Immunoprecipitation

ELISAs may be used in conjunction with the invention. In an ELISA assay, proteins or peptides incorporating crystal protein antigen sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hours, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

Following formation of specific immunocomplexes between the test sample and the bound antigen, and subsequent washing, the occurrence and even amount of immunocomplex formation may be determined by subjecting same to a second antibody having specificity for the firs. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS-Tween®).

After incubation with the second enzyme-tagged antibody, and subsequent to washing to remove unbound material, the amount of label is quantified by incubation with a chromogenic substrate such as urea and bromocresol purple or 2,2'-azino-di-( 3-ethyl-benzthiazoline)-6-sulfonic acid (ABTS) and $H_2O_2$, in the case of peroxidase as the enzyme label. Quantitation is then achieved by measuring the degree of color generation, e.g, using a visible spectra spectrophotometer.

The anti-crystal protein antibodies of the present invention are particularly useful for the isolation of other crystal protein antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g. enzyme-substrate pairs.

2.4 Western Blots

The compositions of the present invention will find great use in immunoblot or western blot analysis. The anti-peptide antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

2.5 Epitopic Core Sequences

The present invention is also directed to protein or peptide compositions, free from total cells and other peptides, which comprise a purified protein or peptide which incorporates an epitope that is immunologically cross-reactive with one or more anti-crystal protein antibodies. In particular, the invention concerns epitopic core sequences derived from Cry proteins or peptides.

As used herein, the term "incorporating an epitope(s) that is immunologically cross-reactive with one or more anti-crystal protein antibodies" is intended to refer to a peptide or protein antigen which includes a primary, secondary or tertiary structure similar to an epitope located within a crystal protein or polypeptide. The level of similarity will generally be to such a degree that monoclonal or polyclonal antibodies directed against the crystal protein or polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of Cry immunodominant epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 8 to about 20 amino acids in length, and more preferably about 8 to about 15 amino acids in length. It is proposed that shorter antigenic crystal protein-derived peptides will provide advantages in certain circumstances, for example, in the preparation of immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to crystal proteins, and in particular Cry and Cry-related sequences. These epitopic core sequences are identified herein in particular aspects as hydrophilic regions of the particular polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on the crystal protein-directed antibodies disclosed herein. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequence The smallest useful core sequence anticipated by the present disclosure would generally be on the order of about 8 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar® software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquotted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at about 4° C., or more preferably, frozen. Of course, where the peptides are stored in a lyophilized or powdered state, they may be stored virtually indefinitely, e.g, in metered aliquots that may be rehydrated with a predetermined amount of water (preferably distilled) or buffer prior to use.

2.6 Nucleic Acid Segments Encoding Crystal Protein Chimeras

The present invention also concerns DNA segments, both native, synthetic, and mutagenized, that can be synthesized, or isolated from virtually any source, that are free from total genomic DNA and that encode the novel chimeric peptides disclosed herein. DNA segments encoding these peptide species may prove to encode proteins, polypeptides, subunits, functional domains, and the like of crystal protein-related or other non-related gene products. In addition these DNA segments may be synthesized entirely in vitro using methods that are well-known to those of skill in the art.

As used herein, the term "DNA segment" refers to a DNA molecule that has been isolated free of total genomic DNA of a particular species. Therefore, a DNA segment encoding a crystal protein or peptide refers to a DNA segment that contains crystal protein coding sequences yet is isolated away from, or purified free from, total genomic DNA of the species from which the DNA segment is obtained, which in the instant case is the genome of the Gram-positive bacterial genus, Bacillus, and in particular, the species of Bacillus known as *B. thuringiensis*. Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified crystal protein-encoding gene refers to a DNA segment which may include in addition to peptide encoding sequences, certain other elements such as, regulatory sequences, isolated substantially away from other naturally occurring genes or proteinencoding sequences. In this respect, the term "gene" is used for simplicity to refer to a functional protein-, polypeptide- or peptide-encoding unit. As will be understood by those in the art, this functional term includes both genomic sequences, operon sequences and smaller engineered gene segments that express, or may be adapted to express, proteins, polypeptides or peptides.

"Isolated substantially away from other coding sequences" means that the gene of interest, in this case, a gene encoding a bacterial crystal protein, forms the significant part of the coding region of the DNA segment, and that the DNA segment does not contain large portions of naturally-occurring coding DNA, such as large chromosomal fragments or other functional genes or operon coding regions. Of course, this refers to the DNA segment as originally isolated, and does not exclude genes, recombinant genes, synthetic linkers, or coding regions later added to the segment by the hand of man.

In particular embodiments, the invention concerns isolated DNA segments and recombinant vectors incorporating DNA sequences that encode a Cry peptide species that includes within its amino acid sequence an amino acid sequence essentially as set forth in SEQ ID NO:10, SEQ ID NO:12, SEQ ID NO:14, SEQ ID NO:26, SEQ ID NO:28, SEQ ID NO:30, SEQ ID NO:34.

The term "a sequence essentially as set forth in SEQ ID NO:10, SEQ ID NO:12, SEQ ID NO:14, SEQ ID NO:26, SEQ ID NO:28, SEQ ID NO:30, or SEQ ID NO:34" means that the sequence substantially corresponds to a portion of the sequence of either SEQ ID NO:10, SEQ ID NO:12, SEQ ID NO:14, SEQ ID NO:26, SEQ ID NO:28, SEQ ID NO:30, or SEQ ID NO:34 and has relatively few amino acids that are not identical to, or a biologically functional equivalent of, the amino acids of any of these sequences. The term "biologically functional equivalent" is well understood in the art and is further defined in detail herein (e.g., see Illustrative Embodiments). Accordingly, sequences that have between about 70% and about 80%, or more preferably between about 81% and about 90%, or even more preferably between about 91% and about 99% amino acid sequence identity or functional equivalence to the amino acids of SEQ ID NO:10, SEQ ID NO:12, SEQ ID NO:14, SEQ ID NO:26, SEQ ID NO:28, SEQ ID NO:30, or SEQ ID NO:34 will be sequences that are "essentially as set forth in SEQ ID NO:10, SEQ ID NO:12, SEQ ID NO:14, SEQ ID NO:26, SEQ ID NO:28, SEQ ID NO:30, or SEQ ID NO:34."

It will also be understood that amino acid and nucleic acid sequences may include additional residues, such as additional N- or C-terminal amino acids or 5' or 3' sequences, and yet still be esstially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch encoding either of the peptide sequences disclosed in SEQ ID NO:10, SEQ ID NO:12, SEQ ID NO:14, SEQ ID NO:26, SEQ ID NO:28, SEQ ID NO:30, or SEQ ID NO:34, or that are identical to or complementary to DNA sequences which encode any of the peptides disclosed in SEQ ID NO:10, SEQ ID NO:12 SEQ ID NO:14, SEQ ID NO:26, SEQ ID NO:28, SEQ ID NO:30, or SEQ ID NO:34, and particularly those DNA segments disclosed in SEQ ID NO:9, SEQ ID NO:11, SEQ ID NO:13, SEQ ID NO:25, SEQ ID NO:27, SEQ ID NO:29, or SEQ ID NO:33. For example, DNA sequences such as about 14 nucleotides, and that are up to about 10,000, about 5,000, about 3,000, about 2,000, about 1,000, about 500, about 200, about 100, about 50, and about 14 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–4,000; 3,000–5,000; and up to and including sequences of about 10,000 nucleotides and the like.

It will also be understood that this invention is not limited to the particular nucleic acid sequences which encode peptides of the present invention, or which encode the amino acid sequences of SEQ ID NO:10, SEQ ID NO:12, SEQ ID NO:14, SEQ ID NO:26, SEQ ID NO:28, SEQ ID NO:30, or SEQ ID NO:34, including those DNA sequences which are particularly disclosed in SEQ ID NO:9, SEQ ID NO:11 SEQ ID NO:13, SEQ ID NO:25, SEQ ID NO:27, SEQ ID NO:29, or SEQ ID NO:33. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically-functional, equivalent peptides. Such sequences may arise as a consequence of codon redundancy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a fill length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein.

2.7 Recombinant Vectors and Protein Expression

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a crystal protein or peptide in its natural environment. Such promoters may include promoters nor mally associated with other genes, and/or promoters isolated from any bacterial, viral, eukaryotic, or plant cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the Pichia expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of crystal peptides or epitopic core regions, such as may be used to generate anti-crystal protein antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences which comprise contiguous amino acid sequences from SEQ ID NO:10, SEQ ID NO:12 SEQ ID NO:14, SEQ ID NO:26, SEQ ID NO:28, SEQ ID NO:30, or SEQ ID NO:34; or any peptide epitope encoded by the nucleic acid sequences of SEQ ID NO:9, SEQ ID NO:11, SEQ ID NO:13, SEQ ID NO:25, SEQ ID NO:27, SEQ ID NO:29, SEQ ID NO:33.

Methods for the recombinant expression of crystal proteins and vectors useful in the expression of DNA constructs encoding crystal proteins are described in Intl. Pat. Appl. Publ. No. WO 95/02058, specifically incorporated herein by reference.

2.8 Recombinant Host Cells

TABLE 2

STRAINS DEPOSITED WITH NRRL

| STRAIN | PLASMID | ACCESSION NUMBER | DEPOSIT DATE |
|---|---|---|---|
| EG11063 | pEG1068 | B-21579 | June 26, 1996 |
| EG11074 | pEG1077 | B-21580 | June 26, 1996 |
| EG11091 | pEG1092 | B-21780 | May XX, 1997 |
| EG11092 | pEG1093 | B-21635 | November 14, 1996 |
| EG11735 | pEG365 | B-21581 | June 26, 1996 |
| EG11751 | pEG378 | B-21636 | November 14, 1996 |
| EG11768 | pEG381 | B-21781 | May XX, 1997 |

2.9 DNA Segments as Hybridization Probes and Primers

In addition to their use in directing the expression of crystal proteins or peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment of SEQ ID NO:9, SEQ ID NO:11, SEQ ID NO:13, SEQ ID NO:25, SEQ ID NO:27, SEQ ID NO:29, or SEQ ID NO:33 will find particular utility. Also, nucleic acid segments which encode at least a 6 amino acid contiguous sequence from SEQ ID NO:10, SEQ ID NO:12, SEQ ID NO:14, SEQ ID NO:26, SEQ ID NO:28, SEQ ID NO:30, or SEQ ID NO:34, are also preferred. Longer contiguous identical or complementary sequences, e.g., those of about 20, 30, 40, 50, 100, 200, 500, 1000, 2000, 5000, 10000 etc. (including all intermediate lengths and up to and including full-length sequences will also be of use in certain embodiments.

The ability of such nucleic acid probes to specifically hybridize to crystal protein-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10–14, 15–20, 30, 50, or even of 100–200 nucleotides or so, identical or complementary to DNA sequences of SEQ ID NO:9, SEQ ID NO:11, SEQ ID NO:13, SEQ ID NO:25, SEQ ID NO:27, SEQ ID NO:29, or SEQ ID NO:33, are particularly contemplated as hybridization probes for use in, e.g., Southern and Northern blotting. Smaller fragments will generally find use in hybridization embodiments, wherein the length of the contiguous complementary region may be varied, such as between about 10–14 and about 100 or 200 nucleotides, but larger contiguous complementarity stretches may be used, according to the length complementary sequences one wishes to detect.

Of course, fragments may also be obtained by other techniques such as, e.g., by mechanical shearing or by restriction enyme digestion. Small nucleic acid segments or fragments may be readily prepared by, for example, directly synthesizing the fragment by chemical means, as is commonly practiced using an automated oligonucleotide synthesizer. Also, fagments may be obtained by application of nucleic acid reproduction technology, such as the PCR™ technology of U.S. Pat. Nos. 4,683,195 and 4,683,202 (each specifically incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating crystal protein-encoding DNA segments. Detection of DNA segments via hybridization is well-known to those of skill in the art, and the teachings of U.S. Pat. Nos. 4,965,188 and 5,176,995 (each specifically incorporated herein by reference) are exemplary of the methods of hybridization analyses. Teachings such as those found in the texts of Maloy et al., 1994; Segal 1976; Prokop, 1991; and Kuby, 1994, are particularly relevant.

Of course, for some applications, for example, where one desires to prepare mutants employing a mutant primer strand hybridized to an underlying template or where one seeks to isolate crystal protein-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

2.10 Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. In particular embodiments of the invention, mutated crystal proteins are contemplated to be usefull for increasing the insecticidal activity of the protein, and consequently increasing the insecticidal activity andlor expression of the recombinant transgene in a plant cell. The amino acid changes may be achieved by changing the codons of the DNA sequence, according to the codons given in Table 3.

TABLE 3

| Amino Acid | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (p.4); threonine (−7); serine (−8); trtyptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, ie., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As retailed in U.S. Pat. No. 4,554,101, the following hydrophilicity values have been assigred to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take variots of the foregoing characteristics into consideration are well known to those of skill in th. art and include: arginine and lysine; glutamate and aspartate; serine and threonine; glutamine and asparagine; and valine, leucine and isoleucine.

2.11 Site-Specific Mutagenesis

Site-specific mutagenesis is a technique usefull in the preparation of individual peptides, or biologically functional equivalent proteins or peptides, through specific mutageneis of the underlying DNA. The technique further provides a ready ability to prepare aid test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a placmid to a phage.

In general, site-directed mutagenesis in accordance herewith is performed by first obtaining a single-stranded vector or melting apart of two strands of a double stranded vector wh.ch includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wierein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

2.12 Crystal Protein Compositions as Insecticides and Methods of Use

The inventors contemplate that the chimeric crystal protein compositions disclosed herein will find particular utility as insecticides for topical and/or systemic application to field crops, grasses, fruits and vegetables, and ornamental plants. In a preferred embodiment, the bioinsecticide composition comprises an oil flowable suspension of bacterial cells which expresses a novel crystal protein disclosed herein. Preferably the cells are *B. thuringiensis* cells, however, any such bacterial host cell expressing the novel nucleic acid segments disclosed herein and producing a crystal protein is contemplated to be useful, such as *B. megaterium, B. subtilis, E. coli*, or Pseudomonas spp.

In another important embodiment, the bioinsecticide composition comprises a water dispersible granule. This granule comprises bacterial cells which expresses a novel crystal protein disclosed herein. Preferred bacterial cells are *B. thuringiensis* cells, however, bacteria such as *B. megaterium, B. subtilis, E. coli*, or Pseudomonas spp. cells transformed with a DNA segment disclosed herein and expressing the crystal protein are also contemplated to be useful.

In a third important embodiment, the bioinsecticide composition comprises a wettable powder, dust, pellet, or collodial concentrate. This powder comprises bacterial cells which expresses a novel crystal protein disclosed herein. Preferred bacterial cells are *B. thuringiensis* cells, however, bacteria such as *B. megaterium, B. subtilis, E. coli*, or Pseudomonas spp. cells tnansformed with a DNA segment disclosed herein and expressing the crystal protein are also contemplated to be useful. Such dry forms of the insecticidal compositions may be formulated to dissolve immediately upon wetting, or alternatively, dissolve in a controlled-release, sustained-release, or other time-dependent manner.

In a fourth important embodiment, the bioinsecticide composition comprises an aqueous sispension of bacterial cells such as those described above which express the crystal protein. Such aqueous suspensions may be provided as a concentrated stock solution which is diluted prior to application, or alternatively, as a diluted solution ready-to-apply.

For these methods involving application of bacterial cells, the cellular host containing the crystal protein gene(s) may be grown in any convenient nutrient medium, where the DNA construct provides a selective advantage, providing for a selective medium so that substantially all or all of the cells retain the *B. thuringiensis* gene. These cells may then be harvested in accordance with conventional ways. Alternatively, the cells can bex treated prior to harvesting.

When the insecticidal compositions comprise intact *B. thuringiensis* cells expressing the protein of interest, such bacteria may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, suspensions, emulsifiable concentrates, or the like. The ingredients may include rheological agents, surfactants, emulsifiers, dispersant, or polymers.

Alternatively, the novel chimeric Cry proteins may be prepared by recombinant bacterial expression systems in vitro and isolated for subsequent field application. Such protein may be either in crude cell lysates, suspensions, colloids, etc., or alternatively may be purified, refined, buffered, and/or further processed, before formulating in an active biocidal formulation. Likewise, under certain circumstances, it may be desirable to isolate cristals and/or spores from bacterial cultures expressing the crystal protein and apply solutions, suspensions, or collodial preparations of such crystals and/or spores as the active bioinsecticidal composition.

Regardless of the method of application, the amount of the active component(s) are applied at an insecticidally-effective amount, which will vary depending on such factors as, for example, the specific coleopteran insects to be controlled, the specific plant or crop to be treated, the environmental conditions, and the method, rate, and quantity of application of the insecticidally-active composition.

The insecticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, dessicated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable catiier" covers all adjuvants, e.g., inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, e.g., by homogeneously mixing, blending and/or grinding the insecticidal composition with suitable adjuvants using conventional formulation, techniques.

The insecticidal compositions of this invention are applied to the environment of the target coleopteran insect, typically onto the foliage of the plant or crop to be protected, by conventional methods, preferably by spraying. The strength and duration of insecticidal application will be set with regard to conditions specific to the particular pest(s), crop(s) to be treated and particular environmental conditions. The proportional ratio of active ingredient to carrier will naturally depend on the chemical nature, solubility, and stability of the insecticidal composition, as well as the particular formulation contemplated.

Other application techniques, e.g., dusting, sprinkling, soaking, soil injection, seed coating, seedling coating, spraying, aerating, misting, atomizing, and the like, are also feasible and may be required under certain circumstances such as e.g., insects that cause root or stalk infestation, or for application to delicate vegetation or ornamental plants. These application procedures are also well-known to those of skill in the art.

The insecticidal composition of the invention may be employed in the method of the invention singly or in combination with other compounds, including and not limited to other pesticides. The method of the invention may also be used in conjunction with other treatments such as surfactants, detergents, polymers or time-release formulations. The insecticidal compositions of the present invention may be formulated for either systemic or topical use.

The concentration of insecticidal composition which is used for environmental, systemic, or foliar application will vary widely depending upon the nature of the particular formulation, means of application, environmental conditions, and degree of biocidal activity. Typically, the bioinsecticidal composition will be present in the applied formulation at a concentration of at least about 0.5% by weight and may be up to and including about 99% by weight. Dry formulations of the compositions may be from about 0.5% to about 99% or more by weight of the composition, while liquid formulations may generally comprise from about 0.5% to about 99% or more of the active ingredient by weight. Formulations which comprise intact bacterial cells will generally contain from about $10^4$ to about $10^{12}$ cells/mg.

The insecticidal formulation may be administered to a particular plant or target area in one or more applications as needed, with a typical field application rate per hectare ranging on the order of from about 50 g to about 500 g of active ingredient, or of from about 500 g to about 1000 g, or of from about 1000 g to about 5000 g or more of active ingredient.

2.13 Antibody Compositions and Methods for Producing

In particular embodiments, the inventors contemplate the use of antibodies, either monoclonal or polyclonal which bind to the crystal proteins disclosed herein. Means for preparing and characterizing antibodies are well known in the art (See, e.g., Harlow and Lane, 1988; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiinide and bis-biazotized benzidine.

As is also well known in the art, the immunogenicity of a particular immunogen compsition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to admnister the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265 (specifically incorporated herein by reference). Typically, this technique involves immunizing a suitable animal with a selected immunogen composition, e.g., a purified or partially purified crystal protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B lymphocytes from the immunized anmal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag 41, Sp210-Ag14, FO, NSO/U, MPC-11, MPC-11X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and, Milstein, 1975; 1976), and those using polyethylene glycol (PEG), such as 37% (vol./vol.) PEG, (Gefter et al., 1977). The use of electrically induced fusion methods is also appropriate (Goding, 1986, pp. 71–74).

Fusion procedures usually produce viable hybrids at low frequencies, about $1\times10^{-6}$ to $1\times10^{-8}$. However, this does not pose a problem, as the viable, fused hybrids are differentiated from the parental, unised cells (particularly the unflised myeloma cells that would normally continue to divide indefinitely) by culturing in a selective medium. The selective medium is generally one that contains an agent that blocks the de novo synthesis of nucleotides in the tissue culture media Exemplary and preferred agents ares aniinopterin, methotrexate, and azaserne. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supematants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fssed cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifigation and various chromatographic methods such as HPLC or affinity chromatography.

3. BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Figure 1B:
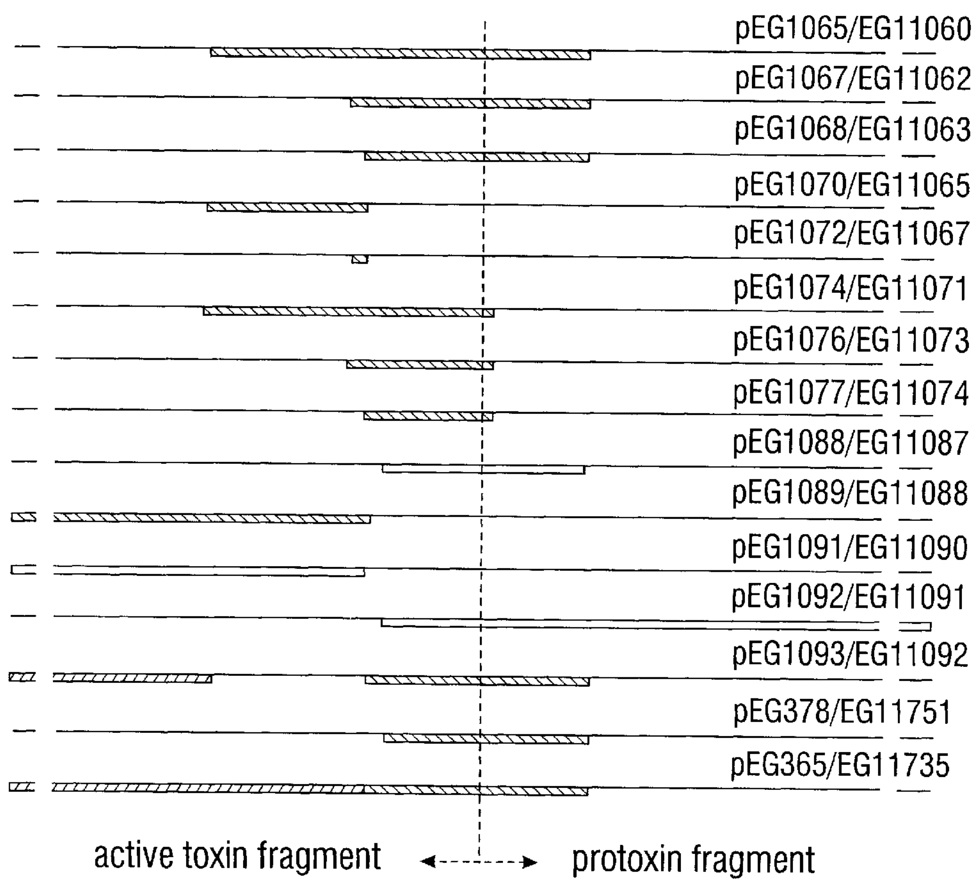

FIG. 1. The wild-type δ-endotoxins and the relevant restriction sites that were used to construct the hybrid δ-endotoxins pertinent to the invention are diagrammed in FIG. 1A. Only the DNA encoding the δ-endotoxin that is contained on the indicated plasmid (identified by the "pEG" prefix) is shown. The *B. thuringiensis* strains containing the indicated plasmids are identified by the "EG" prefix. The hybrid δ-endotoxins described in the invention are diagrammed in FIG. 1B and are aligned with the wild-type δ-endotoxins in FIG. 1A.

Figure 2:
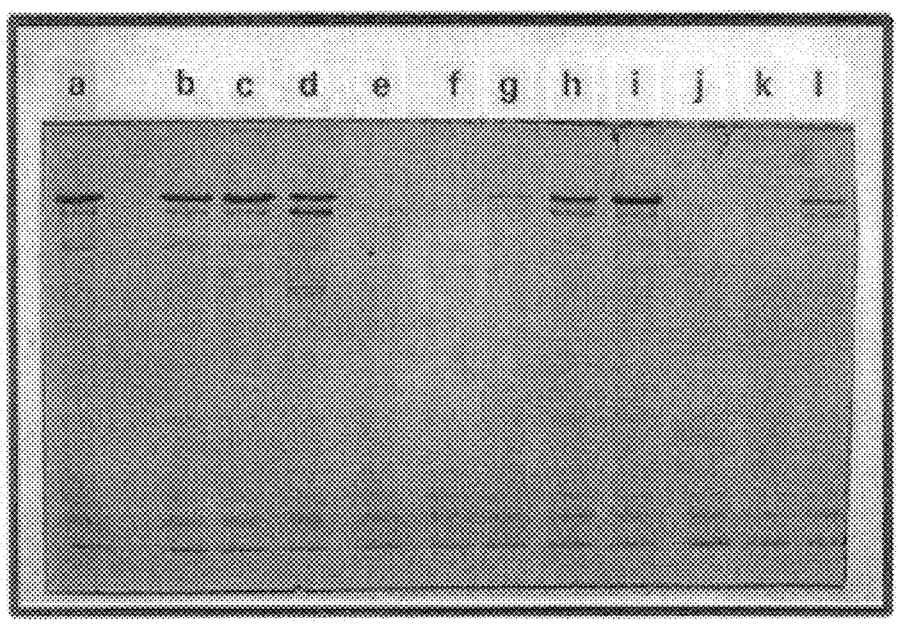

FIG. 2. An equal amount of each washed sporulated *B. thuringiensis* culture was analyzed by SDS-PAGE. Lane a: control Cry1Ac producing *B. thuringiensis* strain EG11070, b: EG11060, c: EG11062, d: EG11063, e: EG11065, f: EG11067, g: EG11710, h: EG11073, i: EG11074, j: EG11088, k: EG11090, and l: EG11091.

Figure 3:
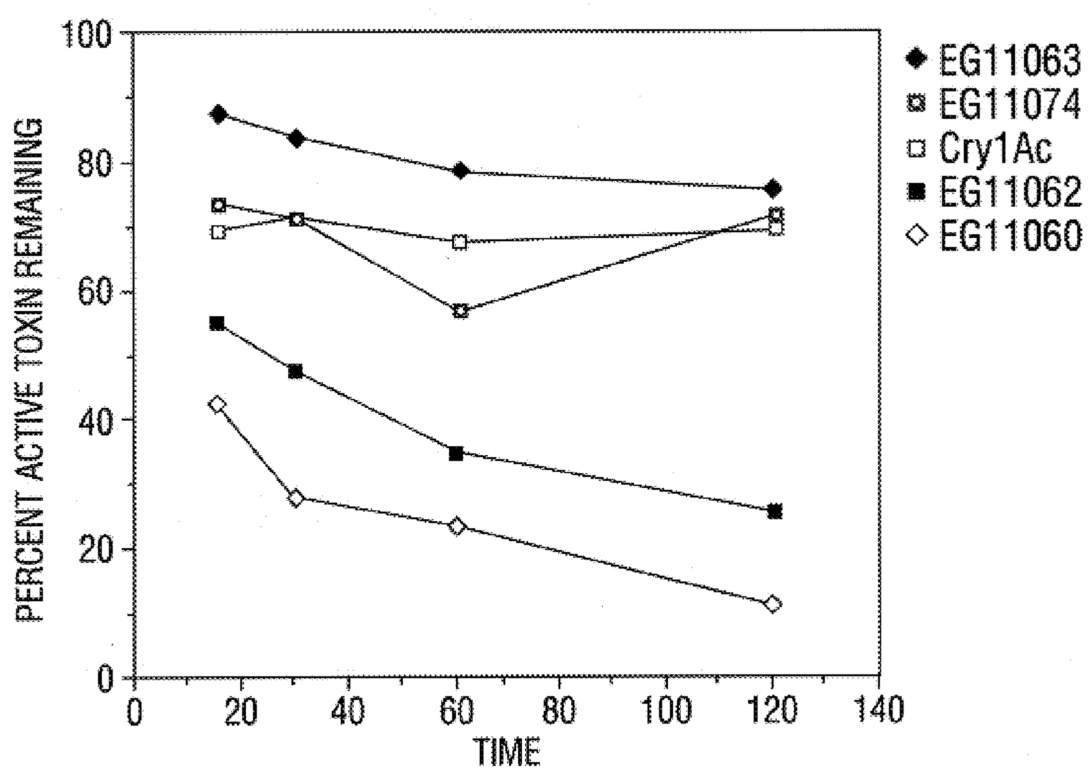

FIG. 3. Solubilized hybrid &endotoxins were exposed to trypsin for 0, 15, 30, 60, and 120 minutes. The resulting material was analyzed by SDS-PAGE. The amount of active δ-endotoxin fragment remaining was quantitated by scanning densitometry using a Molecular Dynamics model 300A densitometer. The percent active toxm remaining was plotted versus time. Wild-type Cry1Ac δ-endotoxin (open box) served as the control.

Figure 4:
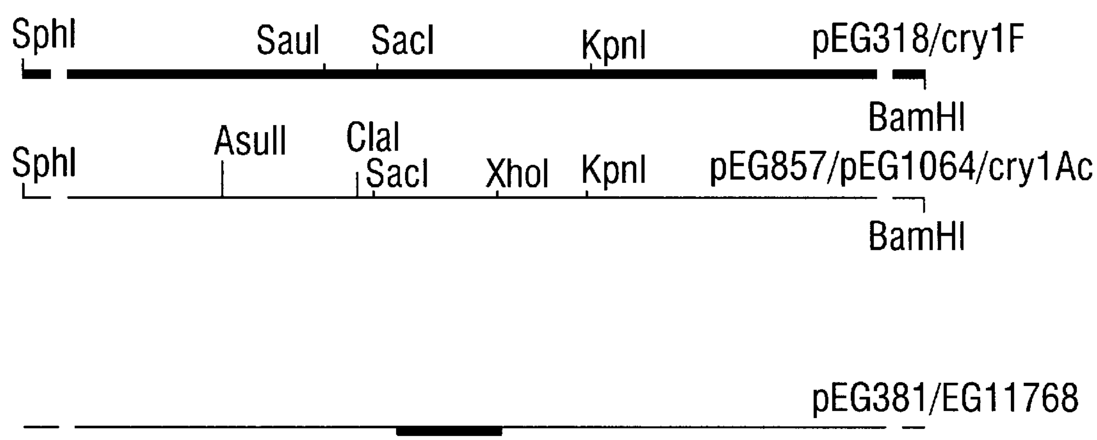

FIG. 4. Schematic diagrams of the wild-type toxins and the relevant restriction sites that were used to construct the hybrid δ-endotoxin encoded by pEG381 and expressed in EG11768. Only the DNA encoding the δ-endotoxin that is contained on the indicated plasmid (identified by the "pEG" prefix) is shown.

4. BRIEF DESCRIPTION OF THE SEQUENCES

SEQ ID NO:1 is oligonucleotide primer A.

SEQ ID NO:2 is oligonucleotide primer B.

SEQ ID NO:3 is oligonucleotide primer C.

SEQ ID NO:4 is oligonucleotide primer D.

SEQ ID NO:5 is oligonucleotide primer E.

SEQ ID NO:6 is oligonucleotide primer F.

SEQ ID NO:7 is oligonucleotide primer G.

SEQ ID NO:8 is oligonucleotide primer H.

SEQ ID NO:9 is the nucleotide and deduced amino acid sequences of the EG11063 hybrid δ-endotoxin.

SEQ ID NO:10 denotes in the three-letter abbreviation form, the amino acid sequence for the hybrid δ-endotoxin specified in SEQ ID NO:9.

SEQ ID NO:11 is the nucleotide and deduced amino acid sequences of the EG11074 hybrid δ-endotoxin.

SEQ ID NO:12 denotes in the three-letter abbreviation form, the amino acid sequence for the hybrid δ-endotoxin specified in SEQ ID NO:11.

SEQ ID NO:13 is the nucleotide and deduced amino acid sequences of the EG11735 hybrid δ-endotoxin.

SEQ ID NO:14 denotes in the three-letter abbreviation form, the amino acid sequence for the hybrid δ-endotoxin specified in SEQ ID NO:13.

SEQ ID NO:15 is the 5' exchange site for pEG1065, pEG1070, and pEG1074.

SEQ ID NO:16 is the 5' exchange site for pEG1067, pEG1072, and pEG1076.

SEQ ID NO:17 is the 5' exchange site for pEG1068, pEG1077, and pEG365.

SEQ ID NO:18 is the 5' exchange site for pEG1088 and pEG1092.

SEQ ID NO:19 is the 5' exchange site for pEG1089 and the 3' exchange site for pEG1070 and pEG1072.

SEQ ID NO:20 is the 5' exchange site for pEG1091.

SEQ ID NO:21 is the 3' exchange site for pEG1065, pEG1067, pEG1068, pEG1093, pEG378, and pEG365.

SEQ ID NO:22 is the 3' exchange site for pEG1088.

SEQ ID NO:23 is oligonucleotide Primer I.

SEQ ID NO:24 is oligonucleotide Primer J.

SEQ ID NO:25 is the nucleic acid sequence and deduced amino acid sequence of the hybrid crystal protein-encoding gene of EG11092.

SEQ ID NO:26 is the three-letter abbreviation form of the amino acid sequence of the hybrid crystal protein produced by strain EG11092 encoded by SEQ ID NO:25.

SEQ ID NO:27 is the nucleic acid sequence and the deduced amino acid sequence of the hybrid crystal protein-encoding gene of EG11751.

SEQ ID NO:28 is the three-letter abbreviation form of the amino acid sequence of the hybrid crystal protein produced by strain EG11751 encoded by SEQ ID NO:27.

SEQ ID NO:29 is the nucleic acid sequence and the deduced amino acid sequence of the hybrid crystal protein-encoding gene of EG11091.

SEQ ID NO:30 is the three-letter abbreviation form of the amino acid sequence of the hybrid crystal protein produced by stain EG11091 encoded by SEQ D NO:29.

SEQ ID NO:31 is oligonucleotide primer K.

SEQ ID NO:32 is the 5' exchange site for pEG378 and pEG381.

SEQ ID NO:33 is the nucleic acid sequence and the deduced amino acid sequence of the hybrid crystal protein-encoding gene of EG11768.

SEQ ID NO:34 denotes in the three-letter abbreviation form, the amino acid sequence of the hybrid crystal protein produced by strain EG11768 encoded by SEQ ID NO:33.

SEQ ID NO:35 is the 3' exchange site for pEG1074, pEG1076, pEG1077 and pEG381.

5. DESCRIPTION OF ILLUSTRATIVE EMBODIMENTS

5.1 Methods for Culturing *B. Thuringiensis* to Produce Cry Proteins

The *B. thuringiensis* strains described herein may be cultured using standard known media and fermentation techniques. Upon completion of the fermentation cycle, the bacteria may be harvested by first separating the *B. thuringiensis* spores and crystals from the fermentation broth by means well known in the art. The recovered *B. thuringiensis* spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against Lepidoptera, e.g., caterpillars.

5.2 Recombinant Host Cells for Expression of Cry Genes

The nucleotide sequences of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the sites of lepidopteran insects where they will proliferate and be ingested by the insects. The results is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the *B. thuringiensis* toxin.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility or toxicity to a manmmalian host. As hosts, of particular interest will be the prokaryotes and the lower eukaryotes, such as fungi. Illustrative prokaryotes, both Gram-negative and Gram-positive, include Enterobacteriaceae, such as Escherichia, Erwinia, Shigella, Salmonella, and Proteus; Bacillaceae; Rhizobiceae, such as Rhizobium; Spirillaceae, such as photobactenum, Zymomonas, Serratia, Aeromonas, Vibrio, Desulfovbrio, Spirillum; Lactobacillaceae; Pseudomonadaceae, such as Pseudomonas and Acetobacter; Azotobacteraceae, Actinomycetales, and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the *B. thuringiensis* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., Streptomyces sp., and the like. Specific organisms include *Pseudomonas aeruginosa, P. fluorescens, Saccharomyces cerevisiae, B. thuringiensis, B. subtilis, E. coli, Streptomyces lividans* and the like.

Treatment of the microbial cell, e.g., a microbe containing the *B. thuringiensis* toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehye; anti-infectives, such as zephiran chloride and cetylpyridinium chloride; alcohols, such as isopropyl and ethanol; various histologic fixatives, such as Lugol's iodine, Bouin's fixative, and Helly's fixatives, (see e.g., Humason, 1967); or a combination of physical (heat) and chemical agents that preserve and prolong the activity of the toxin produced in the cell when the cell is administered to a suitable host. Examples of physical means are short wavelength radiation such as γ-radiation and X-radiation, freezing, UV irradiation, lyophilization, anid the like. The cells employed will usually be intact and be substantially in the proliferative form when treated, rather than in a spore form, although in some instances spores may be employed.

Where the *B. thuringiensis* toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Bacillus, Pseudomonas, Erwinia, Serratia, Klebsiella, Zanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodobacter sphaeroides, Xanthomonas campestris, Rhizobium melioti, Alcaligenes eutrophus*, and *Azotobacter vinlandii*; and phytosphere yeast species such as *Rhodotorula rubra, R. glutinis, R. marina, R. aurantiaca, Cryplococcus albidus, C. diffluens, C. laurentii, Saccharomyces rosei, S. pretoriensis, S. cerevisiae, Sporobolomyces roseus, S. odorus, Klhyveromyces veronae*, and *Aureobasidium pollulans.*

5.3 Definitions

The following words and phrases have the meanings set forth below.

Broad-Spectrum: refers to a wide range of insect species.

Broad-Spectrum Insecticidal Activity: toxicity towards a wide range of insect species.

Expression: The combination of intracellular processes, including transcription and translation undergone by a coding DNA molecule such as a structural gene to produce a polypeptide.

Insecticidal Activity: toxicity towards insects.

Insecticidal Specificity: the toxicity exhibited by a crystal protein towards multiple insect species.

Intraorder Specificity: the toxicity of a particular crystal protein towards insect species within an Order of insects (e.g., Order Lepidoptera).

Interorder Specificity: the toxicity of a particular crystal protein towards insect species of different Orders (e.g., Orders Lepidoptera and Diptera).

$LC_{50}$: the lethal concentration of crystal protein that causes 50% mortality of the insects treated.

$LC_{95}$: the lethal concentration of crystal protein that causes 95% mortality of the insects treated.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g., plant protoplast or explant).

Structural Gene: A gene that is expressed to produce a polypeptide.

Transformation: A process of introducing an exogenous DNA sequence (e g., a vector, a recombinant DNA molecule) into a cell or protoplast in which that exogenous DNA is incorporated into a chromosome or is capable of autonomous replication.

Transformed Cell: A cell whose DNA has been altered by the introduction of an exogenous DNA molecule into that cell.

Transgene: An exogenous gene which when introduced into the genome of a host cell through a process such as transformation, electroporation, particle bombardment, and the like, is expressed by the host cell and integrated into the cells genome such that the trait or traits produced by the expression of the tansgene is inherited by the progeny of the transformed cell.

Transgenic Cell: Any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

Transgenic Plant: A plant or progeny thereof derived from a transformed plant cell or protoplast, wherein the plant DNA contains an introduced exogenous DNA molecule not originally present in a native, non-trarsgenic plant of the same strain. The tenms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a tansgenic plant, and that usage will be followed herein.

Vector: A DNA molecule capable of replication in a host cell and/or to which another DNA segment can be operatively linked so as to bring about replication of the attached segment. A plasmid is an exemplary vector.

5.4 Probes and Primers

In another aspect, DNA sequence information provided by the invention allows for the preparation of relatively short DNA (or RNA) sequences having the ability to specifically hybridize to gene sequences of the selected polynucleotides disclosed herein. In these aspects, nucleic acid probes of an appropriate length are prepared based on a considuation of a selected crystal protein gene sequence, e.g., a sequence such as that shown in SEQ ID NO:9, SEQ ID NO:11, SEQ ID NO:13, SEQ ID NO:25, SEQ ID NO:27, SEQ ID NO:29, or SEQ ID NO:33. The ability of such nucleic acid probes to specifically hybridize to a crystal protein-encoding gene sequence lends them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a crystal protein gene from *B. thuringiensis* using PCR™ technology. Segments of related crystal protein genes from other species may also be amplified by PCT™ using such primers.

To provide certain of the advantages in accordance with the present invention, a preferred nucleic acid sequence employed for hybridization studies or assays includes sequences that are complementary to at least a 14 to 30 or so long nucleotide stretch of a crystal protein-encoding sequence, such as that shown in SEQ ID NO:9, SEQ ID NO:11, SEQ ID NO:13, SEQ ID NO:25, SEQ ID NO:27, SEQ ID NO:29, or SEQ ID NO:33. A size of at least 14 nucleotides in length helps to ensure that the fragment will be of sufficient length to form a duplex molecule that is both stable and selective. Molecules having complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments may be readily prepared by, for example, directly synthesizing the fragment by chemical means, by application of nucleic acid reproduction technology, such as the PCR™ technology of U.S. Pat. Nos. 4,683,195, and 4,683,202 (each specifically incorporated herein by reference), or by excising selected DNA fragments from recombinant plasmids containing appropriate inserts and suitable restriction sites.

5.5 Expression Vectors

The present invention contemplates an expression vector comprising a polynucleotide of the present invention. Thus, in one embodiment an expression vector is an isolated and purified DNA molecule comprising a promoter operatively linked to an coding region that encodes a polypeptide of the present invention, which coding region is operatively linked to a transcription-terminating region, whereby the promoter drives the transcription of the coding region.

As used herein, the term "operatively linked" means that a promoter is connected to an coding region in such a way that the transcription of that coding region is controlled and regulated by that promoter. Means for operatively linking a promoter to a coding region are well known in the art.

Promoters that function in bacteria are well known in the art. Exemplary and preferred promoters for the Bacillus crystal proteins include the sigA, sigE, and sigK gene promoters. Alternatively, the native, mutagenized, or recombinant crystal protein-encoding gene promoters themselves can be used.

Where an expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, constitutive as described (Poszkowski et al., 1989; Odell et al., 1985), and temporally regulated, spatially regulated, and spatiotemporally regulated (Chau et al., 1989).

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, or tissue-specific or developmentally specific promoters affecting dicots or monocots.

Where the promoter is a near-constitutive promoter such as CaMV 35S, increases in polypeptide expression are found in a variety of transformed plant tissues (e.g., callus, leaf, seed and root). Alternatively, the effects of transformation can be directed to specific plant tissues by using plant integrating vectors containing a tissue-specific promoter.

An exemplary tissue-specific promoter is the lectin promoter, which is specific for seed tissue. The Lectin protein in soybean seeds is encoded by a single gene (Le1) that is only expressed during seed maturation and accounts for about 2 to about 5% of total seed mRNA. The lectin gene and seed-specific promoter have been fully characterized and used to direct seed specific expression in transgenic tobacco plants (Vodkin et al., 1983; Lindstrom et al., 1990.)

An expression vector containing a coding region that encodes a polypeptide of interest is engineered to be under control of the lectin promoter and that vector is introduced into plants using, for example, a protoplast transformation method (Dhir et al., 1991). The expression of the polypeptide is directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Exemplary tissue-specific promoters are corn sucrose synthetase 1 (Yang et al., 1990), corn alcohol dehydrogenase 1 (Vogel et al., 1989), corn light harvesting complex (Simpson, 1986), corn heat shock protein (Odell et al., 1985), pea small subunit RuBP carboxylase (Poulsen et al., 1986; Cashmore et al., 1983), Ti plasmid mannopine synthase (Langridge et al., 1989), Ti plasmid nopaline synthase (Langridge et al., 1989), petunia chalcone isomerase (Van Tunen et al., 1988), bean glycine rich protein 1 (Keller et al., 1989), CAMV 35s transcript (Odell et al., 1985) and Potato patatin (Wenzler et al., 1989). Preferred promoters are the cauliflower mosaic virus (CaMV 35S) promoter and the S-E9 small subunit RuBP carboxylase promoter.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors usefil for expression of genes in higher plants are well known in the art and include vectors derived from the tumor-inducing (Ti) plasmid of *Agrobacterium tumefaciens* described (Rogers et al., 1987). However, several other plant integrating vector systems are known to function in plants including pCaMVCN transfer control vector described (Fromm et al., 1985). pCaMVCN (available from Pharmacia, Piscataway, N.J.) includes the cauliflower mosaic virus CaMV 35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotnansferase II (nptII) and nopaline synthase 3N non-translated region described (Rogers et al., 1988).

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,769,061 and 4,757,011 (each of which is specifically incorporated herein by reference). Those vectors can be modified to include a coding sequence in accordance with the present invention.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to confer insecticidal activity to a cell is preferably a chimeric *B. thuringiensis* crystal protein-encoding gene. In preferred embodiments, such a polypeptide has the amino acid residue sequence of SEQ ID NO:10, SEQ ID NO:12, SEQ ID NO:14, SEQ ID NO:26, SEQ ID NO:28, SEQ ID NO:30, or SEQ ID NO:34; or a functional equivalent of one or more of those sequences. In accordance with such embodiments, a coding region comprising the DNA sequence of SEQ ID NO:9, SEQ ID NO:11, SEQ ID NO:13, SEQ ID NO:25, SEQ ID NO:27, SEQ ID NO:29, or SEQ ID NO:33 is also preferred.

5.6 Transformed or Transgenic Plant Cells

A bacterium, a yeast cell, or a plant cell or a plant transformed with an expression vector of the present invention is also contemplated. A transgenic bacterium, yeast cell, plant cell or plant derived from such a transformed or taansgenic cell is also contemplated. Means for transforming bacteria and yeast cells are well known in the art. Typically, means of transformation are similar to those well known means used to transform other bacteria or yeast such as *E. coli* or *S. cerevisiae.*

Methods for DNA transformation of plant cells include Agrobacterium-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as infection by *A. tamefaciens* and related Agrobacterium, direct delivery of DNA such as, for example, by PEG-mediated transfonnation of protoplasts (Ominilleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham and van der Eb, 1973); (2) physical methods such as microinjection (Capecchi, 1980), electroporation (Wong and Neumann, 1982; Fromm et al., 1985) and the gene gun (Johnston and Tang, 1994; Fynan et al., 1993); (3) viral vectors (Clapp, 1993; Lu et al., 1993; Eglitis and Anderson, 1988a; 1988b); and (4) receptor-mediated mechanisms (Curiel et al., 1991; 1992; Wagner et al., 1992).

5.6.1 Electroporation

The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation, is well-known to those of skill in the art. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding. To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

5.6.2 Microprojectile Bombardment

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

An advantage of microprojectile bombardment, in addition to it being an effective means of reproducibly stably transforming monocots, is that neither the isolation of protoplasts (Cristou et al., 1988) nor the susceptibility to Agrobacterium infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with corn cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium.

Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by moditying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

The methods of particle-mediated transformation is well-known to those of skill in the art. U.S. Pat. No. 5,015,580 (specifically incorporated herein by reference) describes the transformation of soybeans using such a technique.

5.6.3 Agrobacterium-Mediated Transfer

Agrobacterium-mediated transfer is a widely applicable system for introducing genes into plant cells because the DNA can be introduced into whole plant tissues, thereb bypassing the need for regeneration of an intact plant from a protoplast. The use of Agrobactenum-mediated plant integrating vectors to introduce DNA into plant cells is well known in the art. See, for example, the methods described (Fraley et al., 1985; Rogers et al., 1987). The genetic engineering of cotton plants using Agrobacterium-mediated transfer is described in U.S. Pat. No. 5,004,863 (specifically incorporated herein by reference), while the transformation of lettuce plants is described in U.S. Pat. No. 5,349,124 (specifically incorporated herein by reference). Further, the integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987).

Modern Agrobacterium transformation vectors are capable of replication in *E. coli* as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant strains where Agrobacterium-mediated transformation is efficient, it is the method of choice because of the facile and defined nature of the gene transfer.

Agrobacterium-mediated transformation of leaf disks and other tissues such as cotyledons and hypocotyls appears to be limited to plants that Agrobacterium naturally infects. Agrobacterium-mediated transformation is most efficient in dicotyledonous plants. Few monocots appear to be natural hosts for Agrobacterium, although transgenic plants have been produced in asparagus using Agrobacterium vectors as described (Bytebier et al., 1987). Therefore, cormnercially important cereal grains such as rice, corns and wheat must usually be transformed using alternative methods. However, as mentioned above, the transformation of asparagus using Agrobacterium can also be achieved (see, e.g., Bytebier et al., 1987).

A transgenic plant formed using Agrobacterium transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

More preferred is a transgenic plant that is homozygous for the added structural gene; i.e., a trarsgenic plant that contains two added genes, one gene at the same locus on each chromosome of a chromosome pair. A homozygous transgenic plant can be obtained by sexually mating (selfing) an independent segregant trarsgenic plant that contains a single added gene, germinating some of the seed produced and analyzing the resulting plants produced for enhanced carboxylase activity relative to a control (native, non-transgenic) or an independent segregant tmnsgenic plant.

It is to be understood that two different tmnsgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-tnansgenic plant are also contemplated.

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Fromm et al., 1985; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts are described (see, e.g., Fujimura et al., 1985; Toriyama et al, 1986; Yamada et al., 1986; Abdullah et al., 1986).

To transform plant strains that cannot be successfully regenerated from protoplasts, other ways to introduce DNA into intact cells or tissues can be utilized. For example, regeneration of cereals from immature embryos or explants can be effected as described (Vasil, 1988). In addition, "particle gun" or high-velocity microprojectile technology can be utilized (Vasil, 1992).

Using that latter technology, DNA is carried through the cell wall and into the cytoplasm on the surface of small metal particles as described (Klein et al., 1987; Klein et al., 1988; McCabe et al., 1988). The metal particles penetrate through several layers of cells and thus allow the transformation of cells within tissue explants.

5.7 Production of Insect-Resistant Transcenic Plants

Thus, the amount of a gene coding for a polypeptide of interest (i.e., a bacterial crystal protein or polypeptide having insecticidal activity against one or more insect species) can be increased in plant such as corn by transforming those plants using particle bombardment methods Haddock et al., 1991). By way of example, an expression vector containing a coding region for a *B. thuringiensis* crystal protein and an appropriate selectable marker is transformed into a suspension of embryonic maize (corn) cells using a particle gun to deliver the DNA coated on microprojectiles. Transgenic plants are enregenerated from transformed embryonic calli that express the disclosed insecticidal crystal proteins. Particle bombardment has been used to successfully transform wheat (Vasil et al., 1992).

DNA can also be introduced into plants by direct DNA transfer into pollen as described (Zhou et al., 1983; Hess, 1987; Luo et al., 1988). Expression of polypeptide coding genes can be obtained by injection of the DNA into reproductive organs of a plant as described (Pena et al., 1987). DNA can also be injected directly into the cells of immature embryos and the rehydration of desiccated embryos as described (Neuhaus et al, 1987; Benbrook et al., 1986).

The development or regeneration of plants from either single plant protoplasts or various explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by Agrobacterium from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983). In particular, U.S. Pat. No. 5,349,124 (specification incorporated herein by reference) details the creation of genetically transformed lettuce cells and plants resulting therefrom which express hybrid crystal proteins conferring insecticidal activity against Lepidopteran larvae to such plants.

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A transgenic plant of this invention thus has an increased amount of a coding region (e.g., a cry gene) that encodes one or more of the Chimeric Cry polypeptides disclosed herein. A preferred transgenic plant is an independent segregant and can transnit that gene and its activity to its progeny. A more preferred transgenic plant is homozygous for that gene, and transmits that gene to all of its offspring on sexual mating. Seed from a transgenic plant may be grown in the field or greenhouse, and resulting sexually mature trnnsgenic plants are self-pollinated to generate true breeding plants. The progeny from these plants become true breeding lines that are evaluated for, by way of example, increased insecticidal capacity against Coleopteran insects, preferably in the field, under a range of environmental conditions. The inventors contemplate that the present invention will fmnd particular utility in the creation of trarsgenic corn, soybeans, cotton, wheat, oats, barley, other grains, vegetables, fruits, fruit trees, berries, turf grass, ornamentals, shrubs and trees.

6. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

6.1 Example 1

Construction of Hybrid *B. Thuringiensis* δ-Endotoxins

The *B. thuringiensis* shuttle vectors pEG853, pEG854, and pEG857 which are used in the present invention have been described (Baum et al., 1990). pEG857 contains the Cry1Ac gene cloned into pEG853 as an SphI-BamHI DNA fragment. pEG1064 was constructed in such a way that the KpnI site within the cry1Ac gene was preserved and the KpnI site in the pEG857 multiple cloning site (MCS) was eliminated. This was accomplished by sequentially subjecting pEG857 DNA to limited KpnI digestion so that only one KpnI site is cut, filling in the KpnI 5' overhang by Klenow fragment of DNA polymerase I to create blunt DNA ends, and joining the blunt ends of DNA by T4 DNA ligase. pEG318 contains the cry1Fgene (Chanbers et al., 1991) cloned into the XhoI site of pEG854 as an XhoI-SalI DNA fragment. pEG315 contains the cry1C gene from strain EG6346 (Chambers et al., 1991) cloned into the XhoI-BamHI sites of pEG854 as a SalI-BamHI DNA fragment.

FIG. 1A shows a schematic representation of the DNA encoding the complete cry1Ac, cry1Ab, cry1C, and cry1F genes contained on pEG854/pEG1064, pEG20, pEG315, and pEG318, respectively. Unique restriction sites that were used in constructing certain hybrid genes are also shown. FIG. 1B shows a schematic representation of hybrid genes pertaining to the present invention. In some cases standard PCT™ amplification with mutagenic oligonucleotide primers were used to incorporate appropriate restrictions sites into DNA fragments used for hybrid gene construction. Certain hybrid gene constructions could not be accomplished by restriction fragment subcloning. In those instances, PCR™ overlap extension (POE) was used to construct the desired hybrid gene (Horton el al., 1989). The following oligonucleotide primers (purchased from Integrated DNA Technologies Inc., Coralville, Iowa) were used:

Primer A: 5'-GGATAGCACTCATCAAAGGTACC-3' (SEQ ID NO:1)

Primer B: 5'-GAAGATATCCAATTCGAACAGTTTCCC-3' (SEQ ID NO:2)

Primer C: 5'-CATATTCTGCCTCGAGTGTTGCAGTAAC-3' (SEQ ID NO:3)

Primer D: 5'-CCCGATCGGCCGCATGC-3' (SEQ ID NO:4)

Primer E: 5'-CATTGGAGCTCTCCATG-3' (SEQ ID NO:5)

Primer F: 5'-GCACTACGATGTATCC-3' (SEQ ID NO:6)

Primer G: 5'-CATCGTAGTGCAACTCTTAC-3' (SEQ ID NO:7)

Primer H: 5'-CCAAGAAAATACTAGAGCTCTTGTTAAAAAGG-TGTTCC-3' (SEQ ID NO:8)

Primer I: 5'-ATTTGAGTAATACTATCC-3' (SEQ ID NO:23)

Primer J: 5'-ATTACTCAAATACCATTGG-3' (SEQ ID NO:24)

Primer K: 5'-TCGTTGCTCTGTTCCCG-3' (SEQ ID NO:31)

The plasmids described in FIG. 1B containing the hybrid δ-endotoxin genes pertinent to this invention are described below. Isolation or purification of DNA fragments generated by restriction of plasmid DNA, PCR™ amplification, or POE refers to the sequential application of agarose-TAE gel electrophoresis and use of the Geneclean Kit (Bio 101) following the manufacturer's recommendation. pEG1065 was constructed by PCR™ amplification of the cry1F DNA fragent using primer pair A and B and pEG318 as the DNA template. The resulting PCR™ product was isolated, cut with AsuII and KpnI, and used to replace the corresponding AsuII-KpnI DNA fragment in pEG857. Plasmid pEG1067 was constructed using POE and DNA fragments SauI-KpnI of cry1F and AsuII-ClaI of cry1Ac that were isolated from pEG318 and pEG857, respectively. The resulting POE product was PCT™ amplified with primer pair A and B, cut with AsuII and KpnI, and used to replace the corresponding AsuII-KpnI fragment in pEG857.

pEG1068 was constructed by replacing the SacI-KpnI DNA fragment of cry1Ac isolated from pEG857 with the corresponding SacI-KpnI DNA fragment isolated from cry1F (pEG318). pEG1070 was constructed by replacing the SacI-KpnI DNA fragment isolated from pEG065 with the corresponding SacI-KpnI DNA fragment isolated from cry1Ac (pEG857). pEG1072 was constructed by replacing the SacI-KpnI DNA fragment isolated from pEG1067 with the corresponding SacI-KpnI DNA fragment isolated from cry1Ac (pEG857) pEG1074, pEG1076, and pEG1077 were constructed by replacing the SphI-XhoI DNA fragment from pEG1064 with the PCT™ amplified SphI-XhoI DNA fragment from pEG1065, pEG1067, pEG1068, respectively, using primer pairs C and D. pEG1089 was constructed by replacing the SphI-SacI DNA fragment of pEG1064 with the isolated and SphI and SacI cut PCT™ product of cry1F that was generated using primer pair D and E and the template pEG318.

pEG1091 was constructed by replacing the SphI-SacI DNA fragment of pEG1064 with the isolated and SphI and SacI cut PCT™ product of cry1C that was generated using primer pair D and H and the template pEG315.

pEG1088 was constructed by POE using a cry1Ac DNA fragment generated using primer pair B and F and a cry1C DNA fragment generated using primer pair A and G. The SacI-KpnI fragment was isolated from the resulting POE product and used to replace the corresponding SacI-KpnI fragment in pEG1064.

pEG365 was constructed by first replacing the SphI-KpnI DNA fragment from pEG1065 with the corresponding cry1Ab DNA fragment isolated from pEG20 to give pEG364. The SacI-KpnI DNA fragment from pEG364 was then replaced with the corresponding cry1F DNA fragent isolated from pEG318.

pEG1092 was constructed by replacing the KpnI-BamHI DNA fragment from pEG1088 with the corresponding DNA fragment isolated from pEG315. pEG1092 is distinct from the cry1Ab/cry1C hybrid δ-endotoxin gene disclosed in Intl. Pat. Appl. Publ. No. WO 95/06730.

pEG1093 was constructed by replacing the SphI-AsuII DNA fragment from pEG1068 with the corresponding SphI-AsuII DNA fragment isolated from pEG20.

pEG378 was constructed by POE using a cry1Ac DNA fragment generated using primer pair B and I using pEG857 as the template and a cry1F DNA fragment generated using primer pair A and J using pEG318 as the template. The resulting POE product was cut with AsuII and KpnI and the resulting isolated DNA fragment used to replace the corresponding AsuII-KpnI DNA fiagment in pEG1064.

pEG381 was constructed by replacing the AsuII-XhoI DNA fragment in pEG1064 with the corresponding AsuII-XhoI DNA fragment isolated from the PCT™ amplification of pEG378 using primer pair C and K.

6.2 Example 2

Production of the Hybrid Toxins in *B. Thuringiensis*

The plasmids encoding the hybrid toxins described in Example 1 were transformed into *B. thuringiensis* as described (Mettus and Macaluso, 1990). The resulting *B. thuringiensis* strains were grown in 50 ml of C-2 medium until the culture was filly sporulated and lysed (approximately 48 hr.). Since crystal formation is a prerequisite for efficient commercial production of δ-endotoxins in *B. thuringiensis*, microscopic analysis was used to identify crystals in the sporulated cultures (Table 4).

TABLE 4

CRYSTAL FORMATION BY THE HYBRID-δ-ENDOTOXINS

| Strain | Plasmid | Parent δ-Endotoxins | Crystal Formation |
|---|---|---|---|
| EG11060 | pEG1065 | Cry1Ac + Cry1F | + |
| EG11062 | pEG1067 | Cry1Ac + Cry1F | + |
| EG11063 | pEG1068 | Cry1Ac + Cry1F | + |
| EG11065 | pEG1070 | Cry1Ac + Cry1F | − |
| EG11067 | pEG1072 | Cry1Ac + Cry1F | − |
| EG11071 | pEG1074 | Cry1Ac + Cry1F | + |

TABLE 4-continued

| CRYSTAL FORMATION BY THE HYBRID-δ-ENDOTOXINS | | | |
|---|---|---|---|
| Strain | Plasmid | Parent δ-Endotoxins | Crystal Formation |
| EG11073 | pEG1076 | Cry1Ac + Cry1F | + |
| EG11074 | pEG1077 | Cry1Ac + Cry1F | + |
| EG11087 | pEG1088 | Cry1Ac + Cry1C | − |
| EG11088 | pEG1089 | Cry1F + Cry1Ac | − |
| EG11090 | pEG1091 | Cry1C + Cry1Ac | − |
| EG11091 | pEG1092 | Cry1Ac + Cry1C | + |
| EG11092 | pEG1093 | Cry1Ab + Cry1Ac + Cry1F | + |
| EG11735 | pEG365 | Cry1Ab + Cry1F + Cry1Ac | + |
| EG11751 | pEG378 | Cry1Ac + Cry1F | + |
| EG11768 | pEG381 | Cry1Ac + Cry1F | + |

The δ-endotoxin production for some of the *B. thuringiensis* strains specified in Table 4 was examined by sodium dodecyl sulfate-polyacrylamide gel electrophoresis (SDS-PAGE) as described by Baum et al., 1990. Equal volume cultures of each *B. thuringiensis* stin were grown in C-2 mediumn until fully sporulated and lysed. The cultures were centrifuged and the spore/crystal pellet was washed twice with equal volumes of distilled deionized water. The final pellet was suspended in half the culture volume of 0.005% Triton X-100®. An equal volume of each washed culture was analyzed by SDS-PAGE as shown in FIG. 2.

The majority of hybrids involving Cry1Ac and Cry1F formed stable crystals in *B. thuringiensis* A notable exception is EG11088 in which the active toxin fragment would be the reciprocal exchange of EG11063. Two of the three hybrids involving Cry1Ac and Cry1C, EG11087 and EG11090, failed to produce crystal in *B. thuringiensis* even though these reciprocal hybrids mimic the activated toxin fragments of crystal-forming EG11063 and EG11074.

Every strain that was examined by SDS-PAGE produced some level of δ-endotoxin. As expected, however, those cultures identified as crystal negative produced very little protein (e.g., lane e: EG11065, lane f: EG11067, lane j: EG11088, and lane k: EG11090). For reference, typical yields from a crystal forming δ-endotoxin is shown for Cry1Ac (lane a). Several hybrid δ-endotoxins produce comparable levels of protein including EG11060 (lane b), EG11062 (lane c), EG11063 (lane d; SEQ ID NO:10), and EG11074 (lane i; SEQ ID NO:12). The data clearly show that efficient hybrid δ-endotoxin production in *B. thuringiensis* is unpredictable and varies depending on the parent δ-endotoxins used to construct the hybrid.

6.3 Example 3

Proteolytic Processing of the Hybrid δ-endotoxins

Proteolytic degradation of the protoxin form of the δ-endotoxin to a stable active toxin occurs once δ-endotoxin crystals are solubilized in the larval midgut. One measure of the potential activity of δ-endotoxins is the stability of the active δ-endotoxin in a proteolytic environment. To test the proteolytic sensitivity of the hybrid δ-endotoxins, solubilized toxin was subjected to trypsin digestion. The δ-endotoxins were purified from sporulated B. thuringiensis cultures and quantified as described (Chambers et al., 1991) Exactly 250 μg of each hybrid δ-endotoxin crystal was solubilized in 30 mM $NaHCO_3$, 10 mM DEr (total volume 0.5 ml). Trypsin was added to the solubilized toxin at a 1:10 ratio. At appropriate time points 50 μl aliquots were removed to 50 μl Laemmli buffer, heated to 100° C. for 3 min., and frozen in a dry-ice ethanol bath for subsequent analysis. The trypsn digests of the solubilized toxins were analyzed by SDS-PAGE and the amount of active δ-endotoxin at each time point was quantified by densitometry. A graphic representation of the results from these studies are shown in FIG. 3.

The wild-type Cry1Ac is rapidly processed to the active δ-endotoxin fragment that is stable for the duration of the study. The hybrid Sendotoxins from EG11063 and EG11074 are also processed to active δ-endotoxin fragments which are stable for the duration of the study. The processing of the EG11063 δ-endotoxin occurs at a slower rate and a higher percentage of this active δ-endotoxin fragment remains at each time point. Although the hybrid δ-endotoxins from EG11060 and EG11062 are process to active δ-endotoxin fragments, these fragments are more susceptible to further cleavage and degrade at various rates during the course of the study. The 5' exchange points between cry1Ac and cry1F for the EG11062 and EG11063 δ-endotoxins result in toxins that differ by only 21 amino acid residues (see FIG. 1). However, the importance of maintaining Cry1Ac sequences at these positions is evident by the more rapid degradation of the EG11062 δ-endotoxin. These data demonstrate that different hybrid δ-endotoxins constructed using the same parental δ-endotoxins can vary significantly in biochemical characteristics such as proteotytic stability.

6.4 Example 4

Bioactivity of the Hybrid δ-endotoxins

*B. thuringiensis* cultures expressing the desired oendotoxin were grown until fully sporulated and lysed and washed as described in Example 2. The δ-endotoxin levels for each culture were quantified by SDS-PAGE as described (Baum et al., 1990). In the case of bioassay screens, a single appropriate concentration of each washed δ-endotoxin culture was topically applied to 32 wells containing 1.0 ml artificial diet per well (surface area of 175 $mm^2$). A single neonate larvae was placed in each of the treated wells and the tray covered by a clear perforated mylar sheet. Larvae mortality was scored after 7 days of feeding and percent mortality expressed as the ratio of the number of dead larvae to the total number of larvae treated, 32.

In the case of $LC_{50}$ determinations (δ-endotoxin concentration giving 50% mortality), δ-endotoxins were purified from the *B. thuringiensis* cultures and quantified as described by Chambers et al. (1991). Eight concentrations of the δ-endotoxins were prepared by serial dilution in 0.005% Triton X-100® and each concentration was topically applied to wells containing 1.0 ml of artificial diet. Larvae mortality was scored after 7 days of feeding (32 larvae for each δ-endotoxin concentration). In all cases the diluent served as the control.

A comparison of the Cry1A/Cry1F hybrid toxins by bioassay screens is shown in Table 5. The hybrid δ-ndotoxins from strains EG11063 and EG11074 maintain the activities of the parental Cry1Ac and Cry1F δ-endotoxins. Furthermore, the hybrid δ-endotoxin from EG11735 maintains the activity of its parental Cry1Ab and Cry1F δ-endotoxins. The δ-endotoxins produce by strains EG11061, EG11062, EG11071, and EG11073 have no insecticidal activity on the insect larvae tested despite 1) being comprised of at least one parental δ-endotoxin that is active against the indicated larvae and 2) forming stable, well-defined crystals in *B. thuringiensis*. These results demonstrate the unpdictable nature of hybrid toxin constructions.

For the data in Table 5. All strains were tested as washed sporulated cultures. For each insect tested, equivalent amnounts of δ-endotoxins were used and insecticidal activity was based on the strain showing the highest percent mortality (++++).

TABLE 5

BIOASSAY SCREENS OF HYBRID CRY1A/CRY1F δ-ENDOTOXINS

| Strain | *S. frugiperda* | *S. exigua* | *H. virescens* | *H. zea* | *O. nubilalis* |
|---|---|---|---|---|---|
| Cry1Ac | – | – | ++++ | ++++ | +++ |
| Cry1F | ++++ | ++ | ++ | ++ | ++ |
| Cry1Ab | ++ | + | +++ | ++ | +++ |
| EG11060 | – | – | – | – | – |
| EG11062 | – | – | – | – | – |
| EG11063 | ++++ | ++++ | +++ | +++ | ++++ |
| EG11071 | – | – | – | – | – |
| EG11073 | – | – | – | – | – |
| EG11074 | ++++ | ++++ | +++ | +++ | ++++ |
| EG11090 | – | +++ | – | – | – |
| EG11091 | ++++ | ++++ | – | – | N.D. |
| EG11092 | ++++ | ++++ | +++ | +++ | N.D. |
| EG11735 | ++++ | ++++ | +++ | +++ | N.D. |
| EG11751 | N.D.[a] | ++++ | N.D. | ++++ | N.D. |

[a]N.D. = not determined.

The δ-endotoxins described in FIG. 1 and that demonstrated insecticidal activity in bioassay screens were tested as purified crystals to determine their $LC_{50}$ (see Table 6). The δ-endotoxins purified from strains EG11063, EG11074, EG11091, and EG11735 all show increased armyworm (*S. frugiperda* and *S. exigua*) activity compared to any of the wild-type δ-endotoxins tested. The EG11063 and EG11074 δ-endotoxins would yield identical active toxin fragments (FIG. 1B) which is evident by their similar $LC_{50}$ values on the insects examined. An unexpected result evident from these data is that a hybrid δ-endotoxin such as EG11063, EG11092, EG11074, EG11735, or EG11751 can retain the activity of their respective parental δ-endotoxins, and, against certain insects such as *S. exigua*, can have activity far better than either parental δ-endotoxin. This broad range of insecticidal activity at doses close to or lower than the parental δ-endotoxins, along with the wild-type level of toxin production (Example 2), make these proteins particularly suitable for production in *B. thuringiensis*. Although the EG11091 derived δ-endotoxin has better activity against *S. frugiperda* and *S. exigua* than its parental δ-endotoxins, it has lost the *H. virescens* and *H. zea* activity attributable to its Cry1Ac parent. This restricted host range along with lower toxin yield observed for the EG11091 δ-endotoxin (Example 2) make it less amenable to production in *B. thuringiensis*.

TABLE 6

$LC_{50}$ VALUES FOR THE PURIFIED HYBRID δ-ENDOTOXIN[A]

| Toxin | *S. frugiperda* | *S. exigua* | *H. virescens* | *H. zea* | *O. nubilalis* |
|---|---|---|---|---|---|
| Cry1Ac | >10000 | >10000 | 9 | 100 | 23 |
| Cry1Ab | 1435 | 4740 | 118 | 400 | 17 |
| Cry1C | >10000 | 490 | >10000 | >10000 | >10000 |
| Cry1F | 1027 | 3233 | 54 | 800 | 51 |
| EG11063 (Cry1Ac/1F) | 550 | 114 | 33 | 80 | 7 |
| EG11074 (Cry1Ac/1F) | 468 | 77 | 25 | 76 | 9 |
| EG11091 (Cry1Ac/1C) | 21 | 21 | 219 | >10000 | N.D.[a] |

[a]N.D. = not determined.

In Table 6, the $LC_{50}$ values are expressed in nanograms of purified δ-endotoxin per well (175 $mm^2$) and are the composite values for 2 to 6 replications. nd=not determined.

TABLE 7

DNA EXCHANGE SITES FOR CRY1 HYBRID δ-ENDOTOXINS

| Plasmid | SEQ ID NO: | 5' Exchange Site | SEQ ID NO: | 3' Exchange Site |
|---|---|---|---|---|
| pEG1065 | 15 | TATCCAATTCGAACGTCATC | 21 | ACTACCAGGTACCTTTGATG |
| pEG1067 | 16 | TTTAGTCATCGATTAAATCA | 21 | ACTACCAGGTACCTTTGATG |
| pEG1068 | 17 | ATAATAAGAGCTCCAATGTT | 21 | ACTACCAGGTACCTTTGATG |
| pEG1070 | 15 | TATCCAATTCGAACGTCATC | 19 | TCATGGAGAGCTCCTATGTT |
| pEG1072 | 16 | TTTAGTCATCGATTAAATCA | 19 | TCATGGAGAGCTCCTATGTT |
| pEG1074 | 15 | TATCCAATTCGAACGTCATC | 35 | TGCAACACTCGAGGCTGAAT |
| pEG1076 | 16 | TTTAGTCATCGATTAAATCA | 35 | TGCAACACTCGAGGCTGAAT |
| pEG1077 | 17 | ATAATAAGAGCTCCAATGTT | 35 | TGCAACACTCGAGGCTGAAT |
| pEG1088 | 18 | TACATCGTAGTGCAACTCTT | 22 | ACTACCGGGTACCTTTGATA |
| pEG1089 | 19 | TCATGGAGAGCTCCTATGTT | — | NA |
| pEG1091 | 20 | TTAACAAGAGCTCCTATGTT | — | NA |
| pEG1092 | 18 | TACATCGTAGTGCAACTCTT | — | NA |
| pEG1093 | — | NDb | 21 | ACTACCAGGTACCTTTGATG |
| pEG365 | 17 | ATAATAAGAGCTCCAATGTT | 21 | ACTACCAGGTACCTTTGATG |
| pEG378 | 32 | TCAAATACCATTGGTAAAAG | 21 | ACTACCAGGTACCTTTGATG |
| pEG381 | 32 | TCAAATACCATTGGTAAAAG | 35 | TGCAACACTCGAGGCTGAAT |

[a]NA = Not Applicable. These hybrid toxins contain only one exchange site as shown in FIG. 1.
[b]ND = Not Distinuishable. The exchange site for these hybrid proteins are identified by DNA sequences that are not distinguishable from either of the parent toxins.

Table 7 describes the DNA surrounding the 5' and 3' exchange points for the hybrid δ-endotoxins which are pertinent to the present invention. As evident by the SEQ ID NO, certain hybrid δ-endotoxins share exchange sites.

To examine the effect of other small changes in the exchange site chosen for hybrid endotoxin construction, the activity of EG11751 and EG11063 on *S. exigua* and *H. zea* were compared (Table 8). The data clearly show that hybrid δ-endotoxin improvements can be made by altering the exchange site between the two parental δ-endotoxins. In this example, the exchange site in the EG11751 δ-endotoxin was moved 75 base pairs 3' compared to the EG11063 δ-endotoxin and results in improved insecticidal activity. Although no significant improvement in *S. exigua* activity is observed between EG11063 and EG11751, a significant improvement in *H. zea* activity of almost 4-fold is observed for EG11751. It is important to note that improvements in hybrid δ-endotoxin bioactivity by altering exchange sites is unpredictable. In the case of EG11062, moving the exchange site 63 base pairs 5' of the EG11063 exchange site abolishes insecticidal activity as shown in Table 7.

TABLE 8

BIOACTIVITY OF EG11063 AND EG11751

| *B. thuringiensis* Strain | $LC_{50}$ Values for Washed Sporulated Cultures | |
|---|---|---|
| | *S. exigua* | *H. zea* |
| EG11063 | 106 | 38 |
| EG11751 | 90 | 10 |

To further examine the effect of changes in the exchange site for hybrid δ-endotoxins, the hybrid δ-endotoxin encoded by pEG381 was compared to those encoded by pEG378 and pEG1068. In this example, the 3' exchange site for the pEG381 encoded hybrid δ-endotoxin was moved 340 base pairs 5' compared to the pEG378 hybrid δ-endotoxin. The data in Table 8 show that this change results in an increase in *S. frugiperda* activity compared to the pEG378 and pEG1066 encoded δ-endotoxins while maintaining the increased activity that was observed for the pEG378 encoded δ-endotoxin over the pEG1068 encoded δ-endotoxin (see Table 7). This result is unexpected since the activated toxin resulting from the proteolysis of the encoded δ-endotoxins from pEG378 and pEG381 should be identical. This example further demonstrates that exchange sites within the protoxin fragment of δ-endotoxins can have a profound effect on insecticidal activity.

TABLE 9

BIOACTIVITY OF TOXINS ENCODED BY pEG378, pEG381 AND pEG1068

| Plasmid | $LC_{50}$ Values for Purified Crystals | | | |
|---|---|---|---|---|
| | *S. frugiperda* | *T. ni* | *H. zea* | *P. xylostella* |
| pEG378 | 464 | 57.7 | 37.5 | 3.02 |
| pEG381 | 274 | 56.0 | 36.6 | 2.03 |
| pEG1068 | 476 | 66.7 | 72.7 | 3.83 |

6.5 Example 5

Activity of the Hybrid Toxins on Additional Pests

The toxins of tie present invention were also assayed against additional pests, including the southwestern corn borer and two pests active against soybean. Toxin proteins were solubilized, added to diet and bioassayed against target pests. The hybrid toxins showed very effective control of all three pests.

TABLE 10

$LC_{50}$ AND $EC_{50}$ RANGES OF HYBRID TOXINS ON SOUTHWESTERN CORN BORER[1,2]

| | EG11063 | EG11074 | EG11091 | EG11751 |
|---|---|---|---|---|
| $LC_{50}$ | 20 | 10–20 | 10–20 | 10–20 |
| $EC_{50}$ | 0.2–2 | 0.2–2 | 0.2–2 | 0.2–2 |

[1]All values are expressed in μg/ml of diet.
[2]SWCB data ranges represent $LC_{50}$ and $EC_{50}$ ranges (as determined by % >1st instar), respectively.

TABLE 11

$LC_{50}$ VALUES OF CHIMERIC CRYSTAL PROTEINS ON SOYBEAN PESTS[1]

| Pest | EG11063 | EG11074 | EG11091 | EG11751 | EG11768 |
|---|---|---|---|---|---|
| Velvetbean caterpillar[1] | 0.9 | 0.6 | 0.3 | 0.1 | 0.06 |
| Soybean looper | 0.9 | 0.8 | 0.6 | 0.7 | 0.2 |

[1]All values are expressed in μg/ml of diet.
[2]Velvetbean caterpillar (*Anticarsia gemmatalis*) and soybean looper (*Psuedoplusi includens*) are both members of the family Noctuidae.

6.6 Example 6

Amino Acid Sequences of the Novel Crystal Proteins 6.6.1 Amino Acid Sequence of the EG11063 Crystal Protein (SEQ ID NO:10)

```
MetAspAsnAsnProAsnIleAsnGluCysIleProTyrAsnCysLeuSerAsnProGluValGluValLeu

GlyGlyGluArgIleGluThrGlyTyrProIleAspIleSerLeuSerLeuThrGlnPheLeuLeuSer

GluPheValProGlyAlaGlyPheValLeuGlyLeuValAspIleIleTrpGlyIlePheGlyProSerGln
```

-continued

TrpAspAlaPheLeuValGlnIleGluGlnLeuIleAsnGlnArgIleGluGluPheAlaArgAsnGlnAla

IleSerArgLeuGluGlyLeuSerAsnLeuTyrGlnIleTyrAlaGluSerPheArgGluTrpGluAlaAsp

ProThrAsnProAlaLeuArgGluGluMetArgIleGlnPheAsnAspMetAsnSerAlaLeuThrThrAla

IleProLeuPheAlaValGlnAsnTyrGlnValProLeuLeuSerValTyrValGlnAlaAlaAsnLeuHis

LeuSerValLeuArgAspValSerValPheGlyGlnArgTrpGlyPheAspAlaAlaThrIleAsnSerArg

TyrAsnAspLeuThrArgLeuIleGlyAsnTyrThrAspTyrAlaValArgTrpTyrAsnThrGlyLeuGlu

ArgValTrpGlyProAspSerArgAspTrpValArgTyrAsnGlnPheArgArgGluLeuThrLeuThrVal

LeuAspIleVAlalaLeuPheProAsnTyrAspSerArgArgTyrProIleArgThrValSerGlnLeuThr

ArgGluIleTyrThrAsnProValLeuGluAsnPheAspGlySerPheArgGlySerAlaGlnGlyIleGlu

ArgSerIleArgSerProHisLeuMetAspIleLeuAsnSerIleThrIleTyrThrAspAlaHisArgGly

TyrTyrTyrTrpSerGlyHisGlnIleMetAlaSerProValGlyPheSerGlyProGluPheThrPhePro

LeuTyrGlyThrMetGlyAsnAlaAlaProGlnGlnArgIleVAlalaGlnLeuGlyGlnGlyValTyrArg

ThrLeuSerSerThrLeuTyrArgArgProPheAsnIleGlyIleAsnAsnGlnGlnLeuSerValLeuAsp

GlyThrGluPheAlaTyrGlyThrSerSerAsnLeuProSerAlaValTyrarGLysSerGlyThrValAsp

SerLeuAspGluIleProProGlnAsnAsnAsnValProProArgGlnGlyPheSerHisArgLeuSerHis

ValSerMetPheArgSerGlyPheSerAsnSerSerValSerIleIleArgAlaProMetPheSerTrpThr

HisArgSerAlaThrProThrAsnThrIleAspProGluArgIleThrGlnIleProLeuValLysAlaHis

ThrLeuGlnSerGlyThrThrValValArgGlyProGlyPheThrGlyGlyAspIleLeuArgArgThrSer

GlyGlyProPheAlaTyrThrIleValAsnIleAsnGlyGlnLeuProGlnArgTyrArgAlaArgIleArg

TyrAlaSerThrThrAsnLeuArgIleTyrValThrValAlaGlyGluArgIlePheAlaGlyGlnPheAsn

LysThrMetAspThrGlyAspProLeuThrPheGlnSerPheSerTyrAlaThrIleAsnThrAlaPheThr

PheProMetSerGlnSerSerPheThrValGlyAlaAspThrPheSerSerGlyAsnGluValTyrIleAsp

ArgPheGluLeuIleProValThrAlaThrPheGluAlaGluTyrAspLeuGluArgAlaGlnLysAlaVal

AsnAlaLeuPheThrSerIleAsnGlnIleGlyIleLysThrAspValThrAspTyrHisIleAspGlnVal

SerAsnLeuValAspCysLeuSerAspGluPheCysLeuAspGluLysArgGluLeuSerGluLysValLys

HisAlaLysArgLeuSerAspGluArgAsnLeuLeuGlnAspProAsnPheLysGlyIleAsnArgGlnLeu

AspArgGlyTrpArgGlySerThrAspIleThrIleGlnArgGlyAspAspValPheLysGluAsnTyrVal

ThrLeuProGlyThrPheAspGluCysTyrProThrTyrLeuTyrGlnLysIleAspGluSerLysLeuLys

AlaPheThrArgTyrGlnLeuArgGlyTyrIleGluAspSerGlnAspLeuGluIleTyrLeuIleArgTyr

AsnAlaLysHisGluThrValAsnValProGlyThrGlySerLeuTrpProLeuSerAlaGlnSerProIle

GlyLysCysGlyGluProAsnArgCysAlaProHisLeuGluTrpAsnProAspLeuAspCysSerCysArg

AspGlyGluLysCysAlaHisHisSerHisHisPheSerLeuAspIleAspValGlyCysThrAspLeuAsn

GluAspLeuGlyValTrpValIlePheLysIleLysThrGlnAspGlyHisAlaArgLeuGlyAsnLeuGlu

PheLeuGluGluLysProLeuValGlyGluAlaLeuAlaArgValLysArgAlaGluLysLysTrpArgAsp

LysArgGluLysLeuGluTrpGluThrAsnIleValTyrLysGluAlaLysGluSerValAspAlaLeuPhe

ValAsnSerGlnTyrAspGlnLeuGlnAlaAspThrAsnIleAlaMetIleHisAlaAlaAspLysArgVal

HisSerIleArgGluAlaTyrLeuProGluLeuSerValIleProGlyValAsnAlaAlaIlePheGluGlu

LeuGluGlyArgIlePheThrAlaPheSerLeuTyrAspAlaArgAsnValIleLysAsnGlyAspPheAsn

AsnGlyLeuSerCysTrpAsnValLysGlyHisValAspValGluGluGlnAsnAsnGlnArgSerValLeu

ValValProGluTrpGluAlaGluValSerGlnGluValArgValCysProGlyArgGlyTyrIleLeuArg

-continued

ValThrAlaTyrLysGluGlyTyrGlyGluGlyCysValThrIleHisGluIleGluAsnAsnThrAspGlu

LeuLysPheSerAsnCysValGluGluGluIleTyrProAsnAsnThrValThrCysAsnAspTyrThrVal

AsnGlnGluGluTyrGlyGlyAlaTyrThrSerArgAsnArgGlyTyrAsnGluAlaProSerValProAla

AspTyrAlaSerValTyrGluGluLysSerTyrThrAspGlyArgArgGluAsnProCysGluPheAsnArg

GlyTyrArgAspTyrThrProLeuProValGlyTyrValThrLysGluLeuGluTyrPheProGluThrAsp

LysValTrpIleGluIleGlyGluThrGluGlyThrPheIleValAspSerValGluLeuLeuLeuMetGlu

Glu 6.6.2 Amino Acid Sequence of the EG11074 Crystal Protein (SEQ ID NO:12)

MetAspAsnAsnProAsnIleAsnGluCysIleProTyrAsnCysLeuSerAsnProGluValGluValLeu

AlaAlaGluArgIleGluThrAlaTyrThrProIleAspIleSerLeuSerLeuThrGlnPheLeuLeuSer

GluPheValProGlyAlaGlyPheValLeuGlyLeuValAspIleIleTrpGlyIlePheGlyProSerGln

TrpAspAlaPheLeuValGlnIleGluGlnLeuIleAsnGlnArgIleGluGluPheAlaArgAsnGlnAla

IleSerArgLeuGluGlyLeuSerAsnLeuTyrGlnIleTyrAlaGluSerPheArgGluTrpGluAlaAsp

ProThrAsnProAlaLeuArgGluGluMetArgIleGlnPheAsnAspMetAsnSerAlaLeuThrThrAla

IleProLeuPheAlaValGlnAsnTyrGlnValProLeuLeuSerValTyrValGlnAlaAlaAsnLeuHis

LeuSerValLeuArgAspValSerValPheGlyGlnArgtrpAlaPheAspAlaAlaThrIleAsnSerArg

TyrAsnAspLeuThrArgLeuIleGlyAsnTyrThrAspTyrAlaValArgTrpTyrAsnThrGlyLeuGlu

ArgValTrpGlyProAspSerArgAspTrpValArgTyrAsnGlnPheArgArgGluLeuThrLeuThrVal

LeuAspIleValAlaLeuPheProAsnTyrAspSerArgArgTyrProIleArgThrValSerGlnLeuThr

ArgGluIleTyrThrAsnProValLeuGluAsnPheAspGlySerPheArgGlySerAlaGlnGlyIleGlu

ArgSerIleArgSerProHisLeuMetAspIleLeuAsnSerIleThrIleTyrThrAspAlaHisArgGly

TyrTyrTyrTrpSerGlyHisGlnIleMetAlaSerProValGlyPheSerGlyProGluPheThrPhePro

LeuTyrGlyThrMetGlyAsnAlaAlaProGlnGlnArgIleValAlaGlnLeuGlyGlnGlyValTyrArg

ThrLeuSerSerThrLeuTyrArgArgProPheAsnIleAlaIleAsnAsnGlnGlnLeuSerValLeuAsp

GlyThrGluPheAlaTyrGlyThrSerSerAsnLeuProSerAlaValTyrArgLysSerGlyThrValAsp

SerLeuAspGluIleProProGlnAsnAsnAsnValProProArgGlnGlyPheSerHisArgLeuSerHis

ValSerMetPheArgSerGlyPheSerAsnSerSerValSerIleIleArgAlaProMetPheSerTrpThr

HisArgSerAlaThrProThrAsnThrIleAspProGluArgIleThrGlnIleProLeuValLysAlaHis

ThrLeuGlnSerGlyThrThrValValArgGlyProGlyPheThrGlyGlyAspIleLeuArgArgThrSer

AlaAlaProPheAlaTyrThrIlevAlAsnIleAsnAlaGlnLeuProGlnArgTyrArgAlaArgIleArg

TyrAlaSerThrThrAsnLeuArgIleTyrValThrValAlaGlyGluArgIlePheAlaGlyGlnPheAsn

LysThrMetAspThrGlyAspProLeuThrPheGlnSerPheSerTyrAlaThrIleAsnThrAlaPheThr

PheProMetSerGlnSerSerPheThrValGlyAlaAspThrPheSerSerGlyAsnGluValTyrIleAsp

ArgPheGluLeuIleProValThrAlaThrLeuGluAlaGluTyrAsnLeuGluArgAlaGlnLysAlaVal

AsnAlaLeuPheThrSerThrAsnGlnLeuGlyLeuLysThrAsnValThrAspTyrHisIleAspGlnVal

SerAsnLeuValThrTyrLeuSerAspGluPheCysLeuAspGluLysArgGluLeuSerGluLysValLys

HisAlaLysArgLeuSerAspGluArgAsnLeuLeuGlnAspSerAsnPheLysAspIleAsnArgGlnPro

GluArgGlyTrpGlyGlySerThrGlyIleThrIleGlnGlyGlyAspAspValPheLysGluAsnTyrVal

-continued

ThrLeuSerGlyThrPheAspGluCysTyrProThrTyrLeuTyrGlnLysIleAspGluSerLysLeuLys

AlaPheThrArgTyrGlnLeuArgGlyTyrIleGluAspSerGlnAspLeuGluIleTyrLeuIleArgTyr

AsnAlaLysHisGluThrvAlAsnValProAlaThrgLySerLeutrpProLeuSerAlaGlnSerProIle

GlyLysCysGlyGluProAsnArgCysAlaProHisLeuGluTrpAsnProAspLeuAspCysSerCysArg

AspGlyGluLysCysAlaHisHisSerHisHisPheSerLeuAspIleAspValGlyCysThrAspLeuAsn

GluAspLeuGlyValTrpValIlePheLysIleLysThrGlnAspGlyHisAlaArgLeuGlyAsnLeuGlu

PheLeuGluGluLysProLeuValGlyGluAlaLeuAlaArgValLysArgAlaGluLysLysTrpArgAsp

LysArgGluLysLeuGluTrpGluThrAsnIleValTyrLysGluAlaLysGluSerValAspAlaLeuPhe

ValAsnSerGlnTyrAspGlnLeuGlnAlaAspThrAsnIleAlaMetIleHisAlaAlaAspLysArgVal

HisSerIleArgGluAlaTyrLeuProGluLeuSerValIleProGlyValAsnAlaAlaIlePheGluGlu

LeuGluGlyArgIlePheThrAlaPheSerLeuTyrAspAlaArgAsnValIleLysAsnGlyAspPheAsn

AsnGlyLeuSerCysTrpAsnValLysGlyHisValAspValGluGluGlnAsnAsnGlnArgSerValLeu

ValValProGluTrpGluAlaGluValSerGlnGluValArgValCysProGlyArgGlyTyrIleLeuArg

ValThrAlaTyrLysGluGlyTyrGlyGluGlyCysValThrIleHisGluIleGluAsnAsnThrAspGlu

LeuLysPheSerAsnCysValGluGluGluIleTyrProAsnAsnThrValThrCysAsnAspTyrThrVal

AsnGlnGluGluTyrGlyGlyAlaTyrThrSerArgAsnArgGlyTyrAsnGluAlaProSerValProAla

AspTyrAlaSerValTyrGluGluLysSerTyrThrAspGlyArgArgGluAsnProCysGluPheAsnArg

GlyTyrArgAspTyrThrProLeuProValGlyTyrValThrLysGluLeuGluTyrPheProGluThrAsp

LysValTrpIleGluIleGlyGluThrGluGlyThrPheIleValAspSerValGluLeuLeuLeuMetGlu

Glu 6.6.3 Amino Acid Sequence of the EG11735 Crystal Protein (SEQ ID NO:14)

MetAspAsnAsnProAsnIleAsnGluCysIleProTyrAsnCysLeuSerAsnProGluValGluValLeu

GlyGlyGluArgIleGluThrGlyTyrThrProIleAspIleSerLeuSerLeuThrGlnPheLeuLeuSer

GluPheValProGlyAlaGlyPheValLeuGlyLeuValAspIleIleTrpGlyIlePheGlyProSerGln

TrpAspAlaPheLeuValGlnIleGluGlnLeuIleAsnGlnArgIleGluGluPheAlaArgAsnGlnAla

IleSerArgLeuGluGlyLeuSerAsnLeuTyrGlnIleTyrAlaGluSerPheArgGluTrpGluAlaAsp

ProThrAsnProAlaLeuArgGluGluMetArgIleGlnPheAsnAspMetAsnSerAlaLeuThrThrAla

IleProLeuPheAlaValGlnAsnTyrGlnValProLeuLeuSerValTyrValGlnAlaAlaAsnLeuHis

LeuSerValLeuArgAspValSerValPheGlyGlnArgTrpGlyPheAspAlaAlaThrIleAsnSerArg

TyrAsnAspLeuThrArgLeuIleGlyAsnTyrThrAspHisAlaValArgTrpTyrAsnThrGlyLeuGlu

ArgValTrpGlyProAspSerArgAspTrpIleArgTyrAsnGlnPheArgArgGluLeuThrLeuThrVal

LeuAspIleValSerLeuPheProAsnTyrAspSerArgThrTyrProIleArgThrValSerGlnLeuThr

ArgGluIleTyrThrAsnProValLeuGluAsnPheAspGlySerPheArgGlySerAlaGlnGlyIleGlu

GlySerIleArgSerProHisLeuMetAspIleLeuAsnSerIleThrIleTyrThrAspAlaHisArgGly

GluTyrTyrTrpSerGlyHisGlnIleMetAlaSerProValGlyPheSerGlyProGluPheThrPhePro

LeuTyrGlyThrMetGlyAsnAlaAlaProGlnGlnArglleValAlaGlnLeuGlyGlnGlyValTyrArg

ThrLeuSerSerThrLeuTyrArgArgProPheAsnIleGlyIleAsnAsnGlnGlnLeuSerValLeuAsp

-continued

GlyThrGluPheAlaTyrGlyThrSerSerAsnLeuProSerAlaValTyrArgLysSerGlyThrValAsp

SerLeuAspGluIleProProGlnasnasnasnValProProArgGlnGlyPheSerHisArgLeuSerHis

ValSerMetPheArgSerGlyPheSerAsnSerSerValSerIleIleArgAlaProMetPheSerTrpThr

HisArgSerAlaThrProThrasnThrIleAspProGluArgIleThrGlnIleProLeuValLysAlaHis

ThrLeuGlnSerGlyThrThrValValArgGlyProGlyPheThrGlyGlyAspIleLeuArgArgThrSer

GlyGlyProPheAlaTyrThrIleValAsnIleAsnGlyGlnLeuProGlnArgTyrArgAlaArgIleArg

TyrAlaSerThrThrAsnLeuArgIleTyrValThrValAlaGlyGluArgIlePheAlaGlyGlnPheAsn

LysThrMetAspThrGlyAspProLeuThrPheGlnSerPheSerTyrAlaThrIleAsnThrAlaPheThr

PheProMetSerGlnSerSerPheThrValGlyAlaAspThrPheSerSerGlyAsnGluValTyrIleAsp

ArgPheGluLeuIleProValThrAlaThrPheGluAlaGluTyrAspLeuGluArgAlaGlnLysAlaVal

AsnAlaLeuPheThrSerIleAsnGlnIleGlyIleLysThrAspValThrAspTyrHisIleAspGlnVal

SerAsnLeuValAspCysLeuSerAspGluPheCysLeuAspGluLysArgGluLeuSerGluLysValLys

HisAlaLysArgLeuSerAspGluArgAsnLeuLeuGlnAspProAsnPheLysGlyIleAsnArgGlnLeu

AspArgGlyTrpArgGlySerThrAspIleThrIleGlnArgGlyAspAspValPheLysGluAsnTyrVal

ThrLeuPrOGlyThrPheAspGluCysTyrProThrTyrLeuTyrGlnLysIleAspGluSerLysLeuLys

AlaPheThrArgTyrGlnLeuArgGlyTyrIleGluAspSerGlnAspLeuGluIleTyrLeuIleArgTyr

AsnAlaLysHisGluThrValAsnValProGlyThrGlySerLeuTrpProLeuSerAlaGlnSerProIle

GlyLysCysGlyGluProAsnArgCysAlaProHisLeuGluTrpAsnProAspLeuAspCysSerCysArg

AspGlyGluLysCysAlaHisHisSerHisHisPheSerLeuAspIleAspValGlyCysThrAspLeuAsn

GluAspLeuGlyValTrpValIlePheLysIleLysThrGlnAspGlyHisAlaArgLeuGlyAsnLeuGlu

PheLeuGluGluLysProLeuValGlyGluAlaLeuAlaArgValLysArgAlaGluLysLysTrpArgAsp

LysArgGluLysLeuGluTrpGluThrAsnIleValTyrLysGluAlaLysGluSerValAspAlaLeuPhe

ValAsnSerGlnTyrAspGlnLeuGlnAlaAspThrAsnIleAlaMetIleHisAlaAlaAspLysArgVal

HisSerIleArgGluAlaTyrLeuProGluLeuSerValIleProGlyValAsnAlaAlaIlePheGluGlu

LeuGluGlyArgIlePheThrAlaPheSerLeuTyrAspAlaArgAsnValIleLysAsnGlyAspPheAsn

AsnGlyLeuSerCysTrpAsnValLysGlyHisValAspValGluGluGlnAsnAsnGlnArgSerValLeu

ValValProGluTrpGluAlaGluValSerGlnGluValArgValCysProGlyArgGlyTyrIleLeuArg

ValThrAlaTyrLysGluGlyTyrGlyGluGlyCysValThrIleHisGluIleGluAsnAsnThrAspGlu

LeuLysPheSerAsnCysValGluGluGluIleTyrProAsnAsnThrValThrCysAsnAspTyrThrVal

AsnGlnGluGluTyrGlyGlyAlaTyrThrSerArgAsnArgGlyTyrAsnGluAlaProSerValProAla

AspTyrAlaSerValTyrGluGluLysSerTyrThrAspGlyArgArgGluAsnProCysGluPheAsnArg

GlyTyrArgAspTyrThrProLeuProValGlyTyrValThrLysGluLeuGluTyrPheProGluThrAsp

LysValTrpIleGluIleGlyGluThrGluGlyThrPheIleValAspSerValGluLeuLeuLeuMetGlu

Glu 6.6.4 Amino Acid Sequence of the EG11092 Crystal Protein (SEQ ID NO:26)

MetAspAsnAsnProAsnIleAsnGluCysIleProTyrAsnCysLeuSerAsnProGluValGluValLeu

GlyGlyGluArgIleGluThrGlyTyrThrProIleAspIleSerLeuSerLeuThrGlnPheLeuLeuSer

GluPheValProGlyAlaGlyPheValLeuGlyLeuValAspIleIleTrpGlyIlePheGlyProSerGln

-continued

TrpAspAlaPheLeuValGlnIleGluGlnLeuIleAsnGlnArgIleGluGluPheAlaArgAsnGlnAla

IleSerArgLeuGluGlyLeuSerAsnLeuTyrGlnIleTyrAlaGluSerPheArgGluTrpGluAlaAsp

ProThrAsnProAlaLeuArgGluGluMetArgIleGlnPheAsnAspMetAsnSerAlaLeuThrThrAla

IleProLeuPheAlaValGlnAsnTyrGlnValProLeuLeuSerValTyrValGlnAlaAlaAsnLeuHis

LeuSerValLeuArgAspValSerValPheGlyGlnArgTrpGlyPheAspAlaAlaThrIleAsnSerArg

TyrAsnAspLeuThrArgLeuIleGlyAsnTyrThrAspHisAlaValArgTrpTyrAsnThrGlyLeuGlu

ArgValTrpGlyProAspSerArgAspTrpIleArgTyrAsnGlnPheArgArgGluLeuThrLeuThrVal

LeuAspIleValSerLeuPheProAsnTyrAspSerArgThrTyrProIleArgThrValSerGlnLeuThr

ArgGluIleTyrThrAsnProValLeuGluAsnPheAspGlySerPheArgGlySerAlaGlnGlyIleGlu

ArgSerIleArgSerProHisLeuMetAspIleLeuAsnSerIleThrIleTyrThrAspAlaHisArgGly

TyrTyrTyrTrpSerGlyHisGlnIleMetAlaSerProValGlyPheSerGlyProGluPheThrPhePro

LeuTyrGlyThrMetGlyAsnAlaAlaProGlnGlnArgIleValAlaGlnLeuGlyGlnGlyValTyrArg

ThrLeuSerSerThrLeuTyrArgArgProPheAsnIleGlyIleAsnAsnGlnGlnLeuSerValLeuAsp

GlyThrGluPheAlaTyrGlyThrSerSerAsnLeuProSerAlaValTyrArgLysSerGlyThrValAsp

SerLeuAspGluIleProProGlnAsnAsnAsnValProProArgGlnGlyPheSerHisArgLeuSerHis

ValSerMetPheArgSerGlyPheSerAsnSerSerValSerIleIleArgAlaProMetPheSerTrpThr

HisArgSerAlaThrProThrAsnThrIleAspProGluArgIleThrGlnIleProLeuValLysAlaHis

ThrLeuGlnSerGlyThrThrValValArgGlyProGlyPheThrGlyGlyAspIleLeuArgArgThrSer

GlyGlyProPheAlaTyrThrIleValAsnIleAsnGlyGlnLeuProGlnArgTyrArgAlaArgIleArg

TyrAlaSerThrThrAsnLeuArgIleTyrValThrValAlaGlyGluArgIlePheAlaGlyGlnPheAsn

LysThrMetAspThrGlyAspProLeuThrPheGlnSerPheSerTyrAlaThrIleAsnThrAlaPheThr

PheProMetSerGlnSerSerPheThrValGlyAlaAspThrPheSerSerGlyAsnGluValTyrIleAsp

ArgPheGluLeuIleProValThrAlaThrPheGluAlaGluTyrAspLeuGluArgAlaGlnLysAlaVal

AsnAlaLeuPheThrSerIleAsnGlnIleGlyIleLysThrAspValThrAspTyrHisIleAspGlnVal

SerAsnLeuValAspCysLeuSerAspGluPheCysLeuAspGluLysArgGluLeuSerGluLysValLys

HisAlaLysArgLeuSerAspGluArgAsnLeuLeuGlnAspProAsnPheLysGlyIleAsnArgGlnLeu

AspArgGlyTrpArgGlySerThrAspIleThrIleGlnArgGlyAspAspValPheLysGluAsnTyrVal

ThrLeuProGlyThrPheAspGluCysTyrProThrTyrLeuTyrGlnLysIleAspGluSerLysLeuLys

AlaPheThrArgTyrGlnLeuArgGlyTyrIleGluAspSerGlnAspLeuGluIleTyrLeuIleArgTyr

AsnAlaLysHisGluThrValAsnValProGlyThrGlySerLeuTrpProLeuSerAlaGlnSerProIle

GlyLysCysGlyGluProAsnArgCysAlaProHisLeuGluTrpAsnProAspLeuAspCysSerCysArg

AspGlyGluLysCysAlaHisHisSerHisHisPheSerLeuAspIleAspValGlyCysThrAspLeuAsn

GluAspLeuGlyValTrpValIlePheLysIleLysThrGlnAspGlyHisAlaArgLeuGlyAsnLeuGlu

PheLeuGluGluLysProLeuValGlyGluAlaLeuAlaArgValLysArgAlaGluLysLysTrpArgAsp

LysArgGluLysLeuGluTrpGluThrAsnIleValTyrLysGluAlaLysGluSerValAspAlaLeuPhe

ValAsnSerGlnTyrAspGlnLeuGlnAlaAspThrAsnIleAlaMetIleHisAlaAlaAspLysArgVal

HisSerIleArgGluAlaTyrLeuProGluLeuSerValIleProGlyValAsnAlaAlaIlePheGluGlu

LeuGluGlyArgIlePheThrAlaPheSerLeuTyrAspAlaArgAsnValIleLysAsnGlyAspPheAsn

AsnGlyLeuSerCysTrpAsnValLysGlyHisValAspValGluGluGlnAsnAsnGlnArgSerValLeu

ValValProGluTrpGluAlaGluValSerGlnGluValArgValCysProGlyArgGlyTyrIleLeuArg

-continued

ValThrAlaTyrLysGluGlyTyrGlyGluGlyCysValThrIleHisGluIleGluAsnAsnThrAspGlu

LeuLysPheSerAsnCysValGluGluGluIleTyrProAsnAsnThrValThrCysAsnAspTyrThrVal

AsnGlnGluGluTyrGlyGlyAlaTyrThrSerArgAsnArgGlyTyrAsnGluAlaProSerValProAla

AspTyrAlaSerValTyrGluGluLysSerTyrThrAspGlyArgArgGluAsnProCysGluPheAsnArg

GlyTyrArgAspTyrThrProLeuProValGlyTyrValThrLysGluLeuGluTyrPheProGluThrAsp

LysValTrpIleGluIleGlyGluThrGluGlyThrPheIleValAspSerValGluLeuLeuLeuMetGlu

Glu 6.6.5 Amino Acid Sequence of the EG11751 Crystal Protein (SEQ ID NO:28)

MetAspAsnAsnProAsnIleAsnGluCysIleProTyrAsnCysLeuSerAsnProGluValGluValLeu

GlyGlnGluArgIleGluThrGlyTyrThrProIleAspIleSerLeuSerLeuThrGlnPheLeuLeuSer

GluPheValProGlyAlaGlyPheValLeuGlyLeuValAspIleIleTrpGlyIlePheGlyProSerGln

TrpAspAlaPheLeuValGlnIleGluGlnLeuIleAsnGlnArgIleGluGluPheAlaArgAsnGlnAla

IleSerArgLeuGluGlyLeuSerAsnLeuTyrGlnIleTyrAlaGluSerPheArgGluTrpGluAlaAsp

ProThrAsnProAlaLeuArgGluGluMetArgIleGlnPheAsnAspMetAsnSerAlaLeuThrThrAla

IleProLeuPheAlaValGlnAsnTyrGlnValProLeuLeuSerValTyrValGlnAlaAlaAsnLeuHis

LeuSerValLeuArgAspValSerValPheGlyGlnArgTrpGlyPheAspAlaAlaThrIleAsnSerArg

TyrAsnAspLeuThrArgLeuIleGlyAsnTyrThrAspTyrAlaValArgTrpTyrAsnThrGlyLeuGlu

ArgValTrpGlyProAspSerArgAspTrpValArgTyrAsnGlnPheArgArgGluLeuThrLeuThrVal

LeuAspIleValAlaLeuPheProAsnTyrAspSerArgArgTyrProIleArgThrValSerGlnLeuThr

ArgGluIleTyrThrAsnProValLeuGluAsnPheAspGlySerPheArgGlySerAlaGlnGlyIleGlu

ArgSerIleArgSerProHisLeuMetAspIleLeuAsnSerIleThrIleTyrThrAspAlaHisArgGly

TyrTyrTyrTrpSerGlyHisGlnIleMetAlaSerProValGlyPheSerGlyProGluPheThrPhePro

LeuTyrGlyThrMetGlyAsnAlaAlaProGlnGlnArgIleValAlaGlnLeuGlyGlnGlyValTyrArg

ThrLeuSerSerThrLeuTyrArgArgProPheAsnlleGlyIleAsnAsnGlnGlnLeuSerValLeuAsp

GlyThrGluPheAlaTyrGlyThrSerSerAsnLeuProSerAlaValTyrArgLysSerGlyThrValAsp

SerLeuAspGluIleProProGlnAsnAsnAsnValProProArgGlnGlyPheSerHisArgLeuSerHis

ValSerMetPheArgSerGlyPheSerAsnSerSerValSerIleIleArgAlaProMetPheSerTrpIle

HisArgSerAlaGluPheAsnAsnIleIleAlaSerAspSerIleThrglnIleProLeuValLysAlaHis

ThrLeuGlnSerGlyThrThrValValArgGlyProGlyPheThrGlyGlyAspIleLeuArgArgThrSer

GlyGlyProPheAlaTyrThrIleValAsnIleAsnGlyGlnLeuProGlnArgTyrArgAlaArgIleArg

TyrAlaSerThrThrAsnLeuArgIleTyrValThrValAlaGlyGluArgIlePheAlaGlyGlnPheAsn

LysThrMetAspThrGlyAspProLeuThrPheGlnSerPheSerTyrAlaThrIleAsnThrAlaPheThr

PheProMetSerGlnSerSerPheThrValGlyAlaAspThrPheSerSerGlyAsnGluValTyrIleAsp

ArgPheGluLeuIleProValThrAlaThrPheGluAlaGluTyrAspLeuGluArgAlaGlnLysAlaVal

AsnAlaLeuPheThrSerIleAsnGlnIleGlyIleLysThrAspValThrAspTyrHisIleAspGlnVal

SerAsnLeuValAspCysLeuSerAspGluPheCysLeuAspGluLysArgGluLeuSerGluLysValLys

HisAlaLysArgLeuSerAspGluArgAsnLeuLeuGlnAspProAsnPheLysGlyIleAsnArgGlnLeu

-continued

AspArgGlyTrpArgGlySerThrAspIleThrIleGlnArgGlyAspAspValPheLysGluAsnTyrVal

ThrLeuProGlyThrPheAspGluCysTyrProThrTyrLeuTyrGlnLysIleAspGluSerLysLeuLys

AlaPheThrArgTyrGlnLeuArgGlyTyrIleGluAspSerGlnAspLeuGluIleTyrLeuIleArgTyr

AsnAlaLysHisGluThrValAsnValProGlyThrGlySerLeuTrpProLeuSerAlaGlnSerProIle

GlyLysCysGlyGluProAsnArgCysAlaProHisLeuGluTrpAsnProAspLeuAspCysSerCysArg

AspGlyGluLysCysAlaHisHisSerHisHisPheSerLeuAspIleAspValGlyCysThrAspLeuAsn

GluAspLeuGlyValTrpValIlePheLysIleLysThrGlnAspGlyHisAlaArgLeuGlyAsnLeuGlu

PheLeuGluGluLysProLeuValGlyGluAlaLeuAlaArgValLysArgAlaGluLysLysTrpArgAsp

LysArgGluLysLeuGluTrpGluThrAsnIleValTyrLysGluAlaLysGluSerValAspAlaLeuPhe

ValAsnSerGlnTyrAspGlnLeuGlnAlaAspThrAsnIleAlaMetIleHisAlaAlaAspLysArgVal

HisSerIleArgGluAlaTyrLeuProGluLeuSerValIleProGlyValAsnAlaAlaIlePheGluGlu

LeuGluGlyArgIlePheThrAlaPheSerLeuTyrAspAlaArgAsnValIleLysAsnGlyAspPheAsn

AsnGlyLeuSerCysTrpAsnValLysGlyHisValAspValGluGluGlnAsnAsnGlnArgSerValLeu

ValValProGluTrpGluAlaGluValSerGlnGluValArgValCysProGlyArgGlyTyrIleLeuArg

ValThrAlaTyrLysGluGlyTyrGlyGluGlyCysValThrIleHisGluIleGluAsnAsnThrAspGlu

LeuLysPheSerAsnCysValGluGluGluIleTyrProAsnAsnThrValThrCysAsnAspTyrThrVal

AsnGlnGluGluTyrGlyGlyAlaTyrThrSerArgAsnArgGlyTyrAsnGluAlaProSerValProAla

AspTyrAlaSerValTyrGluGluLysSerTyrThrAspGlyArgArgGluAsnProCysGluPheAsnArg

GlyTyrArgAspTyrThrProLeuProValGlyTyrValThrLysGluLeuGluTyrPheProGluThrAsp

LysValTrpIleGluIleGlyGluThrGluGlyThrPheIleValAspSerValGluLeuLeuLeuMetGlu

Glu

6.6.6 Amino Acid Sequence of the EG11091 Crystal Protein (SEQ ID NO:30)

MetAspAsnAsnProAsnIleAsnGluCysIleProTyrAsnCysLeuSerAsnProGluValGluValLeu

GlyGlyGluArgIleGluThrGlyTyrThrProIleAspIleSerLeuSerLeuThrGlnPheLeuLeuSer

GluPheValProGlyAlaGlyPheValLeuGlyLeuValAspIleIleTrpGlyIlePheGlyProSerGln

TrpAspAlaPheLeuValGlnIleGluGlnLeuIleAsnGlnArgIleGluGluPheAlaArgAsnGlnAla

IleSerArgLeuGluGlyLeuSerAsnLeuTyrGlnIleTyrAlaGluSerPheArgGluTrpGluAlaAsp

ProThrAsnProAlaLeuArgGluGluMetArgIleGlnPheAsnAspMetAsnSerAlaLeuThrThrAla

IleProLeuPheAlaValGlnAsnTyrGlnValProLeuLeuSerValTyrValGlnAlaAlaAsnLeuHis

LeuSerValLeuArgAspValSerValPheGlyGlnArgTrpGlyPheAspAlaAlaThrIleAsnSerArg

TyrAsnAspLeuThrArgLeuIleGlyAsnTyrThrAspTyrAlaValArgTrpTyrAsnThrGlyLeuGlu

ArgValTrpGlyProAspSerArgAspTrpValArgTyrAsnGlnPheArgArgGluLeuThrLeuThrVal

LeuAspIleValAlaLeuPheProAsnTyrAspSerArgArgTyrProIleArgThrValSerGlnLeuThr

ArgGluIleTyrThrAsnProValLeuGluAsnPheAspGlySerPheArgGlySerAlaGlnGlyIleGlu

ArgSerIleArgSerProHisLeuMetAspIleLeuAsnSerIleThrIleTyrThrAspAlaHisArgGly

TyrTyrTyrTrpSerGlyHisGlnIleMetAlaSerProValGlyPheSerGlyProGluPheThrPhePro

LeuTyrGlyThrMetGlyAsnAlaAlaProGlnGlnArgIleValAlaGlnLeuGlyGlnGlyValTyrArg

ThrLeuSerSerThrLeuTyrArgArgProPheAsnIleGlyIleAsnAsnGlnGlnLeuSerValLeuAsp

-continued

GlyThrGluPheAlaTyrGlyThrSerSerAsnLeuProSerAlaValTyrArgLysSerGlyThrValAsp

SerLeuAspGluIleProProGlnAsnAsnAsnValProProArgGlnGlyPheSerHisArgLeuSerHis

ValSerMetPheArgSerGlyPheSerAsnSerSerValSerIleIleArgAlaProMetPheSerTrpIle

HisArgSerAlaThrLeuThrAsnThrIleAspProGluArgIleAsnGlnIleProLeuValLysGlyPhe

ArgValTrpGlyGlyThrSerValIleThrGlyProGlyPheThrGlyGlyAspIleLeuArgArgAsnThr

PheGlyAspPheValSerLeuGlnValAsnIleAsnSerProIleThrGlnArgTyrArgLeuArgPheArg

TyrAlaSerSerArgAspAlaArgValIleValLeuThrGlyAlaAlaSerThrGlyValGlyGlyGlnVal

SerValAsnMetProLeuGlnLysThrMetGluIleGlyGluAsnLeuThrSerArgThrPheArgTyrThr

AspPheSerAsnProPheSerPheArgAlaAsnProAspIleIleGlyIleSerGluGlnProLeuPheGly

AlaGlySerIleSerSerGlyGluLeuTyrIleAspLysIleGluIleIleLeuAlaAspAlaThrPheGlu

AlaGluSerAspLeuGluArgAlaGlnLysAlaValAsnAlaLeuPheThrSerSerAsnGlnIleGlyLeu

LysThrAspValThrAspTyrHisIleAspGlnValSerAsnLeuValAspCysLeuSerAspGluPheCys

LeuAspGluLysArgGluLeuSerGluLysValLysHisAlaLysArgLeuSerAspGluArgAsnLeuLeu

GlnAspProAsnPheArgGlyIleAsnArgGlnProAspArgGlyTrpArgGlySerThrAspIleThrIle

GlnGlyGlyAspAspValPheLysGluAsnTyrValThrLeuProGlyThrValAspGluCysTyrProThr

TyrLeuTyrGlnLysIleAspGluSerLysLeuLysAlaTyrThrArgTyrGluLeuArgGlyTyrIleGlu

AspSerGlnAspLeuGluIleTyrLeuIleArgTyrAsnAlaLysHisGluIleValAsnValProGlyThr

GlySerLeuTrpProLeuSerAlaGlnSerProIleGlyLysCysGlyGluProAsnArgCysAlaProHis

LeuGluTrpAsnProAspLeuAspCysSerCysArgAspGlyGluLysCysAlaHisHisSerHisHisPhe

ThrLeuAspIleAspValGlyCysThrAspLeuAsnGluAspLeuGlyValTrpValIlePheLysIleLys

ThrGlnAspGlyHisAlaArgLeuGlyAsnLeuGluPheLeuGluGluLysProLeuLeuGlyGluAlaLeu

AlaArgValLysArgAlaGluLysLysTrpArgAspLysArgGluLysLeuGlnLeuGluThrAsnIleVal

TyrLysGluAlaLysGluSerValAspAlaLeuPheValAsnSerGlnTyrAspArgLeuGlnValAspThr

AsnIleAlaMetIleHisAlaAlaAspLysArgValHisArgIleArgGluAlaTyrLeuProGluLeuSer

ValIleProGlyValAsnAlaAlaIlePheGluGluLeuGluGlyArgIlePheThrAlaTyrSerLeuTyr

AspAlaArgAsnValIleLysAsnGlyAspPheAsnAsnGlyLeuLeuCysTrpAsnValLysGlyHisVal

AspValGluGluGlnAsnAsnHisArgSerValLeuValIleProGluTrpGluAlaGluValSerGlnGlu o ValArgValCysProGlyArgGlyTyr-
IleLeuArgValThrAlaTyrLysGluG-
lyTyrGlyGluGlyCys

ValThrIleHisGluIleGluAspAsnThrAspGluLeuLysPheSerAsnCysValGluGluGluValTyr

ProAsnAsnThrValThrCysAsnAsnTyrThrGlyThrGlnGluGluTyrGluGlyThrTyrThrSerArg

AsnGlnGlyTyrAspGluAlaTyrGlyAsnAsnProSerValProAlaAspTyrAlaSerValTyrGluGlu

LysSerTyrThrAspGlyArgArgGluAsnProCysGluSerAsnArgGlyTyrGlyAspTyrThrProLeu

ProAlaGlyTyrValThrLysAspLeuGluTyrPheProGluThrAspLysValTrpIleGluIleGlyGlu

ThrGluGlyThrPheIleValAspSerValGluLeuLeuLeuMetGluGlu 6.6.7 Amino Acid Sequence of the EG11768 Crystal Protein (SEQ ID NO:34)

MetAspAsnAsnProAsnIleAsnGluCysIleProTyrAsnCysLeuSerAsnProGluValGluValLeu

GlyGlyGluArgIleGluThrGlytyrThrProIleAspIleSerLeuSerLeuThrGlnPheLeuLeuSer

GluPheValProGlyAlaGlyPheValLeuGlyLeuValAspIleIleTrpGlyIlePheGlyProSerGln

TrpAspAlaPheLeuValGlnIleGluGlnLeuIleAsnGlnArgIleGluGluPheAlaArgAsnGlnAla

IleSerArgLeuGluglyLeuSerAsnleuTyrGlnIleTyrAlaGluSerPheArgGluTrpGluAlaAsp

ProThrAsnProAlaLeuArgGluGluMetArgIleGlnPheAsnAspMetAsnSerAlaLeuThrThrAla

IleProLeuPheAlaValGlnAsnTyrGlnValProLeuleuSerValTyrValGlnAlaAlaAsnLeuHis

LeuSerValLeuArgAspValSerValPheGlyGlnArgTrpGlyPheAspAlaAlaThrIleAsnSerArg

TyrAsnAspLeuThrArgLeuIleGlyAsnTyrThrAspTyrAlaValArgTrpTyrAsnThrGlyLeuGlu

ArgValTrpGlyProAspSerArgAspTrpValArgTyrAsnGlnPheArgArgGluLeuThrLeuThrVal

LeuAspIleValAlaLeuPheProAsnTyrAspSerArgArgTyrProIleArgThrValSerGlnLeuThr

ArgGluIleTyrThrAsnProValLeuGluAsnPheAspGlySerPheArgGlySerAlaGlnGlyIleGlu

ArgSerIleArgSerProHisLeuMetAspIleLeuAsnSerIleThrIleTyrThrAspAlaHisArgGly

TyrTyrTyrTrpSerGlyHisGlnIleMetAlaSerProValGlyPheSerGlyProGluPheThrPhePro

LeuTyrGlyThrMetGlyAsnAlaAlaProGlnGlnArgIleValAlaGlnLeuGlyGlnGlyValTyrArg

ThrLeuSerSerThrLeuTyrArgArgproPheAsnIleGlyIleAsnAsnGlnGlnLeuSerValLeuAsp

GlyThrGluPheAlaTyrGlyThrSerSerAsnLeuProSerAlaValTyrArgLysSerGlyThrValAsp

SerLeuAspGluIleProProGlnAsnAsnAsnValProProArgGlnGlyPheSerHisArgLeuSerHis

ValSerMetPheArgSerGlyPheSerAsnSerSerValSerIleIleArgAlaProMetPheSerTrpIle

HisArgSerAlaGluPheAsnAsnIleIleAlaSerAspSerIleThrGlnIleProLeuValLysAlaHis

ThrLeuGlnSerGlyThrThrValValArgGlyProGlyPheThrGlyGlyAspIleLeuArgArgThrSer

GlyGlyProPheAlaTyrThrIleValAsnIleAsnGlyGlnLeuProGlnArgTyrArgAlaArgIleArg

TyrAlaSerThrThrAsnLeuArgIleTyrValThrValAlaGlyGluArgIlePheAlaGlyGlnPheAsn

LysThrMetAspThrGlyAspProLeuThrPheGlnSerPheSerTyrAlaThrIleAsnThrAlaPheThr

PheProMetSerGlnSerSerPheThrValGlyAlaAspThrPheSerSerGlyAsnGluValTyrIleAsp

ArgPheGluLeuIleProValThrAlaThrLeuGluAlaGluTyrAsnLeuGluArgAlaGlnLysAlaVal

AsnAlaLeuPheThrSerThrAsnGlnLeuGlyLeuLysThrAsnValThrAspTyrHisIleAspGlnVal

SerAsnLeuValThrTyrLeuSerAspGluPheCysLeuAspGluLysArgGluLeuSerGluLysValLys

HisAlaLysArgLeuSerAspGluArgAsnLeuLeuGlnAspSerAsnPheLysAspIleAsnArgGlnPro

GluArgGlyTrpGlyGlySerThrGlyIleThrIleGlnGlyGlyAspAspValPheLysGlnAsnTyrVal

ThrLeuSerGlyThrPheAspGluCysTyrProThrTyrLeuTyrGlnLysIleAspGluSerLysLeuLys

AlaPheThrArgTyrGlnLeuArgGlyTyrIleGluAspSerGlnAspLeuGluIleTyrLeuIleArgTyr

AsnAlaLysHisGluThrValAsnValProGlyThrGlySerLeuTrpProLeuSerAlaGlnSerProIle

GlyLysCysGlyGluProAsnArgCysAlaProHisLeuGluTrpAsnProAspLeuAspCysSerCysArg

AspGlyGluLysCysAlaHisHisSerHisHisPheSerLeuAspIleAspValGlyCysThrAspLeuAsn

GluAspLeuGlyValTrpValIlePheLysIleLysThrGlnAspGlyHisAlaArgLeuGlyAsnLeuGlu

PheLeuGluGluLysProLeuValGlyGluAlaLeuAlaArgValLysArgAlaGluLysLysTrpArgAsp

LysArgGluLysLeuGluTrpGluThrAsnIleValTyrLysGluAlaLysGluSerValAspAlaLeuPhe

-continued

```
ValAsnSerGlnTyrAspGlnLeuGlnAlaAspThrAsnIleAlaMetIleHisAlaAlaAspLysArgVal

HisSerIleArgGluAlaTyrLeuProGluLeuSerValIleProGlyValAsnAlaAlaIlePheGluGlu

LeuGluGlyArgIlePheThrAlaPheSerLeuTyrAspAlaArgAsnValIleLysAsnGlyAspPheAsn

AsnGlyLeuSerCysTrpAsnValLysGlyHisValAspValGluGluGlnAsnAsnGlnArgSerValLeu

ValValProGluTrpGluAlaGluValSerGlnGluValArgValCysProGlyArgGlyTyrIleLeuArg

ValThrAlaTyrLysGluGlyTyrGlyGluGlyCysValThrIleHisGluIleGluAsnAsnThrAspGlu

LeuLysPheSerAsnCysValGluGluGluIleTyrProAsnAsnThrValThrCysAsnAspTyrThrVal

AsnGlnGluGluTyrGlyGlyAlaTyrThrSerArgAsnArgGlyTyrAsnGluAlaProSerValProAla

AspTyrAlaSerValTrpGluGluLysSerTyrThrAspGlyArgArgGluAsnProCysGluPheAsnArg

GlyTyrArgAspTyrThrProLeuProValGlyTyrValThrLysGluLeuGluTyrPheProGluThrAsp

LysValTrpIleGluIleGlyGluThrGluGlyThrPheIleValAspSerValGluLeuLeuLeuMetGlu

Glu
```

6.7 Example 7

DNA Sequences Encoding the Novel Crystal Proteins

6.7.1 DNA Sequence Encoding the EG11063 Crystal Protein (SEQ ID NO:9)

```
ATG GAT AAC AAT CCG AAC ATC AAT GAA TGC ATT CCT TAT AAT TGT TTA     48

AGT AAC CCT GAA GTA GAA GTA TTA GGT GGA GAA AGA ATA GAA ACT GGT     96

TAC ACC CCA ATC GAT ATT TCC TTG TCG CTA ACG CAA TTT CTT TTG AGT    144

GAA TTT GTT CCC GGT GCT GGA TTT GTG TTA GGA CTA GTT GAT ATA ATA    192

TGG GGA ATT TTT GGT CCC TCT CAA TGG GAC GCA TTT CTT GTA CAA ATT    240

GAA CAG TTA ATT AAC CAA AGA ATA GAA GAA TTC GCT AGG AAC CAA GCC    268

ATT TCT AGA TTA GAA GGA CTA AGC AAT CTT TAT CAA ATT TAC GCA GAA    336

TCT TTT AGA GAG TGG GAA GCA GAT CCT ACT AAT CCA GCA TTA AGA GAA    384

GAG ATG CGT ATT CAA TTC AAT GAC ATG AAC AGT GCC CTT ACA ACC GCT    432

ATT CCT CTT TTT GCA GTT CAA AAT TAT CAA GTT CCT CTT TTA TCA GTA    460

TAT GTT CAA GCT GCA AAT TTA CAT TTA TCA GTT TTG AGA GAT GTT TCA    528

GTG TTT GGA CAA AGG TGG GGA TTT GAT GCC GCG ACT ATC AAT AGT CGT    576

TAT AAT GAT TTA ACT AGG CTT ATT GGC AAC TAT ACA GAT TAT GCT GTA    624

CGC TGG TAC AAT ACG GGA TTA GAA CGT GTA TGG GGA CCG GAT TCT AGA    672

GAT TGG GTA AGG TAT AAT CAA TTT AGA AGA GAA TTA ACA CTA ACT GTA    720

TTA GAT ATC GTT GCT CTG TTC CCG AAT TAT GAT AGT AGA AGA TAT CCA    768

ATT CGA ACA GTT TCC CAA TTA ACA AGA GAA ATT TAT ACA AAC CCA GTA    816

TTA GAA AAT TTT GAT GGT AGT TTT CGA GGC TCG GCT CAG GGC ATA GAA    864

AGA AGT ATT AGG AGT CCA CAT TTG ATG GAT ATA CTT AAC AGT ATA ACC    912

ATC TAT ACG GAT GCT CAT AGG GGT TAT TAT TAT TGG TCA GGG CAT CAA    960

ATA ATG GCT TCT CCT GTA GGG TTT TCG GGG CCA GAA TTC ACT TTT CCG   1008

CTA TAT GGA ACT ATG GGA AAT GCA GCT CCA CAA CAA CGT ATT GTT GCT   1056
```

-continued

```
CAA CTA GGT CAG GGC GTG TAT AGA ACA TTA TCG TCC ACT TTA TAT AGA  1104

AGA CCT TTT AAT ATA GGG ATA AAT AAT CAA CAA CTA TCT GTT CTT GAC  1152

GGG ACA GAA TTT GCT TAT GGA ACC TCC TCA AAT TTG CCA TCC GCT GTA  1200

TAC AGA AAA AGC GGA ACG GTA GAT TCG CTG GAT GAA ATA CCG CCA CAG  1248

AAT AAC AAC GTG CCA CCT AGG CAA GGA TTT AGT CAT CGA TTA AGC CAT  1296

GTT TCA ATG TTT CGT TCA GGC TTT AGT AAT AGT AGT GTA AGT ATA ATA  1344

AGA GCT CCA ATG TTT TCT TGG ACG CAC CGT AGT GCA ACC CCT ACA AAT  1392

ACA ATT GAT CCG GAG AGG ATT ACT CAA ATA CCA TTG GTA AAA GCA CAT  1440

ACA CTT CAG TCA GGT ACT ACT GTT GTA AGA GGG CCC GGG TTT ACG GGA  1488

GGA GAT ATT CTT CGA CGA ACA AGT GGA GGA CCA TTT GCT TAT ACT ATT  1536

GTT AAT ATA AAT GGG CAA TTA CCC CAA AGG TAT CGT GCA AGA ATA CGC  1584

TAT GCC TCT ACT ACA AAT CTA AGA ATT TAC GTA ACG GTT GCA GGT GAA  1632

CGG ATT TTT GCT GGT CAA TTT AAC AAA ACA ATG GAT ACC GGT GAC CCA  1680

TTA ACA TTC CAA TCT TTT AGT TAC GCA ACT ATT AAT ACA GCT TTT ACA  1728

TTC CCA ATG AGC CAG AGT AGT TTC ACA GTA GGT GCT GAT ACT TTT AGT  1776

TCA GGG AAT GAA GTT TAT ATA GAC AGA TTT GAA TTG ATT CCA GTT ACT  1824

GCA ACA TTT GAA GCA GAA TAT GAT TTA GAA AGA GCA CAA AAG GCG GTG  1872

AAT GCG CTG TTT ACT TCT ATA AAC CAA ATA GGG ATA AAA ACA GAT GTG  1920

ACG GAT TAT CAT ATT GAT CAA GTA TCC AAT TTA GTG GAT TGT TTA TCA  1968

GAT GAA TTT TGT CTG GAT GAA AAG CGA GAA TTG TCC GAG AAA GTC AAA  2016

CAT GCG AAG CGA CTC AGT GAT GAG CGG AAT TTA CTT CAA GAT CCA AAC  2064

TTC AAA GGC ATC AAT AGG CAA CTA GAC CGT GGT TGG AGA GGA AGT ACG  2112

GAT ATT ACC ATC CAA AGA GGA GAT GAC GTA TTC AAA GAA AAT TAT GTC  2160

ACA CTA CCA GGT ACC TTT GAT GAG TGC TAT CCA ACA TAT TTG TAT CAA  2208

AAA ATC GAT GAA TCA AAA TTA AAA GCC TTT ACC CGT TAT CAA TTA AGA  2256

GGG TAT ATC GAA GAT AGT CAA GAC TTA GAA ATC TAT TTA ATT CGC TAC  2304

AAT GCA AAA CAT GAA ACA GTA AAT GTG CCA GGT ACG GGT TCC TTA TGG  2352

CCG CTT TCA GCC CAA AGT CCA ATC GGA AAG TGT GGA GAG CCG AAT CGA  2400

TGC GCG CCA CAC CTT GAA TGG AAT CCT GAC TTA GAT TGT TCG TGT AGG  2448

GAT GGA GAA AAG TGT GCC CAT CAT TCG CAT CAT TTC TCC TTA GAC ATT  2496

GAT GTA GGA TGT ACA GAC TTA AAT GAG GAC CTA GGT GTA TGG GTG ATC  2544

TTT AAG ATT AAG ACG CAA GAT GGG CAC GCA AGA CTA GGG AAT CTA GAG  2592

TTT CTC GAA GAG AAA CCA TTA GTA GGA GAA GCG CTA GCT CGT GTG AAA  2640

AGA GCG GAG AAA AAA TGG AGA GAC AAA CGT GAA AAA TTG GAA TGG GAA  2688

ACA AAT ATC GTT TAT AAA GAG GCA AAA GAA TCT GTA GAT GCT TTA TTT  2736

GTA AAC TCT CAA TAT GAT CAA TTA CAA GCG GAT ACG AAT ATT GCC ATG  2784

ATT CAT GCG GCA GAT AAA CGT GTT CAT AGC ATT CGA GAA GCT TAT CTG  2832

CCT GAG CTG TCT GTG ATT CCG GGT GTC AAT GCG GCT ATT TTT GAA GAA  2880

TTA GAA GGG CGT ATT TTC ACT GCA TTC TCC CTA TAT GAT GCG AGA AAT  2928

GTC ATT AAA AAT GGT GAT TTT AAT AAT GGC TTA TCC TGC TGG AAC GTG  2976
```

-continued

```
AAA GGG CAT GTA GAT GTA GAA GAA CAA AAC AAC CAA CGT TCG GTC CTT  3024
GTT GTT CCG GAA TGG GAA GCA GAA GTG TCA CAA GAA GTT CGT GTC TGT  3072
CCG GGT CGT GGC TAT ATC CTT CGT GTC ACA GCG TAC AAG GAG GGA TAT  3120
GGA GAA GGT TGC GTA ACC ATT CAT GAG ATC GAG AAC AAT ACA GAC GAA  3168
CTG AAG TTT AGC AAC TGC GTA GAA GAG GAA ATC TAT CCA AAT AAC ACG  3216
GTA ACG TGT AAT GAT TAT ACT GTA AAT CAA GAA GAA TAC GGA GGT GCG  3264
TAC ACT TCT CGT AAT CGA GGA TAT AAC GAA GCT CCT TCC GTA CCA GCT  3312
GAT TAT GCG TCA GTC TAT GAA GAA AAA TCG TAT ACA GAT GGA CGA AGA  3360
GAG AAT CCT TGT GAA TTT AAC AGA GGG TAT AGG GAT TAC ACG CCA CTA  3408
CCA GTT GGT TAT GTG ACA AAA GAA TTA GAA TAC TTC CCA GAA ACC GAT  3456
AAG GTA TGG ATT GAG ATT GGA GAA ACG GAA GGA ACA TTT ATC GTG GAC  3504
AGC GTG GAA TTA CTC CTT ATG GAG GAA                              3531
```

6.7.2 DNA Sequence Encoding the EG11074 Crystal Protein (SEQ ID NO:11)

```
ATG GAT AAC AAT CCG AAC ATC AAT GAA TGC ATT CCT TAT AAT TGT TTA    48
AGT AAC CCT GAA GTA GAA GTA TTA GGT GGA GAA AGA ATA GAA ACT GGT    96
TAC ACC CCA ATC GAT ATT TCC TTG TCG CTA ACG CAA TTT CTT TTG AGT   144
GAA TTT GTT CCC GGT GCT GGA TTT GTG TTA GGA CTA GTT GAT ATA ATA   192
TGG GGA ATT TTT GGT CCC TCT CAA TGG GAC GCA TTT CTT GTA CAA ATT   240
GAA CAG TTA ATT AAC CAA AGA ATA GAA GAA TTC GCT AGG AAC CAA GCC   286
ATT TCT AGA TTA GAA GGA CTA AGC AAT CTT TAT CAA ATT TAC GCA GAA   336
TCT TTT AGA GAG TGG GAA GCA GAT CCT ACT AAT CCA GCA TTA AGA GAA   354
GAG ATG CGT ATT CAA TTC AAT GAC ATG AAC AGT GCC CTT ACA ACC GCT   432
ATT CCT CTT TTT GCA GTT CAA AAT TAT CAA GTT CCT CTT TTA TCA GTA   480
TAT GTT CAA GCT GCA AAT TTA CAT TTA TCA GTT TTG AGA GAT GTT TCA   528
GTG TTT GGA CAA AGG TGG GGA TTT GAT GCC GCG ACT ATC AAT AGT CGT   576
TAT AAT GAT TTA ACT AGG CTT ATT GGC AAC TAT ACA GAT TAT GCT GTA   624
CGC TGG TAC AAT ACG GGA TTA GAA CGT GTA TGG GGA CCG GAT TCT AGA   672
GAT TGG GTA AGG TAT AAT CAA TTT AGA AGA GAA TTA ACA CTA ACT GTA   720
TTA GAT ATC GTT GCT CTG TTC CCG AAT TAT GAT AGT AGA AGA TAT CCA   768
ATT CGA ACA GTT TCC CAA TTA ACA AGA GAA ATT TAT ACA AAC CCA GTA   616
TTA GAA AAT TTT GAT GGT AGT TTT CGA GGC TCG GCT CAG GGC ATA GAA   864
AGA AGT ATT AGG AGT CCA CAT TTG ATG GAT ATA CTT AAC AGT ATA ACC   912
ATC TAT ACG GAT GCT CAT AGG GGT TAT TAT TAT TGG TCA GGG CAT CAA   960
ATA ATG GcT TCT CCT GTA GGG TTT TCG GGG CCA GAA TTC ACT TTT CCG  1008
CTA TAT GQA ACT ATG GGA AAT GCA GCT CCA CAA CAA CGT ATT GTT GCT  1056
CAA CTA GGT CAG GGC GTG TAT AGA ACA TTA TCG TCC ACT TTA TAT AGA  1104
AGA CCT TTT AAT ATA GGG ATA AAT AAT CAA CAA CTA TCT GTT CTT GAC  1152
GGG ACA GAA TTT GCT TAT GGA ACC TCC TCA AAT TTG CCA TCC GCT GTA  1200
```

-continued

```
TAC AGA AAA AGC GGA ACG GTA GAT TCG CTG GAT GAA ATA CCG CCA CAG  1246
AAT AAC AAC GTG CCA CCT AGG CAA GGA TTT AGT CAT CGA TTA AGC CAT  1296
GTT TCA ATG TTT CGT TCA GGC TTT AGT AAT AGT AGT GTA AGT ATA ATA  1344
AGA GCT CCA ATG TTT TCT TGG ACG CAC CGT AGT GCA ACC CCT ACA AAT  1392
ACA ATT GAT CCG GAG AGG ATT ACT CAA ATA CCA TTG GTA AAA GCA CAT  1440
ACA CTT CAG TCA GGT ACT ACT GTT GTA AGA GGG CCC GGG TTT ACG GGA  1488
GGA GAT ATT CTT CGA CGA ACA AGT GGA GGA CCA TTT GCT TAT ACT ATT  1536
GTT AAT ATA AAT GGG CAA TTA CCC CAA AGG TAT CGT GCA AGA ATA CGC  1584
TAT GCC TCT ACT ACA AAT CTA AGA ATT TAC GTA ACG GTT GCA GGT GAA  1632
CGG ATT TTT GCT GGT CAA TTT AAC AAA ACA ATG GAT ACC GGT GAC CCA  1680
TTA ACA TTC CAA TCT TTT AGT TAC GCA ACT ATT AAT ACA GCT TTT ACA  1728
TTC CCA ATG AGC CAG AGT AGT TTC ACA GTA GGT GCT GAT ACT TTT AGT  1776
TCA GGG AAT GAA GTT TAT ATA GAC AGA TTT GAA TTG ATT CCA GTT ACT  1824
GCA ACA CTC GAG GCT GAA TAT AAT CTG GAA AGA GCG CAG AAG GCG GTG  1872
AAT GCG CTG TTT ACG TCT ACA AAC CAA CTA GGG CTA AAA ACA AAT GTA  1920
ACG GAT TAT CAT ATT GAT CAA GTG TCC AAT TTA GTT ACG TAT TTA TCG  1969
GAT GAA TTT TGT CTG GAT GAA AAG CGA GAA TTG TCC GAG AAA GTC AAA  2016
CAT GCG AAG CGA CTC AGT GAT GAA CGC AAT TTA CTC CAA GAT TCA AAT  2064
TTC AAA GAC ATT AAT AGG CAA CCA GAA CGT GGG TGG GGC GGA AGT ACA  2112
GGG ATT ACC ATC CAA GGA GGG GAT GAC GTA TTT AAA GAA AAT TAC GTC  2160
ACA CTA TCA GGT ACC TTT GAT GAG TGC TAT CCA ACA TAT TTG TAT CAA  2205
AAA ATC GAT GAA TCA AAA TTA AAA GCC TTT ACC CGT TAT CAA TTA AGA  2256
GGG TAT ATC GAA GAT AGT CAA GAC TTA GAA ATC TAT TTA ATT CGC TAC  2304
AAT GCA AAA CAT GAA ACA GTA AAT GTG CCA GGT ACG GGT TCC TTA TGG  2352
CCG CTT TCA GCC CAA AGT CCA ATC GGA AAG TGT GGA GAG CCG AAT CGA  2400
TGC GCG CCA CAC CTT GAA TGG AAT CCT GAC TTA GAT TGT TCG TGT AGG  2448
GAT GGA GAA AAG TGT GCC CAT CAT TCG CAT CAT TTC TCC TTA GAC ATT  2496
GAT GTA GGA TGT ACA GAC TTA AAT GAG GAC CTA GGT GTA TGG GTG ATC  2544
TTT AAG ATT AAG ACG CAA GAT GGG CAC GCA AGA CTA GGG AAT CTA GAG  2592
TTT CTC GAA GAG AAA CCA TTA GTA GGA GAA GCG CTA GCT CGT GTG AAA  2640
AGA GCG GAG AAA AAA TGG AGA GAC AAA CGT GAA AAA TTG GAA TGG GAA  2688
ACA AAT ATC GTT TAT AAA GAG GCA AAA GAA TCT GTA GAT GCT TTA TTT  2736
GTA AAC TCT CAA TAT GAT CAA TTA CAA GCG GAT ACG AAT ATT GCC ATG  2784
ATT CAT GCG GCA GAT AAA CGT GTT CAT AGC ATT CGA GAA GCT TAT CTG  2832
CCT GAG CTG TCT GTG ATT CCG GGT GTC AAT GCG GCT ATT TTT GAA GAA  2880
TTA GAA GGG CGT ATT TTC ACT GCA TTC TCC CTA TAT GAT GCG AGA AAT  2928
GTC ATT AAA AAT GGT GAT TTT AAT AAT GGC TTA TCC TGC TGG AAC GTG  2976
AAA GGG CAT GTA GAT GTA GAA GAA CAA AAC AAC CAA CGT TCG GTC CTT  3024
GTT GTT CCG GAA TGG GAA GCA GAA GTG TCA CAA GAA GTT CGT GTC TGT  3072
CCG GGT CGT GGC TAT ATC CTT CGT GTC ACA GCG TAC AAG GAG GGA TAT  3120
```

-continued

```
GGA GAA GGT TGC GTA ACC ATT CAT GAG ATC GAG AAC AAT ACA GAC GAA  3168
CTG AAG TTT AGC AAC TGC GTA GAA GAG GAA ATC TAT CCA AAT AAC ACG  3216
GTA ACG TGT AAT GAT TAT ACT GTA AAT CAA GAA GAA TAC GGA GGT GCG  3264
TAC ACT TCT CGT AAT CGA GGA TAT AAC GAA GCT CCT TCC GTA CCA GCT  3312
GAT TAT GCG TCA GTC TAT GAA GAA AAA TCG TAT ACA GAT GGA CGA AGA  3360
GAG AAT CCT TGT GAA TTT AAC AGA GGG TAT AGG GAT TAC ACG CCA CTA  3408
CCA GTT GGT TAT GTG ACA AAA GAA TTA GAA TAC TTC CCA GAA ACC GAT  3456
AAG GTA TGG ATT GAG ATT GGA GAA ACG GAA GGA ACA TTT ATC GTG GAC  3504
AGC GTG GAA TTA CTC CTT ATG GAG GAA                              3531
```

6.73 DNA Sequence Encoding the EG11735 Crystal Protein (SEQ ID NO:13)

```
ATG GAT AAC AAT CCG AAC ATC AAT GAA TGC ATT CCT TAT AAT TGT TTA    48
AGT AAC CCT GAA GTA GAA GTA TTA GGT GGA GAA AGAATA GAA ACT GGT     96
TAC ACC CCA ATC GAT ATT TCC TTG TCG CTA ACG CAA TTT CTT TTG AGT   144
GAA TTT GTT CCC GGT GCT GGA TTT GTG TTA GGA CTA GTT GAT ATA ATA   192
TGG GGA ATT TTT GGT CCC TCT CAA TGG GAC GCA TTT CTT GTA CAA ATT   240
GAA CAG TTA ATT AAC CAA AGA ATA GAA GAA TTC GCT AGG AAC CAA GCC   288
ATT TCT AGA TTA GAA GGA CTA AGC AAT CTT TAT CAA ATT TAC GCA GAA   336
TCT TTT AGA GAG TGG GAA GCA GAT CCT ACT AAT CCA GCA TTA AGA GAA   384
GAG ATG CGT ATT CAA TTC AAT GAC ATG AAC AGT GCC CTT ACA ACC GCT   432
ATT CCT CTT TTT GCA GTT CAA AAT TAT CAA GTT CCT CTT TTA TCA GTA   480
TAT GTT CAAGCT GCA AAT TTA CAT TTA TCA GTT TTG AGA GAT GTT TCA    528
GTG TTT GGA CAA AGG TGG GGA TTT GAT GCC GCG ACT ATC AAT AGT CGT   576
TAT AAT GAT TTA ACT AGG CTT ATT GGC AAC TAT ACA GAT CAT GCT GTA   624
CGC TGG TAC AAT ACG GGA TTA GAG CGT GTA TGG GGA CCG GAT TCT AGA   672
GAT TGG ATA AGA TAT AAT CAA TTT AGA AGA GAA TTA ACA CTA ACT GTA   720
TTA GAT ATC GTT TCT CTA TTT CCG AAC TAT GAT AGT AGA ACG TAT CCA   768
ATT CGA ACA GTT TCC CAA TTA ACA AGA GAA ATT TAT ACA AAC CCA GTA   816
TTA GAA AAT TTT GAT GGT AGT TTT CGA GGC TCG GCT CAG GGC ATA GAA   864
GGA AGT ATT AGG AGT CCA CAT TTG ATG GAT ATA CTT AAC AGT ATA ACC   912
ATC TAT ACG GAT GCT CAT AGA GGA GAA TAT TAT TGG TCA GGG CAT CAA   960
ATA ATG GCT TCT CCT GTA GGG TTT TCG GGG CCA GAA TTC ACT TTT CCG  1008
CTA TAT GGA ACT ATG GGA AAT GCA GCT CCA CAA CAA CGT ATT GTT GCT  1056
CAA CTA GGT CAG GGC GTG TAT AGA ACA TTA TCG TCC ACT TTA TAT AGA  1104
AGA CCT TTT AAT ATA GGG ATA AAT AAT CAA CAA CTA TCT GTT CTT GAC  1152
GGG ACA GAA TTT GCT TAT GGA ACC TCC TCA AAT TTG CCA TCC GCT GTA  1200
TAC AGA AAA AGC GGA ACG GTA GAT TCG CTG GAT GAA ATA CCG CCA CAG  1248
AAT AAC AAC GTG CCA CCT AGG CAA GGA TTT AGT CAT CGA TTA AGC CAT  1296
```

-continued

```
GTT TCA ATG TTT CGT TCA GGC TTT AGT AAT AGT AGT GTA AGT ATA ATA  1344
AGA GCT CCA ATG TTT TCT TGG ACG CAC CGT AGT GCA ACC CCT ACA AAT  1392
ACA ATT GAT CCG GAG AGG ATT ACT CAA ATA CCA TTG GTA AAA GCA CAT  1440
ACA CTT CAG TCA GGT ACT ACT GTT GTA AGA GGG CCC GGG TTT ACG GGA  1488
GGA GAT ATT CTT CGA CGA ACA AGT GGA GGA CCA TTT GCT TAT ACT ATT  1536
GTT AAT ATA AAT GGG CAA TTA CCC CAA AGG TAT CGT GCA AGA ATA CGC  1584
TAT GCC TCT ACT ACA AAT CTA AGA ATT TAC GTA ACG GTT GCA GGT GAA  1632
CGG ATT TTT GCT GGT CAA TTT AAC AAA ACA ATG GAT ACC GGT GAC CCA  1680
TTA ACA TTC CAA TCT TTT AGT TAC GCA ACT ATT AAT ACA GCT TTT ACA  1728
TTC CCA ATG AGC CAG AGT AGT TTC ACA GTA GGT GCT GAT ACT TTT AGT  1776
TCA GGG AAT GAA GTT TAT ATA GAC AGA TTT GAA TTG ATT CCA GTT ACT  1824
GCA ACA TTT GAA GCA GAA TAT GAT TTA GAA AGA GCA CAA AAG GCG GTG  1872
AAT GCG CTG TTT ACT TCT ATA AAC CAA ATA GGG ATA AAA ACA GAT GTG  1920
ACG GAT TAT CAT ATT GAT CAA GTA TCC AAT TTA GTG GAT TGT TTA TCA  1968
GAT GAA TTT TGT CTG GAT GAA AAG CGA GAA TTG TCC GAG AAA GTC AAA  2016
CAT GCG AAG CGA CTC AGT GAT GAG CGG AAT TTA CTT CAA GAT CCA AAC  2064
TTC AAA GGC ATC AAT AGG CAA CTA GAC CGT GGT TGG AGA GGA AGT ACG  2112
GAT ATT ACC ATC CAA AGA GGA GAT GAC GTA TTC AAA GAA AAT TAT GTC  2160
ACA CTA CCA GGT ACC TTT GAT GAG TGC TAT CCA ACA TAT TTG TAT CAA  2208
AAA ATC GAT GAA TCA AAA TTA AAA GCC TTT ACC CGT TAT CAA TTA AGA  2256
GGG TAT ATC GAA GAT AGT CAA GAC TTA GAA ATC TAT TTA ATT CGC TAC  2304
AAT GCA AAA CAT GAA ACA GTA AAT GTG CCA GGT ACG GGT TCC TTA TGG  2352
CCG CTT TCA GCC CAA AGT CCA ATC GGA AAG TGT GGA GAG CCG AAT CGA  2400
TGC GCG CCA CAC CTT GAA TGG AAT CCT GAC TTA GAT TGT TCG TGT AGG  2448
GAT GGA GAA AAG TGT GCC CAT CAT TCG CAT CAT TTC TCC TTA GAC ATT  2496
GAT GTA GGA TGT ACA GAC TTA AAT GAG GAC CTA GGT GTA TGG GTG ATC  2544
TTT AAG ATT AAG ACG CAA GAT GGG CAC GCA AGA CTA GGG AAT CTA GAG  2592
TTT CTC GAA GAG AAA CCA TTA GTA GGA GAA GCG CTA GCT CGT GTG AAA  2640
AGA GCG GAG AAA AAA TGG AGA GAC AAA CGT GAA AAA TTG GAA TGG GAA  2688
ACA AAT ATC GTT TAT AAA GAG GCA AAA GAA TCT GTA GAT GCT TTA TTT  2736
GTA AAC TCT CAA TAT GAT CAA TTA CAA GCG GAT ACG AAT ATT GCC ATG  2784
ATT CAT GCG GCA GAT AAA CGT GTT CAT AGC ATT CGA GAA GCT TAT CTG  2832
CCT GAG CTG TCT GTG ATT CCG GGT GTC AAT GCG GCT ATT TTT GAA GAA  2880
TTA GAA GGG CGT ATT TTC ACT GCA TTC TCC CTA TAT GAT GCG AGA AAT  2928
GTC ATT AAA AAT GGT GAT TTT AAT AAT GGC TTA TCC TGC TGG AAC GTG  2976
AAA GGG CAT GTA GAT GTA GAA GAA CAA AAC AAC CAA CGT TCG GTC CTT  3024
GTT GTT CCG GAA TGG GAA GCA GAA GTG TCA CAA GAA GTT CGT GTC TGT  3072
CCG GGT CGT GGC TAT ATC CTT CGT GTC ACA GCG TAC AAG GAG GGA TAT  3120
GGA GAA GGT TGC GTA ACC ATT CAT GAG ATC GAG AAC AAT ACA GAC GAA  3168
CTG AAG TTT AGC AAC TGC GTA GAA GAG GAA ATC TAT CCA AAT AAC ACG  3216
```

-continued

```
GTA ACG TGT AAT GAT TAT ACT GTA AAT CAA GAA GAA TAC GGA GGT GCG  3264

TAC ACT TCT CGT AAT CGA GGA TAT AAC GAA GCT CCT TCC GTA CCA GCT  3312

GAT TAT GCG TCA GTC TAT GAA GAA AAA TCG TAT ACA GAT GGA CGA AGA  3360

GAG AAT CCT TGT GAA TTT AAC AGA GGG TAT AGG GAT TAC ACG CCA CTA  3408

CCA GTT GGT TAT GTG ACA AAA GAA TTA GAA TAC TTC CCA GAA ACC GAT  3456

AAG GTA TGG ATT GAG ATT GGA GAA ACG GAA GGA ACA TTT ATC GTG GAC  3504

AGC GTG GAA TTA CTC CTT ATG GAG GAA                              3531
```

6.7.4 DNA Sequence Encoding the EG11092 Crystal Protein (SEQ ID NO:25)

```
ATG GAT AAC AAT CCG AAC ATC AAT GAA TGC ATT CCT TAT AAT TGT TTA    46

AGT AAC CCT GAA GTA GAA GTA TTA GGT GGA GAA AGA ATA GAA ACT GGT    96

TAC ACC CCA ATC GAT ATT TCC TTG TCG CTA ACG CAA TTT CTT TTG AGT   144

GAA TTT GTT CCC GGT GCT GGA TTT GTG TTA GGA CTA GTT GAT ATA ATA   192

TGG GGA ATT TTT GGT CCC TCT CAA TGG GAC GCA TTT CTT GTA CAA ATT   240

GAA CAG TTA ATT AAC CAA AGA ATA GAA GAA TTC GCT AGG AAC CAA GCC   288

ATT TCT AGA TTA GAA GGA CTA AGC AAT CTT TAT CAA ATT TAC GCA GAA   336

TCT TTT AGA GAG TGG GAA GCA GAT CCT ACT AAT CCA GCA TTA AGA GAA   384

GAG ATG CGT ATT CAA TTC AAT GAC ATG AAC AGT GCC CTT ACA ACC GCT   432

ATT CCT CTT TTT GCA GTT CAA AAT TAT CAA GTT CCT CTT TTA TCA GTA   480

TAT GTT CAA GCT GCA AAT TTA CAT TTA TCA GTT TTG AGA GAT GTT TCA   528

GTG TTT GGA CAA AGG TGG GGA TTT GAT GCC GCG ACT ATC AAT AGT CGT   576

TAT AAT GAT TTA ACT AGG CTT ATT GGC AAC TAT ACA GAT CAT GCT GTA   624

CGC TGG TAC AAT ACG GGA TTA GAG CGT GTA TGG GGA CCG GAT TCT AGA   672

GAT TGG ATA AGA TAT AAT CAA TTT AGA AGA GAA TTA ACA CTA ACT GTA   720

TTA GAT ATC GTT TCT CTA TTT CCG AAC TAT GAT AGT AGA ACG TAT CCA   768

ATT CGA ACA GTT TCC CAA TTA ACA AGA GAA ATT TAT ACA AAC CCA GTA   816

TTA GAA AAT TTT GAT GGT AGT TTT CGA GGC TCG GCT CAG GGC ATA GAA   864

AGA AGT ATT AGG AGT CCA CAT TTG ATG GAT ATA CTT AAC AGT ATA ACC   912

ATC TAT ACG GAT GCT CAT AGG GGT TAT TAT TAT TGG TCA GGG CAT CAA   960

ATA ATG GCT TCT CCT GTA GGG TTT TCG GGG CCA GAA TTC ACT TTT CCG  1008

CTA TAT GGA ACT ATG GGA AAT GCA GCT CCA CAA CAA CGT ATT GTT GCT  1056

CAA CTA GGT CAG GGC GTG TAT AGA ACA TTA TCG TCC ACT TTA TAT AGA  1104

AGA CCT TTT AAT ATA GGG ATA AAT AAT CAA CAA CTA TCT GTT CTT GAC  1152

GGG ACA GAA TTT GCT TAT GGA ACC TCC TCA AAT TTG CCA TCC GCT GTA  1200

TAC AGA AAA AGC GGA ACG GTA GAT TCG CTG GAT GAA ATA CCG CCA CAG  1248

AAT AAC AAC GTG CCA CCT AGG CAA GGA TTT AGT CAT CGA TTA AGC CAT  1296

GTT TCA ATG TTT CGT TCA GGC TTT AGT AAT AGT AGT GTA AGT ATA ATA  1344

AGA GCT CCA ATG TTT TCT TGG ACG CAC CGT AGT GCA ACC CCT ACA AAT  1392

ACA ATT GAT CCG GAG AGG ATT ACT CAA ATA CCA TTG GTA AAA GCA CAT  1440
```

-continued

```
ACA CTT CAG TCA GGT ACT ACT GTT GTA AGA GGG CCC GGG TTT ACG GGA  1488
GGA GAT ATT CTT CGA CGA ACA AGT GGA GGA CCA TTT GCT TAT ACT ATT  1536
GTT AAT ATA AAT GGG CAA TTA CCC CAA AGG TAT CGT GCA AGA ATA CGC  1584
TAT GCC TCT ACT ACA AAT CTA AGA ATT TAC GTA ACG GTT GCA GGT GAA  1632
CGG ATT TTT GCT GGT CAA TTT AAC AAA ACA ATG GAT ACC GGT GAC CCA  1680
TTA ACA TTC CAA TCT TTT AGT TAC GCA ACT ATT AAT ACA GCT TTT ACA  1728
TTC CCA ATG AGC CAG AGT AGT TTC ACA GTA GGT GCT GAT ACT TTT AGT  1776
TCA GGG AAT GAA GTT TAT ATA GAC AGA TTT GAA TTG ATT CCA GTT ACT  1624
GCA ACA TTT GAA GCA GAA TAT GAT TTA GAA AGA GCA CAA AAG GCG GTG  1872
AAT GCG CTG TTT ACT TCT ATA AAC CAA ATA GGG ATA AAA ACA GAT GTG  1920
ACG GAT TAT CAT ATT GAT CAA GTA TCC AAT TTA GTG GAT TGT TTA TCA  1968
GAT GAA TTT TGT CTG GAT GAA AAG CGA GAA TTG TCC GAG AAA GTC AAA  2016
CAT GCG AAG CGA CTC AGT GAT GAG CGG AAT TTA CTT CAA GAT CCA AAC  2064
TTC AAA GGC ATC AAT AGG CAA CTA GAC CGT GGT TGG AGA GGA AGT ACG  2112
GAT ATT ACC ATC CAA AGA GGA GAT GAC GTA TTC AAA GAA AAT TAT GTC  2160
ACA CTA CCA GGT ACC TTT GAT GAG TGC TAT CCA ACA TAT TTG TAT CAA  2208
AAA ATC GAT GAA TCA AAA TTA AAA GCC TTT ACC CGT TAT CAA TTA AGA  2256
GGG TAT ATC GAA GAT AGT CAA GAC TTA GAA ATC TAT TTA ATT CGC TAC  2304
AAT GCA AAA CAT GAA ACA GTA AAT GTG CCA GGT ACG GGT TCC TTA TGG  2352
CCG CTT TCA GCC CAA AGT CCA ATC GGA AAG TGT GGA GAG CCG AAT CGA  2400
TGC GCG CCA CAC CTT GAA TGG AAT CCT GAC TTA GAT TGT TCG TGT AGG  2448
GAT GGA GAA AAG TGT GCC CAT CAT TCG CAT CAT TTC TCC TTA GAC ATT  2496
GAT GTA GGA TGT ACA GAC TTA AAT GAG GAC CTA GGT GTA TGG GTG ATC  2544
TTT AAG ATT AAG ACG CAA GAT GGG CAC GCA AGA CTA GGG AAT CTA GAG  2592
TTT CTC GAA GAG AAA CCA TTA GTA GGA GAA GCG CTA GCT CGT GTG AAA  2640
AGA GCG GAG AAA AAA TGG AGA GAC AAA CGT GAA AAA TTG GAA TGG GAA  2688
ACA AAT ATC GTT TAT AAA GAG GCA AAA GAA TCT GTA GAT GCT TTA TTT  2736
GTA AAC TCT CAA TAT GAT CAA TTA CAA GCG GAT ACG AAT ATT GCC ATG  2784
ATT CAT GCG GCA GAT AAA CGT GTT CAT AGC ATT CGA GAA GCT TAT CTG  2832
CCT GAG CTG TCT GTG ATT CCG GGT GTC AAT GCG GCT ATT TTT GAA GAA  2880
TTA GAA GGG CGT ATT TTC ACT GCA TTC TCC CTA TAT GAT GCG AGA AAT  2928
GTC ATT AAA AAT GGT GAT TTT AAT AAT GGC TTA TCC TGC TGG AAC GTG  2976
AAA GGG CAT GTA GAT GTA GAA GAA CAA AAC AAC CAA CGT TCG GTC CTT  3024
GTT GTT CCG GAA TGG GAA GCA GAA GTG TCA CAA GAA GTT CGT GTC TGT  3072
CCG GGT CGT GGC TAT ATC CTT CGT GTC ACA GCG TAC AAG GAG GGA TAT  3120
GGA GAA GGT TGC GTA ACC ATT CAT GAG ATC GAG AAC AAT ACA GAC GAA  3168
CTG AAG TTT AGC AAC TGC GTA GAA GAG GAA ATC TAT CCA AAT AAC ACG  3216
GTA ACG TGT AAT GAT TAT ACT GTA AAT CAA GAA GAA TAC GGA GGT GCG  3264
TAC ACT TCT CGT AAT CGA GGA TAT AAC GAA GCT CCT TCC GTA CCA GCT  3312
GAT TAT GCG TCA GTC TAT GAA GAA AAA TCG TAT ACA GAT GGA CGA AGA  3360
```

-continued

GAG AAT CCT TGT GAA TTT AAC AGA GGG TAT AGG GAT TAC ACG CCA CTA 3408

CCA GTT GGT TAT GTG ACA AAA GAA TTA GAA TAC TTC CCA GAA ACC GAT 3456

AAG GTA TGG ATT GAG ATT GGA GAA ACG GAA GGA ACA TTT ATC GTG GAC 3504

AGC GTG GAA TTA CTC CTT ATG GAG GAA TAG 3534

6.7.5 DNA Sequence Encoding the EG11751 Crystal Protein (SEQ ID NO:27)

ATG GAT AAC AAT CCG AAC ATC AAT GAA TGC ATT CCT TAT AAT TGT TTA 48

AGT AAC CCT GAA GTA GAA GTA TTA GGT GGA GAA AGA ATA GAA ACT GGT 96

TAC ACC CCA ATC GAT ATT TCC TTG TCG CTA ACG CAA TTT CTT TTG AGT 144

GAA TTT GTT CCC GGT GCT GGA TTT GTG TTA GGA CTA GTT GAT ATA ATA 192

TGG GGA ATT TTT GGT CCC TCT CAA TGG GAC GCA TTT CTT GTA CAA ATT 240

GAA CAG TTA ATT AAC CAA AGA ATA GAA GAA TTC GCT AGG AAC CAA GCC 288

ATT TCT AGA TTA GAA GGA CTA AGC AAT CTT TAT CAA ATT TAC GCA GAA 336

TCT TTT AGA GAG TGG GAA GCA GAT CCT ACT AAT CCA GCA TTA AGA GAA 384

GAG ATG CGT ATT CAA TTC AAT GAC ATG AAC AGT GCC CTT ACA ACC GCT 432

ATT CCT CTT TTT GCA GTT CAA AAT TAT CAA GTT CCT CTT TTA TCA GTA 480

TAT GTT CAA GCT GCA AAT TTA CAT TTA TCA GTT TTG AGA GAT GTT TCA 528

GTG TTT GGA CAA AGG TGG GGA TTT GAT GCC GCG ACT ATC AAT AGT CGT 576

TAT AAT GAT TTA ACT AGG CTT ATT GGC AAC TAT ACA GAT TAT GCT GTA 624

CGC TGG TAC AAT ACG GGA TTA GAA CGT GTA TGG GGA CCG GAT TCT AGA 672

GAT TGG GTA AGG TAT AAT CAA TTT AGA AGA GAA TTA ACA CTA ACT GTA 720

TTA GAT ATC GTT GCT CTG TTC CCG AAT TAT GAT AGT AGA AGA TAT CCA 768

ATT CGA ACA GTT TCC CAA TTA ACA AGA GAA ATT TAT ACA AAC CCA GTA 816

TTA GAA AAT TTT GAT GGT AGT TTT CGA GGC TCG GCT CAG GGC ATA GAA 864

AGA AGT ATT AGG AGT CCA CAT TTG ATG GAT ATA CTT AAC AGT ATA ACC 912

ATC TAT ACG GAT GCT CAT AGG GGT TAT TAT TAT TGG TCA GGG CAT CAA 960

ATA ATG GCT TCT CCT GTA GGG TTT TCG GGG CCA GAA TTC ACT TTT CCG 1006

CTA TAT GGA ACT ATG GGA AAT GCA GCT CCA CAA CAA CGT ATT GTT GCT 1056

CAA CTA GGT CAG GGC GTG TAT AGA ACA TTA TCG TCC ACT TTA TAT AGA 1104

AGA CCT TTT AAT ATA GGG ATA AAT AAT CAA CAA CTA TCT GTT CTT GAC 1152

GGG ACA GAA TTT GCT TAT GGA ACC TCC TCA AAT TTG CCA TCC GCT GTA 1200

TAC AGA AAA AGC GGA ACG GTA GAT TCG CTG GAT GAA ATA CCG CCA CAG 1248

AAT AAC AAC GTG CCA CCT AGG CAA GGA TTT AGT CAT CGA TTA AGC CAT 1296

GTT TCA ATG TTT CGT TCA GGC TTT AGT AAT AGT AGT GTA AGT ATA ATA 1344

AGA GCT CCT ATG TTC TCT TGG ATA CAT CGT AGTGCT GAA TTT AAT AAT 1392

ACA ATT GAT CCG GAG AGG ATT ACT CAA ATA CCA TTG GTA AAA GCA CAT 1440

ACA CTT CAG TCA GGT ACT ACT GTT GTA AGA GGG CCC GGG TTT ACG GGA 1488

GGA GAT ATT CTT CGA CGA ACA AGT GGA GGA CCA TTT GCT TAT ACT ATT 1536

-continued

```
GTT AAT ATA AAT GGG CAA TTA CCC CAA AGG TAT CGT GCA AGA ATA CGC  1564
TAT GCC TCT ACT ACA AAT CTA AGA ATT TAC GTA ACG GTT GCA GGT GAA  1632
CGG ATT TTT GCT GGT CAA TTT AAC AAA ACA ATG GAT ACC GGT GAC CCA  1680
TTA ACA TTC CAA TCT TTT AGT TAC GCA ACT ATT AAT ACA GCT TTT ACA  1728
TTC CCA ATG AGC CAG AGT AGT TTC ACA GTA GGT GCT GAT ACT TTT AGT  1776
TCA GGG AAT GAA GTT TAT ATA GAC AGA TTT GAA TTG ATT CCA GTT ACT  1824
GCA ACA TTT GAA GCA GAA TAT GAT TTA GAA AGA GCA CAA AAG GCG GTG  1872
AAT GCG CTG TTT ACT TCT ATA AAC CAA ATA GGG ATA AAA ACA GAT GTG  1920
ACG GAT TAT CAT ATT GAT CAA GTA TCC AAT TTA GTG GAT TGT TTA TCA  1968
GAT GAA TTT TGT CTG GAT GAA AAG CGA GAA TTG TCC GAG AAA GTC AAA  2016
CAT GCG AAG CGA CTC AGT GAT GAG CGG AAT TTA CTT CAA GAT CCA AAC  2064
TTC AAA GGC ATC AAT AGG CAA CTA GAC CGT GGT TGG AGA GGA AGT ACG  2112
GAT ATT ACC ATC CAA AGA GGA GAT GAC GTA TTC AAA GAA AAT TAT GTC  2160
ACA CTA CCA GGT ACC TTT GAT GAG TGC TAT CCA ACA TAT TTG TAT CAA  2208
AAA ATC GAT GAA TCA AAA TTA AAA GCC TTT ACC CGT TAT CAA TTA AGA  2256
GGG TAT ATC GAA GAT AGT CAA GAC TTA GAA ATC TAT TTA ATT CGC TAC  2304
AAT GCA AAA CAT GAA ACA GTA AAT GTG CCA GGT ACG GGT TCC TTA TGG  2352
CCG CTT TCA GCC CAA AGT CCA ATC GGA AAG TGT GGA GAG CCG AAT CGA  2400
TGC GCG CCA CAC CTT GAA TGG AAT CCT GAC TTA GAT TGT TCG TGT AGG  2448
GAT GGA GAA AAG TGT GCC CAT CAT TCG CAT CAT TTC TCC TTA GAC ATT  2496
GAT GTA GGA TGT ACA GAC TTA AAT GAG GAC CTA GGT GTA TGG GTG ATC  2544
TTT AAG ATT AAG ACG CAA GAT GGG CAC GCA AGA CTA GGG AAT CTA GAG  2592
TTT CTC GAA GAG AAA CCA TTA GTA GGA GAA GCG CTA GCT CGT GTG AAA  2640
AGA GCG GAG AAA AAA TGG AGA GAC AAA CGT GAA AAA TTG GAA TGG GAA  2688
ACA AAT ATC GTT TAT AAA GAG GCA AAA GAA TCT GTA GAT GCT TTA TTT  2736
GTA AAC TCT CAA TAT GAT CAA TTA CAA GCG GAT ACG AAT ATT GCC ATG  2784
ATT CAT GCG GCA GAT AAA CGT GTT CAT AGC ATT CGA GAA GCT TAT CTG  2832
CCT GAG CTG TCT GTG ATT CCG GGT GTC AAT GCG GCT ATT TTT GAA GAA  2880
TTA GAA GGG CGT ATT TTC ACT GCA TTC TCC CTA TAT GAT GCG AGA AAT  2928
GTC ATT AAA AAT GGT GAT TTT AAT AAT GGC TTA TCC TGC TGG AAC GTG  2976
AAA GGG CAT GTA GAT GTA GAA GAA CAA AAC AAC CAA CGT TCG GTC CTT  3024
GTT GTT CCG GAA TGG GAA GCA GAA GTG TCA CAA GAA GTT CGT GTC TGT  3072
CCG GGT CGT GGC TAT ATC CTT CGT GTC ACA GCG TAC AAG GAG GGA TAT  3120
GGA GAA GGT TGC GTA ACC ATT CAT GAG ATC GAG AAC AAT ACA GAC GAA  3168
CTG AAG TTT AGC AAC TGC GTA GAA GAG GAA ATC TAT CCA AAT AAC ACG  3216
GTA ACG TGT AAT GAT TAT ACT GTA AAT CAA GAA GAA TAC GGA GGT GCG  3264
TAC ACT TCT CGT AAT CGA GGA TAT AAC GAA GCT CCT TCC GTA CCA GCT  3312
GAT TAT GCG TCA GTC TAT GAA GAA AAA TCG TAT ACA GAT GGA CGA AGA  3360
GAG AAT CCT TGT GAA TTT AAC AGA GGG TAT AGG GAT TAC ACG CCA CTA  3408
CCA GTT GGT TAT GTG ACA AAA GAA TTA GAA TAC TTC CCA GAA ACC GAT  3456
```

-continued

```
AAG GTA TGG ATT GAG ATT GGA GAA ACG GAA GGA ACA TTT ATC GTG GAC  3504

AGC GTG GAA TTA CTC CTT ATG GAG GAA TAG                          3534
```

6.7.6 DNA Sequence Encoding the EG11091 Crystal Protein (SEQ ID NO:29)

```
ATG GAT AAC AAT CCG AAC ATC AAT GAA TGC ATT CCT TAT AAT TGT TTA    48

AGT AAC CCT GAA GTA GAA GTA TTA GGT GGA GAA AGA ATA GAA ACT GGT    96

TAC ACC CCA ATC GAT ATT TCC TTG TCG CTA ACG CAA TTT CTT TTG AGT   144

GAA TTT GTT CCC GGT GCT GGA TTT GTG TTA GGA CTA GTT GAT ATA ATA   192

TGG GGA ATT TTT GGT CCC TCT CAA TGG GAC GCA TTT CTT GTA CAA ATT   240

GAA CAG TTA ATT AAC CAA AGA ATA GAA GAA TTC GCT AGG AAC CAA GCC   288

ATT TCT AGA TTA GAA GGA CTA AGC AATCTT TAT CAA ATT TAC GCA GAA    336

TCT TTT AGA GAG TGG GAA GCA GAT CCT ACT AAT CCA GCA TTA AGA GAA   384

GAG ATG CGT ATT CAA TTC AAT GAC ATG AAC AGT GCC CTT ACA ACC GCT   432

ATT CCT CTT TTT GCA GTT CAA AAT TAT CAA GTT CCT CTT TTA TCA GTA   480

TAT GTT CAA GCT GCA AAT TTA CAT TTA TCA GTT TTG AGA GAT GTT TCA   528

GTG TTT GGA CAA AGG TGG GGA TTT GAT GCC GCG ACT ATC AAT AGT CGT   576

TAT AAT GAT TTA ACT AGG CTT ATT GGC AAC TAT ACA GAT TAT GCT GTA   624

CGC TGG TAC AAT ACG GGA TTA GAA CGT GTA TGG GGA CCG GAT TCT AGA   672

GAT TGG GTA AGG TAT AAT CAA TTT AGA AGA GAA TTA ACA CTA ACT GTA   720

TTA GAT ATC GTT GCT CTG TTC CCG AAT TAT GAT AGT AGA AGA TAT CCA   768

ATT CGA ACA GTT TCC CAA TTA ACA AGA GAA ATT TAT ACA AAC CCA GTA   816

TTA GAA AAT TTT GAT GGT AGT TTT CGA GGC TCG GCT CAG GGC ATA GAA   864

AGA AGT ATT AGG AGT CCA CAT TTG ATG GAT ATA CTT AAC AGT ATA ACC   912

ATC TAT ACG GAT GCT CAT AGG GGT TAT TAT TAT TGG TCA GGG CAT CAA   960

ATA ATG GCT TCT CCT GTA GGG TTT TCG GGG CCA GAA TTC ACT TTT CCG  1008

CTA TAT GGA ACT ATG GGA AAT GCA GCT CCA CAA CAA CGT ATT GTT GCT  1056

CAA CTA GGT CAG GGC GTG TAT AGA ACA TTA TCG TCC ACT TTA TAT AGA  1104

AGA CCT TTT AAT ATA GGG ATA AAT AAT CAA CAA CTA TCT GTT CTT GAC  1152

GGG ACA GAA TTT GCT TAT GGA ACC TCC TCA AAT TTG CCA TCC GCT GTA  1200

TAC AGA AAA AGC GGA ACG GTA GAT TCG CTG GAT GAA ATA CCG CCA CAG  1248

AAT AAC AAC GTG CCA CCT AGG CAA GGA TTT AGT CAT CGA TTA AGC CAT  1296

GTT TCA ATG TTT CGT TCA GGC TTT AGT AAT AGT AGT GTA AGT ATA ATA  1344

AGA GCT CCT ATG TTC TCT TGG ATA CAT CGT AGT GCA ACT CTT ACA AAT  1392

ACA ATT GAT CCA GAG AGA ATT AAT CAA ATA CCT TTA GTG AAA GGA TTT  1440

AGA GTT TGG GGG GGC ACC TCT GTC ATT ACA GGA CCA GGA TTT ACA GGA  1488

GGG GAT ATC CTT CGA AGA AAT ACC TTT GGT GAT TTT GTA TCT CTA CAA  1536

GTC AAT ATT AAT TCA CCA ATT ACC CAA AGA TAC CGT TTA AGA TTT CGT  1584

TAC GCT TCC AGT AGG GAT GCA CGA GTT ATA GTA TTA ACA GGA GCG GCA  1632

TCC ACA GGA GTG GGA GGC CAA GTT AGT GTA AAT ATG CCT CTT CAG AAA  1680
```

-continued

```
ACT ATG GAA ATA GGG GAG AAC TTA ACA TCT AGA ACA TTT AGA TAT ACC  1728
GAT TTT AGT AAT CCT TTT TCA TTT AGA GCT AAT CCA GAT ATA ATT GGG  1776
ATA AGT GAA CAA CCT CTA TTT GGT GCA GGT TCT ATT AGT AGC GGT GAA  1824
CTT TAT ATA GAT AAA ATT GAA ATT ATT CTA GCA GAT GCA ACA TTT GAA  1872
GCA GAA TCT GAT TTA GAA AGA GCA CAA AAG GCG GTG AAT GCC CTG TTT  1920
ACT TCT TCC AAT CAA ATC GGG TTA AAA ACC GAT GTG ACG GAT TAT CAT  1968
ATT GAT CAA GTA TCC AAT TTA GTG GAT TGT TTA TCA GAT GAA TTT TGT  2016
CTG GAT GAA AAG CGA GAA TTG TCC GAG AAA GTC AAA CAT GCG AAG CGA  2064
CTC AGT GAT GAG CGG AAT TTA CTT CAA GAT CCA AAC TTC AGA GGG ATC  2112
AAT AGA CAA CCA GAC CGT GGC TGG AGA GGA AGT ACA GAT ATT ACC ATC  2160
CAA GGA GGA GAT GAC GTA TTC AAA GAG AAT TAC GTC ACA CTA CCG GGT  2208
ACC GTT GAT GAG TGC TAT CCA ACG TAT TTA TAT CAG AAA ATA GAT GAG  2256
TCG AAA TTA AAA GCT TAT ACC CGT TAT GAA TTA AGA GGG TAT ATC GAA  2304
GAT AGT CAA GAC TTA GAA ATC TAT TTG ATC CGT TAC AAT GCA AAA CAC  2352
GAA ATA GTA AAT GTG CCA GGC ACG GGT TCC TTA TGG CCG CTT TCA GCC  2400
CAA AGT CCA ATC GGA AAG TGT GGA GAA CCG AAT CGA TGC GCG CCA CAC  2448
CTT GAA TGG AAT CCT GAT CTA GAT TGT TCC TGC AGA GAC GGG GAA AAA  2496
TGT GCA CAT CAT TCC CAT CAT TTC ACC TTG GAT ATT GAT GTT GGA TGT  2544
ACA GAC TTA AAT GAG GAC TTA GGT GTA TGG GTG ATA TTC AAG ATT AAG  2592
ACG CAA GAT GGC CAT GCA AGA CTA GGG AAT CTA GAG TTT CTC GAA GAG  2640
AAA CCA TTA TTA GGG GAA GCA CTA GCT CGT GTG AAA AGA GCG GAG AAG  2688
AAG TGG AGA GAC AAA CGA GAG AAA CTG CAG TTG GAA ACA AAT ATT GTT  2736
TAT AAA GAG GCA AAA GAA TCT GTA GAT GCT TTA TTT GTA AAC TCT CAA  2784
TAT GAT AGA TTA CAA GTG GAT ACG AAC ATC GCA ATG ATT CAT GCG GCA  2832
GAT AAA CGC GTT CAT AGA ATC CGG GAA GCG TAT CTG CCA GAG TTG TCT  2880
GTG ATT CCA GGT GTC AAT GCG GCC ATT TTC GAA GAA TTA GAG GGA CGT  2928
ATT TTT ACA GCG TAT TCC TTA TAT GAT GCG AGA AAT GTC ATT AAA AAT  2976
GGC GAT TTC AAT AAT GGC TTA TTA TGC TGG AAC GTG AAA GGT CAT GTA  3024
GAT GTA GAA GAG CAA AAC AAC CAC CGT TCG GTC CTT GTT ATC CCA GAA  3072
TGG GAG GCA GAA GTG TCA CAA GAG GTT CGT GTC TGT CCA GGT CGT GGC  3120
TAT ATC CTT CGT GTC ACA GCA TAT AAA GAG GGA TAT GGA GAG GGC TGC  3168
GTA ACG ATC CAT GAG ATC GAA GAC AAT ACA GAC GAA CTG AAA TTC AGC  3216
AAC TGT GTA GAA GAG GAA GTA TAT CCA AAC AAC ACA GTA ACG TGT AAT  3264
AAT TAT ACT GGG ACT CAA GAA GAA TAT GAG GGT ACG TAC ACT TCT CGT  3312
AAT CAA GGA TAT GAC GAA GCC TAT GGT AAT AAC CCT TCC GTA CCA GCT  3360
GAT TAC GCT TCA GTC TAT GAA GAA AAA TCG TAT ACA GAT GGA CGA AGA  3408
GAG AAT CCT TGT GAA TCT AAC AGA GGC TAT GGG GAT TAC ACA CCA CTA  3456
CCG GCT GGT TAT GTA ACA AAG GAT TTA GAG TAC TTC CCA GAG ACC GAT  3504
AAG GTA TGG ATT GAG ATC GGA GAA ACA GAA GGA ACA TTC ATC GTG GAT  3552
AGC GTG GAA TTA CTC CTT ATG GAG GAA                              3579
```

6.7.7 DNA Sequence Encoding the EG11768 Crystal Protein (SEQ ID NO:33)

```
ATG GAT AAC AAT CCG AAC ATC AAT GAA TGC ATT CCT TAT AAT TGT TTA    48

AGT AAC CCT GAA GTA GAA GTA TTA GGT GGA GAA AGA ATA GAA ACT GGT    96

TAC ACC CCA ATC GAT ATT TCC TTG TCG CTA ACG CAA TTT CTT TTG AGT   144

GAA TTT GTT CCC GGT GCT GGA TTT GTG TTA GGA CTA GTT GAT ATA ATA   192

TGG GGA ATT TTT GGT CCC TCT CAA TGG GAC GCA TTT CTT GTA CAA ATT   240

GAA CAG TTA ATT AAC CAA AGA ATA GAA GAA TTC GCT AGG AAC CAA GCC   288

ATT TCT AGA TTA GAA GGA CTA AGC AAT CTT TAT CAA ATT TAC GCA GAA   336

TCT TTT AGA GAG TGG GAA GCA GAT CCT ACT AAT CCA GCA TTA AGA GAA   384

GAG ATG CGT ATT CAA TTC AAT GAC ATG AAC AGT GCC CTT ACA ACC GCT   432

ATT CCT CTT TTT GCA GTT CAA AAT TAT CAA GTT CCT CTT TTA TCA GTA   480

TAT GTT CAA GCT GCA AAT TTA CAT TTA TCA GTT TTG AGA GAT GTT TCA   528

GTG TTT GGA CAA AGG TGG GGA TTT GAT GCC GCG ACT ATC AAT AGT CGT   576

TAT AAT GAT TTA ACT AGG CTT ATT GGC AAC TAT ACA GAT TAT GCT GTA   624

CGC TGG TAC AAT ACG GGA TTA GAA CGT GTA TGG GGA CCG GAT TCT AGA   672

GAT TGG GTA AGG TAT AAT CAA TTT AGA AGA GAA TTA ACA CTA ACT GTA   720

TTA GAT ATC GTT GCT CTG TTC CCG AAT TAT GAT AGT AGA AGA TAT CCA   768

ATT CGA ACA GTT TCC CAA TTA ACA AGA GAA ATT TAT ACA AAC CCA GTA   816

TTA GAA AAT TTT GAT GGTAGT TTT CGA GGC TCG GCT CAG GGC ATA GAA    864

AGA AGT ATT AGG AGT CCA CAT TTG ATG GAT ATA CTT AAC AGT ATA ACC   912

ATC TAT ACG GAT GCT CAT AGG GGT TAT TAT TAT TGG TCA GGG CAT CAA   960

ATA ATG GCT TCT CCT GTA GGG TTT TCG GGG CCA GAA TTC ACT TTT CCG  1008

CTA TAT GGA ACT ATG GGA AAT GCA GCT CCA CAA CAA CGT ATT GTT GCT  1056

CAA CTA GGT CAG GGC GTG TAT AGA ACA TTA TCG TCC ACT TTA TAT AGA  1104

AGA CCT TTT AAT ATA GGG ATA AAT AAT CAA CAA CTA TCT GTT CTT GAC  1152

GGG ACA GAA TTT GCT TAT GGA ACC TCC TCA AAT TTG CCA TCC GCT GTA  1200

TAC AGA AAA AGC GGA ACG GTA GAT TCG CTG GAT GAA ATA CCG CCA CAG  1248

AAT AAC AAC GTG CCA CCT AGG CAA GGA TTT AGT CAT CGA TTA AGC CAT  1296

GTT TCA ATG TTT CGT TCA GGC TTT AGT AAT AGT AGT GTA AGT ATA ATA  1344

AGA GCT CCT ATG TTC TCT TGG ATA CAT CGT AGT GCT GAA TTT AAT AAT  1392

ATA ATT GCA TCG GAT AGT ATT ACT CAA ATA CCA TTG GTA AAA GCA CAT  1440

ACA CTT CAG TCA GGT ACT ACT GTT GTA AGA GGG CCC GGG TTT ACG GGA  1488

GGA GAT ATT CTT CGA CGA ACA AGT GGA GGA CCA TTT GCT TAT ACT ATT  1536

GTT AAT ATA AAT GGG CAA TTA CCC CAA AGG TAT CGT GCA AGA ATA CGC  1584

TAT GCC TCT ACT ACA AAT CTA AGA ATT TAC GTA ACG GTT GCA GGT GAA  1632

CGG ATT TTT GCT GGT CAA TTT AAC AAA ACA ATG GAT ACC GGT GAC CCA  1680

TTA ACA TTC CAA TCT TTT AGT TAC GCA ACT ATT AAT ACA GCT TTT ACA  1728

TTC CCA ATG AGC CAG AGT AGT TTC ACA GTA GGT GCT GAT ACT TTT AGT  1776

TCA GGG AAT GAA GTT TAT ATA GAC AGA TTT GAA TTG ATT CCA GTT ACT  1824
```

-continued

```
GCA ACA CTC GAG GCT GAA TAT AAT CTG GAA AGA GCG CAG AAG GCG GTG  1872

AAT GCG CTG TTT ACG TCT ACA AAC CAA CTA GGG CTA AAA ACA AAT GTA  1920

ACG GAT TAT CAT ATT GAT CAA GTG TCC AAT TTA GTT ACG TAT TTA TCG  1968

GAT GAA TTT TGT CTG GAT GAA AAG CGA GAA TTG TCC GAG AAA GTC AAA  2016

CAT GCG AAG CGA CTC AGT GAT GAA CGC AAT TTA CTC CAA GAT TCA AAT  2064

TTC AAA GAC ATT AAT AGG CAA CCA GAA CGT GGG TGG GGC GGA AGT ACA  2112

GGG ATT ACC ATC CAA GGA GGG GAT GAC GTA TTT AAA GAA AAT TAC GTC  2160

ACA CTA TCA GGT ACC TTT GAT GAG TGC TAT CCA ACA TAT TTG TAT CAA  2208

AAA ATC GAT GAA TCA AAA TTA AAA GCC TTT ACC CGT TAT CAA TTA AGA  2256

GGG TAT ATC GAA GAT AGT CAA GAC TTA GAA ATC TAT TTA ATT CGC TAC  2304

AAT GCA AAA CAT GAA ACA GTA AAT GTG CCA GGT ACG GGT TCC TTA TGG  2352

CCG CTT TCA GCC CAA AGT CCA ATC GGA AAG TGT GGA GAG CCG AAT CGA  2400

TGC GCG CCA CAC CTT GAA TGG AAT CCT GAC TTA GAT TGT TCG TGT AGG  2448

GAT GGA GAA AAG TGT GCC CAT CAT TCG CAT CAT TTC TCC TTA GAC ATT  2496

GAT GTA GGA TGT ACA GAC TTA AAT GAG GAC CTA GGT GTA TGG GTG ATC  2544

TTT AAG ATT AAG ACG CAA GAT GGG CAC GCA AGA CTA GGG AAT CTA GAG  2592

TTT CTC GAA GAG AAA CCA TTA GTA GGA GAA GCG CTA GCT CGT GTG AAA  2640

AGA GCG GAG AAA AAA TGG AGA GAC AAA CGT GAA AAA TTG GAA TGG GAA  2688

ACA AAT ATC GTT TAT AAA GAG GCA AAA GAA TCT GTA GAT GCT TTA TTT  2736

GTA AAC TCT CAA TAT GAT CAA TTA CAA GCG GAT ACG AAT ATT GCC ATG  2784

ATT CAT GCG GCA GAT AAA CGT GTT CAT AGC ATT CGA GAA GCT TAT CTG  2832

CCT GAG CTG TCT GTG ATT CCG GGT GTC AAT GCG GCT ATT TTT GAA GAA  2880

TTA GAA GGG CGT ATT TTC ACT GCA TTC TCC CTA TAT GAT GCG AGA AAT  2928

GTC ATT AAA AAT GGT GAT TTT AAT AAT GGC TTA TCC TGC TGG AAC GTG  2976

AAA GGG CAT GTA GAT GTA GAA GAA CAA AAC AAC CAA CGT TCG GTC CTT  3024

GTT GTT CCG GAA TGG GAA GCA GAA GTG TCA CAA GAA GTT CGT GTC TGT  3072

CCG GGT CGT GGC TAT ATC CTT CGT GTC ACA GCG TAC AAG GAG GGA TAT  3120

GGA GAA GGT TGC GTA ACC ATT CAT GAG ATC GAG AAC AAT ACA GAC GAA  3168

CTG AAG TTT AGC AAC TGC GTA GAA GAG GAA ATC TAT CCA AAT AAC ACG  3216

GTA ACG TGT AAT GAT TAT ACT GTA AAT CAA GAA GAA TAC GGA GGT GCG  3264

TAC ACT TCT CGT AAT CGA GGA TAT AAC GAA GCT CCT TCC GTA CCA GCT  3312

GAT TAT GCG TCA GTC TAT GAA GAA AAA TCG TAT ACA GAT GGA CGA AGA  3360

GAG AAT CCT TGT GAA TTT AAC AGA GGG TAT AGG GAT TAC ACG CCA CTA  3408

CCA GTT GGT TAT GTG ACA AAA GAA TTA GAA TAC TTC CCA GAA ACC GAT  3456

AAG GTA TGG ATT GAG ATT GGA GAA ACG GAA GGA ACA TTT ATC GTG GAC  3504

AGC GTG GAA TTA CTC CTT ATG GAG GAA TAG                          3534
```

7. REFERENCES

The following references, to the extent that they provide exemplary procedural or other details supplementary to those set forth herein, are specifically incorporated herein by reference.

U.S. Pat. No. 4,554,101.
U.S. Pat. No. 4,683,195.
U.S. Pat. No. 4,683,202.
U.S. Pat. No. 4,702,914.
U.S. Pat. No. 4,757,011.
U.S. Pat. No. 4,769,061.
U.S. Pat. No. 4,940,835.
U.S. Pat. No. 4,965,188.
U.S. Pat. No. 4,971,908.

U.S. Pat. No. 5,004,863.
U.S. Pat. No. 5,015,580.
U.S. Pat. No. 5,055,294.
U.S. Pat. No. 5,128,130.
U.S. Pat. No. 5,176,995.
U.S. Pat. No. 5,349,124.
U.S. Pat. No. 5,380,831.
U.S. Pat. No. 5,384,253.
U.S. Pat. No. 5,416,102.
U.S. Pat. No. 5,441,884.
U.S. Pat. No. 5,449,681.
U.S. Pat. No. 5,500,365.
U.S. Pat. No. 5,659,123.
Intl. Pat. Appl. Publ. No. WO 91/10725, published Jul. 25, 1991.
Intl. Pat. Appl. Publ. No. WO 93/07278, published Apr. 15, 1993.
Intl. Pat. Appl. Publ. No. WO 95/02058, published Jan. 19, 1995.
Intl. Pat. Appl. Publ. No. WO 95/06730, published Mar. 9, 1995.
Intl. Pat. Appl. Publ. No. WO 95/30752, published Nov. 16, 1995.
Intl. Pat. Appl. Publ. No. WO 95/30753, published Nov. 16, 1995.
Abdullah el al., *Biotechnology*, 4:1087, 1986.
Adelman et al., DNA, 2/3:183–193, 1983.
Allen and Choun, "Large unilamellar liposomes with low uptake into the reticuloendothelial system," *FEBS Lett.*, 223:42–46, 1987.
Altschul, Stephen F. et al., "Basic local alignment search tool," *J. Mol. Biol*, 215:403–410, 1990.
Arvidson et al., Mol. Biol., 3:1533–1534, 1989.
Baum et al., *Appl. Environ. Microbiol.*, 56:3420–3428, 1990.
Benbrook et al., *In: Proceedings Bio Expo* 1986, Butterworth, Stoneham, Mass., pp. 27–54, 1986.
Bolivar et al., *Gene*, 2:95, 1977.
Bosch et al., "Recombinant *Bacillus thuringiensis* Crystal Proteins with New Properties: Possibilities for Resistance Management," *Bio/Technology*, 12:915–918, 1994.
Bytebier et al., *Proc. Natl. Acad. Sci. USA*, 84:5345, 1987.
Callis et al., *Genes Develop.* 1:1183, 1987.
Campbell, "Monoclonal Antibody Technology, Laboratory Techniques in Biochemistry and Molecular Biology," Vol. 13, Burden and Von Knippenberg, Eds. pp. 75–83, Elsevier, Amsterdam, 1984.
Capecchi, M. R., "High efficiency transformation by direct microinjection of DNA into cultured mammalian cells," *Cell* 22(2):479488, 1980.
Cashmore et al., *Gen. Eng. of Plants*, Plenum Press, New York, 29–38, 1983.
Chambers et al., *J. Bacteriol.*, 173:3966–3976, 1991.
Chang et al., *Nature*, 375:615, 1978.
Chau et al., *Science*, 244:174181, 1989.
Clapp, D. W., "Somatic gene theraphy into hematopojetic cells. Current status and future implications," *Clin. Perinatol.* 20(1):155–168, 1993.
Couvreur et al., "Nanocapsules, a new lysosomotropic carrier," *FEBS Lett.*, 84:323–326, 1977.
Couvreur, "Polyalkyleyanoacrylates as colloidal drug carriers," *Crit. Rev. Ther. Drug Carrier Syst.*, 5:1–20, 1988.
Crickmore et al., *Abstr. 28th Annu. Meet. Soc. Invert. Pathol.*, Cornell University, Ithaca, N.Y., 1995.
Cristou et al., *Plant Physiol*, 87:671–674, 1988.
Curiel, D. T., Agarwal, S., Wagner, E., and Cotten, M., "Adenovirus enhancement of transferrin-polylysine-mediated gene delivery," *Proc. Natl. Acad. Sci. USA*, 88(19):8850–8854, 1991.
Curiel, D. T., Wagner, E., and Cotten, M., Birnstiel, M. L., Agarwal, S., Li, C. M., Loechel, S., and Hu, P. C. high-efficiency gene transfer mediated by adenovirus coupled to DNA-polylysine complexes," *Hum. Gen. Ther.*, 3(2):147–154, 1992.
Dhir et al., *Plant Cell Reports*, 10:97, 1991.
Eglitis, M. A., and Anderson, W. F., "Retroviral vectors for introduction of genes into manmnalian cells," *Biotechniques*, 6(7):608–614, 1988.
Eglitis, M. A., Kantoff, P. W., Kohn, D. B., Karson, E., Moen, R. C., Lothrop, C. D., Blaese, R. M., and Anderson, W. F., "Retroviral-mediated gene transfer into hemopoietic cells," *Adv. Exp. Med. Biol.*, 241:19–27, 1988.
Eichenlaub, R., *J. Bacteriol.*, 138(2):559–566, 1979.
Fiers et al., *Nature*, 273:113, 1978.
Fraley et al., *Biotechnology*, 3:629, 1985.
Fraley et al., *Proc. Natl. Acad. Sci. USA*, 80:4803, 1983.
Fromm, M., Taylor, L. P., and Walbot, V., "Expression of genes transferred into monocot and dicot plant cells by electroporation," *Proc. Natl. Acad. Sci. USA*, 82(17):5824–5828, 1985.
Fujimura et al., *Plant Tissue Culture Letters*, 2:74, 1985.
Fynan, E. F., Webster, R. G., Fuller, D. H., Haynes, J. R., Santoro, J. C., and Robinson, H. L., "DNA vaccines: protective immunizations by parenteral, mucosal, and gene gun inoculations," *Proc. Natl. Acad. Sci. USA*, 90(24):11478–11482, 1993.
Gawron-Burke and Baum, *Genet. Engineer.*, 13:237–263, 1991.
Gefter et al., *Somat. Cell Genet.*, 3:231–236, 1977.
Gill et al., *J. Biol. Chem.*, 270:27277–27282, 1995.
Goding, "Monoclonal Antibodies: Principles and Practice," pp. 60–74. 2nd Edition, Academic Press, Orlando, Fla., 1986.
Goeddel et al., *Nature*, 281:544, 1979.
Goeddel et al., *Nucl. Acids Res.*, 8:4057, 1980.
Graham, F. L., and van der Eb, A. J., "Transformation of rat cells by DNA of human adenovirus 5," *Virology*, 54(2):536–539, 1973.
Green, *Nucl. Acids Res.* 16(1):369. 1988.
Grochulski et al., *J. Mol. Biol.*, 254:447464, 1995.
Harlow, E. and Lane, D. "Antibodies: A Laboratory Manual," Cold Spring Harbor Laboratory, Cold Spring Harbor, N.Y., 1988.
Henry-Michelland el al., "Attachment of antibiotics to nanoparticles; Preparation, drug-release and antimicrobial activity in vitro, *Int. J. Pharm.*, 35:121–127, 1987.
Hess et al., *J. Adv. Enzyme Reg.*, 7:149, 1968.
Hilber, U. W., Bodmer, M., Smith, F. D., and Koller, W., "Biolistic transformation of conidia of *Botryotinia fuckeliana,*" *Curr. Genet.*, 25(2):124–127, 1994.
Hitzeman et al., *J. Biol. Chem.*, 255:2073, 1980.
Höfte and Whiteley, *Microbiol. Rev.*, 53:242–255, 1989.
Holland et al., *Biochemistry*, 17:4900, 1978.
Honeee et al., *Mol. Microbiol.*, 5:2799–2806, 1991.
Hoover et al., (Eds.), "Remington's Pharmaceutical Sciences," 15th Edition, Mack Publishing Co., Easton, Pa., 1975.
Horsch et al., *Science*, 227:1229–1231, 1985.
Horton et al., *Gene*, 77:61–68, 1989.
Humason, "Animal Tissue Techniques," W. H. Freeman & Company, New York, 1967.
Itakura et al., *Science*, 198:1056, 1977.
Jameson and Wolf, "The Antigenic Index: A Novel Algorithm for Predicting Antigenic Determinants," *Compu. Appl. Biosci.*, 4(1):181–6, 1988.

Johnston, S. A., and Tang, D. C., "Gene gun transfection of animal cells and genetic immunization," *Methods Cell. Biol.*, 43(A):353–365, 1994.

Jones, *Genetics*, 85:12 1977.

Jorgensen et al., *Mol. Gen. Genet.*, 207:471, 1987.

Keller et al., *EMBO J.*, 8:1309–14, 1989.

Kingsman et al., Gene, 7:141, 1979.

Klee et al., *Bio/Technology*, 3:637, 1985.

Klein et al., *Nature*, 327:70, 1987.

Klein et al., *Proc. Natl. Acad. Sci. USA*, 85:8502–8505, 1988.

Knight et al., *J. Biol. Chem.*, 270:17765–17770, 1995.

Kohler and Milstein, *Eur. J. Immunol.*, 6:511–519, 1976.

Kohler and Milstein, *Nature*, 256:495497, 1975.

Kuby, J., *Immunology 2nd Edition*, W. H. Freeman & Company, New York, 1994.

Kyte, J., and Doolittle, R. F., A simple method for displaying the hydropathic character of a protein," *J. Mol. Biol.*, 157(1):105–132, 1982.

Langridge et al., *Proc. Natl. Acad. Sci. USA*, 86:3219–3223, 1989.

Lee et al., *Biochem. Biophys. Res. Comm.*, 216:306–312, 1995.

Lindstrom et al., *Develop. Genet.*, 11:160, 1990.

Lorz et al., *Mol. Gen. Genet.*, 199:178, 1985.

Lu, L., Xiao, M., Clapp, D. W., Li Z. H., and Broxmeyer, H. E., "High efficiency retroviral mediated gene transduction into single isolated immature and replatable CD34(3+) hematopoietic stem/progenitor cells from human umbilical cord blood," *J. Exp. Med.* 178(6):2089–2096, 1993.

Luo et al., *Plant Mol. Biol. Report*, 6:165, 1988.

Maddock et al., *Third Intl. Congr. Plant Mol. Biol.*, Abstr. No. 372, 1991.

Maloy et al., "Microbial Genetics" 2nd Ed, Jones & Bartlett Publishers, Boston, Mass., 1994.

Prokop, A., and Bajpai, R. K. "Recombinant DNA Technology I" *Ann. N.Y. Acad. Sci.*, Vol. 646, 1991.

Maniatis et al., "Molecular Cloning: a Laboratory Manual," Cold Spring Harbor Laboratory, Cold Spring Harbor, N.Y., 1982.

Marcotte et al., *Nature*, 335:454, 1988.

Masson et al., *J. Biol. Chem.*, 270:20309–20315, 1995.

McCabe et al., *Biotechnology*, 6:923, 1988.

Mettus and Macaluso, *Appl. Environ. Microbiol.*, 56:1128–1134, 1990.

Neuhaus et al., *Theor. Appl. Genet.*, 75:30, 1987.

Odell et al., *Nature*, 313:810, 1985.

Omirulleh et al., *Plant Mol. Biol.*, 21:415428, 1993.

Pena et al., *Nature*, 325:274, 1987.

Poszkowski et al., *EMBO J*, 3:2719, 1989.

Potrykus et al., *Mol. Gen. Genet.*, 199:183, 1985.

Poulsen et al., *Mol. Gen. Genet.*, 205:193–200, 1986.

Prokop, A., Bajpai, R. K., *Ann N.Y. Acad. Sci.*, 646, 1991

Rogers et al., In: "Methods For Plant Molecular Biology," A. Weissbach and H.

Weissbach, eds., Academic Press Inc., San Diego, Calif. 1988.

Rogers et al., *Methods Enzymol.*, 153:253–277, 1987.

Ruud et al., "Domain III Substitution in *Bacillus thuringiensis* Delta-Endotoxin CryIA(b) Results in Superior Toxicity for *Spodoptera exigua* and Altered Membrane Protein Recognition," *Appl. Environ. Microbiol.*, 62(5):1537–1543, 1996.

Ruud et al., "Different Domains of *Bacillus thuringiensis* δ-Endotoxins Can Bind to Insect Midgut Membrane Proteins on Ligand Blots," *Appl. Environ. Microbiol.*, 62(8):2753–2757, 1996.

Sambrook et al., "Molecular Cloning: A Laboratory Manual," Cold Spring Harbor Laboratory, Cold Spring Harbor, N.Y., 1989.

Schnepf et al., *J. Biol. Chem.*, 265:20923–20930, 1990.

Segal, I. H., "Biochemical Calculations" 2nd Ed., John Wiley & Sons, New York, 1976.

Simpson, *Science*, 233:34, 1986.

Spielmann et al., *Mol. Gen. Genet.*, 205:34, 1986.

Spoerel, *Methods Enzymol.*, 152:588–597, 1987.

Stinchcomb et al., *Nature*, 282:39, 1979.

Thompson et al., *Genet. Engineer.*, 17:99–117, 1995.

Toriyama et al., *Theor. Appl. Genet.*, 73:16, 1986.

Tschemper et al., *Gene*, 10: 157, 1980.

Uchimiya et al., *Mol. Gen. Genet.*, 204:204, 1986.

Van Tunen et al., *EMBO J.*, 7:1257,1988.

Vasil, *Biotechnology*, 6:397, 1988.

Vasil et al., "Herbicide-resistant fertile transgenic wheat plants obtained by microprojectile bombardment of regenerable embryogenic callus," *Biotechnology*, 10:667674, 1992.

Vodkin et al., *Cell*, 34:1023, 1983.

Vogel et al., *J. Cell Biochem.*, (Suppl.) 13D:312, 1989.

Wagner, E., Zatloukal, K., Cotten, M., Kirlappos, H., Mechtler, K., Curiel, D. T., and Bitmstiel, M. L., "Coupling of adenovirus to transferrin-polylysine/DNA complexes greatly enhances receptor-mediated gene delivery and expression of transfected genes," *Proc. Natl. Acad. Sci., USA* 89(13):6099–6103, 1992.

Weissbach and Weissbach, *Methods for Plant Molecular Biology*, (eds.), Academic Press, Inc., San Diego, Calif., 1988.

Wenzler et al., *Plant Mol. Biol.*, 12:41–50,1989.

Wolf et al., "An Integrated Family of Amino Acid Sequence Analysis Programs," *Compu. Appl. Biosci.*, 4(1):187–91, 1988.

Wong, T. E., and Neumann, E., "Electric field mediated gene transfer," *Biochim. Biophys. Res. Commun.*, 107(2):584–587, 1982.

Yamada et al., *Plant Cell Rep.*, 4:85, 1986.

Yang et al., *Proc. Natl. Acad. Sci. USA*, 87:4144–48, 1990.

Zhou et al., *Methods Enzymol.*, 101:433, 1983.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A transgenic plant having incorporated into its genome a selected polynucleotide, said polynucleotide comprising a nucleic acid sequence that encodes a polypeptide comprising the amino acid sequence of SEQ ID NO:34.

2. The transgenic plant of claim 1, wherein said nucleic acid sequence comprises the nucleotide sequence of SEQ ID NO:33.

3. A progeny of any generation of the plant of claim 1, wherein said progeny comprises said nucleic acid sequence.

4. A seed of any generation of the plant of claim 1, wherein said seed comprises said nucleic acid sequence.

5. A seed of any generation of the progeny of claim 3, wherein said seed comprises said nucleic acid sequence.

6. A plant of any generation from the seed of claim 5, wherein said plant comprises said nucleic acid sequence.

7. The transgenic plant of claim 1, further defined as a monocotyledonousplant.

8. The transgenic plant of claim 7, further defined as a corn, wheat, oat, rice, barley, turf grass, or pasture grass plant.

9. The transgenic plant of claim 8, further defined as a corn plant.

10. The transgenic plant of claim 1, further defined as a dicotyledonousplant.

11. The transgenic plant of claim 10, further defined as a legume, soybean, cotton, fruit, berry, or tree.

12. The transgenic plant of claim 11, further defined as soybean or cotton.

13. The transgenic plant of claim 1, wherein said nucleic acid sequence is operably linked to a promoter.

14. The transgenic plant of claim 13, wherein said promoter comprises a constitutive, inducible, viral, synthetic, or tissue-specific promoter.

15. The transgenic plant of claim 14, wherein said promoter is a temporally regulated, a spatially regulated, or a spatio-temporally regulated promoter.

16. The transgenic plant of claim 14, wherein said promoter is selected from the group consisting of a sigA gene promoter, a sigE gene promoter, a sigK gene promoter, a corn sucrose synthetase promoter, a corn alcohol dehydrogenase 1 promoter, a corn light harvesting complex promoter, a corn heat shock protein promoter, a pea small subunit RuBP carboxylase promoter, a Ti plasmid mannopine synthase promoter, a Ti plasmid nopaline synthase promoter, a petunia chalcone isomerase promoter, a bean glycine rich protein 1 promoter, a CaMV 35s promoter, a Potato patatin promoter, and a lectin promoter.

17. The transgenic plant of claim 1, wherein said selected polynucleotide is introduced into said plant by PEG-mediated transformation of protoplasts, by desiccation/inhibition-mediated DNA uptake, by electroporation, by agitation with silicon carbide fibers, by acceleration of polynucleotide-coated particles, by microprojectile bombardment, or by Agrobacterium-mediated transformation.

* * * * *